United States Patent
Bicknell et al.

(10) Patent No.: US 9,255,148 B2
(45) Date of Patent: Feb. 9, 2016

(54) CLEC14A INHIBITORS

(75) Inventors: Roy Bicknell, Birmingham (GB);
Xiaodong Zhuang, Birmingham (GB);
Manuela Mura, Birmingham (GB)

(73) Assignee: Cancer Research Technology Limited, London (GB)

( * ) Notice: Subject to any disclaimer, the term of this patent is extended or adjusted under 35 U.S.C. 154(b) by 307 days.

(21) Appl. No.: 13/393,921

(22) PCT Filed: Sep. 3, 2010

(86) PCT No.: PCT/GB2010/001689
§ 371 (c)(1),
(2), (4) Date: Jun. 18, 2012

(87) PCT Pub. No.: WO2011/027132
PCT Pub. Date: Mar. 10, 2011

(65) Prior Publication Data
US 2012/0276000 A1    Nov. 1, 2012

Related U.S. Application Data

(60) Provisional application No. 61/239,584, filed on Sep. 3, 2009.

(51) Int. Cl.
*A61K 35/00* (2006.01)
*A61K 39/395* (2006.01)
*C07K 16/28* (2006.01)
*A61K 39/00* (2006.01)

(52) U.S. Cl.
CPC ....... *C07K 16/2851* (2013.01); *A61K 2039/505* (2013.01); *C07K 2317/76* (2013.01)

(58) Field of Classification Search
CPC .... C07K 14/47; C07K 16/30; C07K 2317/76; C07K 14/705; A61K 2300/00; A61K 2039/505; A61K 39/39558; A61K 47/48384; A61K 47/48584; C12Q 2600/158; C12Q 1/6886
See application file for complete search history.

(56) References Cited

U.S. PATENT DOCUMENTS

| | | | |
|---|---|---|---|
| 4,348,376 A | 9/1982 | Goldenberg | |
| 4,946,778 A | 8/1990 | Ladner et al. | |
| 5,354,855 A | 10/1994 | Cech et al. | |
| 5,800,988 A | 9/1998 | Casterman et al. | |
| 5,840,526 A | 11/1998 | Casterman et al. | |
| 5,874,541 A | 2/1999 | Casterman et al. | |
| 6,005,079 A | 12/1999 | Casterman et al. | |
| 6,015,695 A | 1/2000 | Casterman et al. | |
| 6,225,118 B1 | 5/2001 | Grant et al. | |
| 6,503,242 B1 | 1/2003 | Elsberry | |
| 6,765,087 B1 | 7/2004 | Casterman et al. | |
| 6,894,148 B2 | 5/2005 | Goddard et al. | |
| 2003/0175900 A1 | 9/2003 | Ashkenazi et al. | |
| 2003/0186358 A1 | 10/2003 | Ashkenazi et al. | |
| 2003/0194775 A1 | 10/2003 | Baker et al. | |
| 2004/0033495 A1* | 2/2004 | Murray et al. | 435/6 |
| 2005/0025746 A1 | 2/2005 | During et al. | |
| 2006/0148695 A1 | 7/2006 | Wu et al. | |

FOREIGN PATENT DOCUMENTS

| | | |
|---|---|---|
| EP | 1 589 107 B1 | 12/2009 |
| WO | WO 94/10323 A1 | 5/1994 |
| WO | WO 96/06641 A1 | 3/1996 |
| WO | WO 96/34103 A1 | 10/1996 |
| WO | WO 97/49805 A2 | 12/1997 |
| WO | WO 98/32845 A1 | 7/1998 |
| WO | WO 01/04264 A2 | 1/2001 |
| WO | WO 01/53486 A1 | 7/2001 |
| WO | WO 02/00690 A2 | 1/2002 |
| WO | WO 02/36771 A2 | 5/2002 |
| WO | WO 02/079492 A2 | 10/2002 |
| WO | WO 03/101283 A2 | 12/2003 |
| WO | WO 2004/046191 A2 | 6/2004 |
| WO | WO 2006/098887 A2 | 9/2006 |
| WO | WO 2006/135493 A2 | 12/2006 |

OTHER PUBLICATIONS

Chong et al (Clinical Cancer Research, 2005, 11:4818-4826).*
Genbank Submission; NCBI, Accession No. L04147.1: Rogaev et al; Jan. 7, 1995; 2 pages.
Genbank Submission; NCBI, Accession No. M65210.1: Morii et al; Aug. 14, 1998; 2 pages.
Genbank Submission; NCBI, Accession No. NM_175060.2: Mura et al; Jan. 13, 2013; 3 pages.
Genbank Submission; NCBI, Accession No. NM_199786.1: Gomez et al; Apr. 21, 2012; 2 pages.
Genbank Submission; NCBI, Accession No. NP_778230.1: Mura et al; Jan. 13, 2013; 2 pages.
Genbank Submission; NCBI, Accession No. X51956: Oliva et al; Oct. 23, 2008; 5 pages.
Genbank Submission; NCBI, Accession No. X59834: Van Den Hoff et al; Apr. 18, 2005; 2 pages.
[No Author Listed] "DTP Human Tumor Cell Line Screen". Anticancer Agent Mechanism Database. http://dtp.nci.nih.gov/docs/cancer/searches/standard_mechanism.html. [Last accessed: Dec. 19, 2013].
[No Author Listed] Bevacizumab combined with chemotherapy improves progression-free survival for patients with advanced breast cancer. National Cancer Institute Press Release. Apr. 14, 2005. 2 pages.
Adams et al., Initial assessment of human gene diversity and expression patterns based upon 83 million nucleotides of cDNA sequence. Nature. Sep. 28, 1995;377(6547 Suppl):3-174.
Aiello et al., Suppression of retinal neovascularization in vivo by inhibition of vascular endothelial growth factor (VEGF) using soluble VEGF-receptor chimeric proteins. Proc Natl Acad Sci U S A. Nov. 7, 1995;92(23):10457-61.

(Continued)

*Primary Examiner* — Sean Aeder
*Assistant Examiner* — Julie Wu
(74) *Attorney, Agent, or Firm* — Wolf, Greenfield & Sacks, P.C.

(57) ABSTRACT

A method of inhibiting tumor angiogenesis in an individual, the method comprising administering to the individual an inhibitor of CLEC14A. The inhibitor may be an antibody, an siRNA molecule, an antisense molecule, or a ribozyme.

21 Claims, 23 Drawing Sheets

(56) References Cited

OTHER PUBLICATIONS

Figure 3:
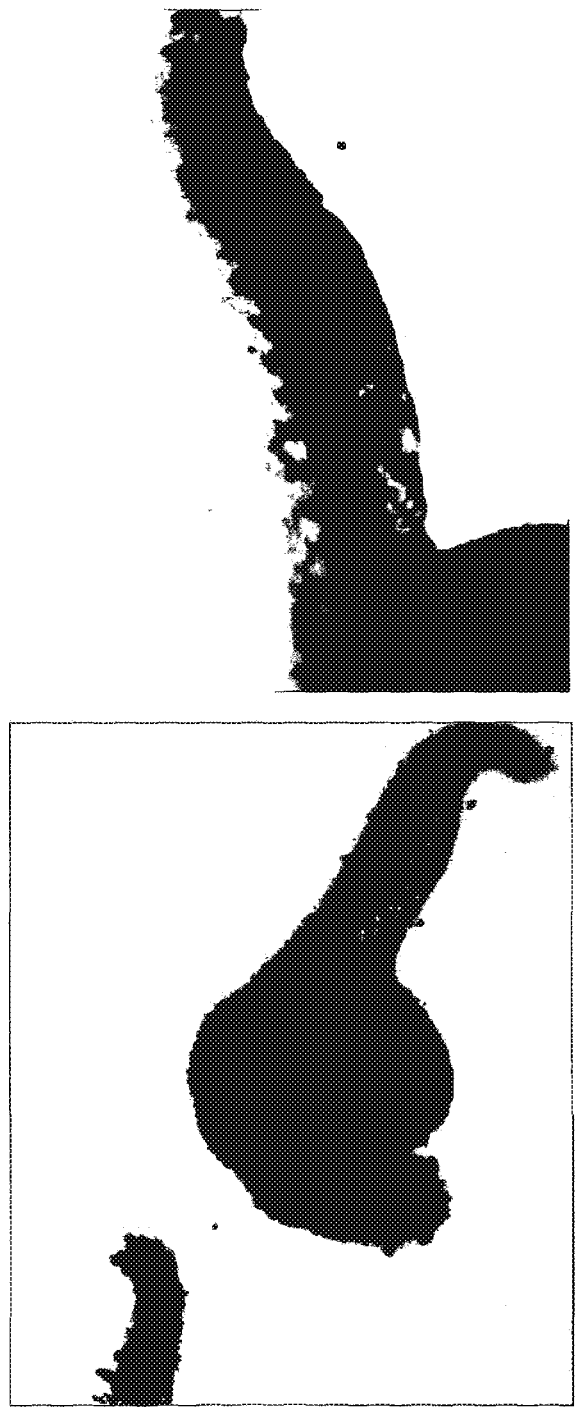

Altinoglu et al., Near-infrared emitting fluorophore-doped calcium phosphate nanoparticles for in vivo imaging of human breast cancer. ACS Nano. Oct. 28, 2008;2(10):2075-84.

Anderson-Engels et al., In vivo fluorescence imaging for tissue diagnostics. Phys Med Biol. May 1997;42(5):815-24.

Arkin et al., Small-molecule inhibitors of protein-protein interactions: progressing towards the dream. Nat Rev Drug Discov. Apr. 2004;3(4):301-17.

Bagshawe et al., A cytotoxic agent can be generated selectively at cancer sites. Br J Cancer. Dec. 1988;58(6):700-3.

Bagshawe, Antibody directed enzymes revive anti-cancer prodrugs concept. Br J Cancer. Nov. 1987;56(5):531-2.

Bischoff et al., An adenovirus mutant that replicates selectively in p53-deficient human tumor cells. Science. Oct. 18, 1996;274(5286):373-6.

Bohl et al., Control of erythropoietin delivery by doxycycline in mice after intramuscular injection of adeno-associated vector. Blood. Sep. 1, 1998;92(5):1512-7.

Brown, Keynote address: hypoxic cell radiosensitizers: where next? Int J Radiat Oncol Biol Phys. Apr. 1989;16(4):987-93.

Brown, Sensitizers and protectors in radiotherapy. Cancer. May 1, 1985;55(9 Suppl):2222-8.

Brummelkamp et al., A system for stable expression of short interfering RNAs in mammalian cells. Science. Apr. 19, 2002;296(5567):550-3. Epub Mar. 21, 2002.

Burrows et al., Eradication of large solid tumors in mice with an immunotoxin directed against tumor vasculature. Proc Natl Acad Sci U S A. Oct. 1, 1993;90(19):8996-9000.

Byrne et al., Multiplex gene regulation: a two-tiered approach to transgene regulation in transgenic mice. Proc Natl Acad Sci U S A. Jul. 1989;86(14):5473-7.

Chin et al., In-vivo optical detection of cancer using chlorin e6—polyvinylpyrrolidone induced fluorescence imaging and spectroscopy. BMC Med Imaging. Jan. 8, 2009;9:1.

Collins et al., Cosmix-plexing: a novel recombinatorial approach for evolutionary selection from combinatorial libraries. J Biotechnol. Jun. 2001;74(4):317-38.

Cotten et al., High-efficiency receptor-mediated delivery of small and large (48 kilobase gene constructs using the endosome-disruption activity of defective or chemically inactivated adenovirus particles. Proc Natl Acad Sci U S A. Jul. 1, 1992;89(13):6094-8.

Culver et al., In vivo gene transfer with retroviral vector-producer cells for treatment of experimental brain tumors. Science. Jun. 12, 1992;256(5063):1550-2.

Curiel, Adenovirus facilitation of molecular conjugate-mediated gene transfer. Prog Med Virol. 1993;40:1-18.

Daniels et al., A tenascin-C aptamer identified by tumor cell SELEX: systematic evolution of ligands by exponential enrichment. Proc Natl Acad Sci U S A. Dec. 23, 2003;100(26):15416-21. Epub Dec. 15, 2003.

Dougherty et al., Photodynamic therapy. J Natl Cancer Inst. Jun. 17, 1998;90(12):889-905.

Elbashir et al., Duplexes of 21-nucleotide RNAs mediate RNA interference in cultured mammalian cells. Nature. May 24, 2001;411(6836):494-8.

Ellington et al., Selection in vitro of single-stranded DNA molecules that fold into specific ligand-binding structures. Nature. Feb. 27, 1992;355(6363):850-2.

Fivash et al., BIAcore for macromolecular interaction. Curr Opin Biotechnol. Feb. 1998;9(1):97-101.

Frank, The SPOT-synthesis technique. Synthetic peptide arrays on membrane supports—principles and applications. J Immunol Methods. Sep. 1, 2002;267(1):13-26.

Frankel et al., Antisense oligonucleotide-induced inhibition of adrenocorticotropic hormone release from cultured human corticotrophs. J Neurosurg. Aug. 1999;91(2):261-7.

Gartner et al., DNA-templated organic synthesis and selection of a library of macrocycles. Science. Sep. 10, 2004;305(5690):1601-5. Epub Aug. 19, 2004.

Giovannoni et al., Isolation of anti-angiogenesis antibodies from a large combinatorial repertoire by colony filter screening. Nucleic Acids Res. Mar. 1, 2001;29(5):E27.

Goodchild et al., Inhibition of human immunodeficiency virus replication by antisense oligodeoxynucleotides. Proc Natl Acad Sci U S A. Aug. 1988;85(15):5507-11. Erratum in: Proc Natl Acad Sci U S A Mar. 1989;86(5):1504.

Griffiths et al., Isolation of high affinity human antibodies directly from large synthetic repertoires. EMBO J. Jul. 15, 1994;13(14):3245-60.

Hannon, RNA interference. Nature. Jul. 11, 2002;418(6894):244-51.

Helmling et al., Inhibition of ghrelin action in vitro and in vivo by an RNA-Spiegelmer. Proc Natl Acad Sci U S A. Sep. 7, 2004;101(36):13174-9. Epub Aug. 25, 2004.

Herbert et al., A novel method of differential gene expression analysis using multiple cDNA libraries applied to the identification of tumour endothelial genes. BMC Genomics. Apr. 7, 2008;9:153.

Ho et al., Identification of endothelial cell genes by combined database mining and microarray analysis. Physiol Genomics. May 13, 2003;13(3):249-62.

Hoogenboom et al., By-passing immunisation. Human antibodies from synthetic repertoires of germline VH gene segments rearranged in vitro. J Mol Biol. Sep. 20, 1992;227(2):381-8.

Horsman, Nicotinamide and other benzamide analogs as agents for overcoming hypoxic cell radiation resistance in tumours. A review. Acta Oncol. 1995;34(5):571-87.

Huang et al., Tumor infarction in mice by antibody-directed targeting of tissue factor to tumor vasculature. Science. Jan. 24, 1997;275(5299):547-50.

Huminiecki et al., In silico cloning of novel endothelial-specific genes. Genome Res. Nov. 2000;10(11):1796-806.

Iliakis et al., Application of non-hypoxic cell sensitizers in radiobiology and radiotherapy: rationale and future prospects. Int J Radiat Oncol Biol Phys. May 1989;16(5):1235-41.

Isalan et al., A rapid, generally applicable method to engineer zinc fingers illustrated by targeting the HIV-1 promoter. Nat Biotechnol. Jul. 2001;19(7):656-60.

Kettleborough et al., Humanization of a mouse monoclonal antibody by CDR-grafting: the importance of framework residues on loop conformation. Protein Eng. Oct. 1991;4(7):773-83.

Khodarev et al., Tumour-endothelium interactions in co-culture: coordinated changes of gene expression profiles and phenotypic properties of endothelial cells. J Cell Sci. Mar. 15, 2003;116(Pt 6):1013-22.

Köhler et al., Continuous cultures of fused cells secreting antibody of predefined specificity. Nature. Aug. 7, 1975;256(5517):495-7.

Kuriyama et al., A potential approach for gene therapy targeting hepatoma using a liver-specific romoter on a retroviral vector. Cell Struct Funct. Dec. 1991;16(6):503-10.

Ledley, Nonviral gene therapy: the promise of genes as pharmaceutical products. Hum Gene Ther. Sep. 1995;6(9):1129-44.

Magari et al., Pharmacologic control of a humanized gene therapy system implanted into nude mice. J Clin Invest. Dec. 1, 1997;100(11):2865-72.

Malmqvist, An affinity biosensor system for characterization of biomolecular interactions. Biochem Soc Trans. Feb. 1999;27(2):335-40.

McCafferty et al., Phage antibodies: filamentous phage displaying antibody variable domains. Nature. Dec. 6, 1990;348(6301):552-4.

McGinn et al., Radiosensitizing nucleosides. J Natl Cancer Inst. Sep. 4, 1996;88(17):1193-203.

Melkko et al., Encoded self-assembling chemical libraries. Nat Biotechnol. May 2004;22(5):568-74. Epub Apr. 18, 2004.

Melo et al., Gene and cell-based therapies for heart disease. FASEB J. Apr. 2004;18(6):648-63.

Miller et al., Targeted vectors for gene therapy. FASEB J. Feb. 1995;9(2):190-9.

(56) References Cited

OTHER PUBLICATIONS

Morii et al., Structure and chromosome assignment of human S100 alpha and beta subunit genes. Biochem Biophys Res Commun Feb. 28, 1991;175(1):185-91. Erratum in: Biochem Biophys Res Commun Jun. 14, 1991;177(2):894.

Muckenschnabel et al., SpeedScreen: label-free liquid chromatography-mass spectrometry-based high-throughput screening for the discovery of orphan protein ligands. Anal Biochem. Jan. 15, 2004;324(2):241-9.

Mura et al., Low shear stress induces the novel tumor endothelial marker CLEC14A that mediates cell migration and vascular development. Proceedings of the American Association for Cancer Research Annual Meeting. Apr. 17-21, 2010;51:382. 3 pgs. Abstract.

Nässander et al., In vivo targeting of OV-TL 3 immunoliposomes to ascitic ovarian carcinoma cells (OVCAR-3) in athymic nude mice. Cancer Res. Feb. 1, 1992;52(3):646-53.

Neri et al., Tumour vascular targeting. Nat Rev Cancer. Jun. 2005;5(6):436-46.

Oliva et al., Complete structure of the human gene encoding neuron-specific enolase. Genomics. May 1991;10(1):157-65.

Pinilla et al., Advances in the use of synthetic combinatorial chemistry: mixture-based libraries. Nat Med. Jan. 2003;9(1):118-22.

Primus et al., Bispecific antibody mediated targeting of nidocarboranes to human colon carcinoma cells. Bioconjug Chem. Sep.-Oct. 1996;7(5):532-5.

Ran et al., Infarction of solid Hodgkin's tumors in mice by antibody-directed targeting of tissue factor to tumor vasculature. Cancer Res. Oct. 15, 1998;58(20):4646-53.

Rippmann et al., Fusion of the tissue factor extracellular domain to a tumour stroma specific single-chain fragment variable antibody results in an antigen-specific coagulation-promoting molecule. Biochem J. Aug. 1, 2000;349 Pt 3:805-12.

Rivera et al., Long-term regulated expression of growth hormone in mice after intramuscular gene transfer. Proc Natl Acad Sci U S A. Jul. 20, 1999;96(15):8657-62.

Rogaev et al., An informative microsatellite repeat polymorphism in the human neurofilament light polypeptide (NEFL) gene. Hum Mol Genet. Dec. 1992;1(9):781.

Schaffitzel et al., Ribosome display: an in vitro method for selection and evolution of antibodies from libraries. J Immunol Methods. Dec. 10, 1999;231(1-2):119-35.

Scott et al., Searching for peptide ligands with an epitope library. Science. Jul. 7, 1990;249(4967):386-90.

Seaman et al., Genes that distinguish physiological and pathological angiogenesis. Cancer Cell. Jun. 2007;11(6):539-54.

Senter et al., Anti-tumor effects of antibody-alkaline phosphatase conjugates in combination with etoposide phosphate. Proc Natl Acad Sci U S A. Jul. 1988;85(13):4842-6.

Sharif et al., Current status of catheter- and stent-based gene therapy. Cardiovasc Res. Nov. 1, 2004;64(2):208-16.

Shi et al., Evidence of human thrombomodulin domain as a novel angiogenic factor. Circulation. Apr. 5, 2005;111(13):1627-36. Epub Mar. 28, 2005.

Shuker et al., Discovering high-affinity ligands for proteins: Sar by Nmr. Science. Nov. 29, 1996;274(5292):1531-4.

Soderlind et al., Recombining germline-derived CDR sequences for creating diverse single-framework antibody libraries. Nat Biotechnol. Aug. 2000;18(8):852-6.

Soderlind et al., The immune diversity in a test tube—non-immunised antibody libraries and functional variability in defined protein scaffolds. Comb Chem High Throughput Screen. Aug. 2001;4(5):409-16.

St Croix et al., Genes expressed in human tumor endothelium. Science. Aug. 8, 2000;289(5482):1197-202.

Sui et al., A DNA vector-based RNAi technology to suppress gene expression in mammalian cells. Proc Natl Acad Sci U S A. Apr. 16, 2002;99(8):5515-20.

Svensson et al., Efficient and stable transduction of cardiomyocytes after intramyocardial injection or intracoronary perfusion with recombinant adeno-associated virus vectors. Circulation. Jan. 19, 1999;99(2):201-5.

Terskikh et al., "Peptabody": a new type of high avidity binding protein. Proc Natl Acad Sci U S A. Mar. 4, 1997;94(5):1663-8.

Thisse et al., High-resolution in situ hybridization to whole-mount zebrafish embryos. Nat Protoc. 2008;3(1):59-69. doi: 10.1038/nprot.2007.514.

Thompson et al., Clustal W: improving the sensitivity of progressive multiple sequence alignment through sequence weighting, position-specific gap penalties and weight matrix choice. Nucleic Acids Res. Nov. 11, 1994;22(22):4673-80.

Urnov et al., Designed transcription factors as tools for therapeutics and functional genomics. Biochem Pharmacol. Sep. 2002;64(5-6):919-23.

Van Den Hoff et al., cDNA sequence of the long mRNA for human glutamine synthase. Biochim Biophys Acta. Oct. 8, 1991;1090(2):249-51.

Vaughan et al., Human antibodies by design. Nat Biotechnol. Jun. 1998;16(6):535-9.

Verhoeyen et al., Reshaping human antibodies: grafting an antilysozyme activity. Science. Mar. 25, 1988;239(4847):1534-6.

Wagner et al., Transferrin-polycation conjugates as carriers for DNA uptake into cells. Proc Natl Acad Sci U S A. May 1990;87(9):3410-4.

Wallgard et al., Identification of a core set of 58 gene transcripts with broad and specific expression in the microvasculature. Arterioscler Thromb Vasc Biol. Aug. 2008;28(8):1469-76. doi: 0.1161/ATVBAHA.108.165738. Epub May 15, 2008.

Winter et al., Making antibodies by phage display technology. Annu Rev Immunol. 1994;12:433-55.

Witters et al., Antisense oligonucleotides to the epidermal growth factor receptor. Breast Cancer Res Treat. Jan. 1999;53(1):41-50.

Wrighton et al., Increased potency of an erythropoietin peptide mimetic through covalent imerization. Nat Biotechnol. Nov. 1997;15(12):1261-5.

\* cited by examiner

FIGURE 1A

CLEC14A POLYPEPTIDE SEQUENCE (SEQ ID NO: 1)

```
  1  MRPAFALCLL  WQALWPGPGG  GEHPTADRAG  CSASGACYSL  HHATMKRQAA  EEACILRGGA
 61  LSTVRAGAEL  RAVLALLRAG  PGPGGGSKDL  LFWVALERRR  SHCTLENEPL  RGFSWLSSDP
121  GGLESDTLQW  VEEPQRSCTA  RRCAVLQATG  GVEPAGWKEM  RCHLRANGYL  CKYQFEVLCP
181  APRPGAASNL  SYRAPFQLHS  AALDFSPPGT  EVSALCRGQL  PISVTCIADE  IGARWDKLSG
241  DVLCPCPGRY  LRAGKCAELP  NCLDDLGGFA  CECATGFELG  KDGRSCVTSG  EGQPTLGGTG
301  VPTRRPPATA  TSPVPQRTWP  IRVDEKLGET  PLVPEQDNSV  TSIPEIPRWG  SQSTMSTLQM
361  SLQAESKATI  TPSGSVISKF  NSTTSSATPQ  AFDSSSAVVF  IFVSTAVVVL  VILTMTVLGL
421  VKLCFHESPS  SQPRKESMGP  PGLESDPEPA  ALGSSSAHCT  NNGVKVGDCD  LRDRAEGALL
481  AESPLGSSDA
```

FIGURE 1B

CLEC14A cDNA SEQUENCE (SEQ ID NO: 2)

```
   1  CTCCTCTTGC  TCTAAGCAGG  GTGTTTGACC  TTCTAGTCGA  CTGCGTCCCC  TGTACCCGGC
  61  GCCAGCTGTG  TTCCTGACCC  CAGAATAACT  CAGGGCTGCA  CCGGGCCTGG  CAGCGCTCCG
 121  CACACATTTC  CTGTCGCGGC  CTAAGGGAAA  CTGTTGGCCG  CTGGGCCCGC  GGGGGGATTC
 181  TTGGCAGTTG  GGGGGTCCGT  CGGGAGCGAG  GGCGGAGGGG  AAGGGAGGGG  GAACCGGGTT
 241  GGGGAAGCCA  GCTGTAGAGG  GCGGTGACCG  CGCTCCAGAC  ACAGCTCTGC  GTCCTCGAGC
 301  GGGACAGATC  CAAGTTGGGA  GCAGCTCTGC  GTGCGGGGCC  TCAGAGAATG  AGGCCGGCGT
 361  TCGCCCTGTG  CCTCCTCTGG  CAGGCGCTCT  GGCCCGGGCC  GGGCGGCGGC  GAACACCCCA
 421  CTGCCGACCG  TGCTGGCTGC  TCGGCCTCGG  GGGCCTGCTA  CAGCCTGCAC  CACGCTACCA
 481  TGAAGCGGCA  GGCGGCCGAG  GAGGCCTGCA  TCCTGCGAGG  TGGGGCGCTC  AGCACCGTGC
 541  GTGCGGGCGC  CGAGCTGCGC  GCTGTGCTCG  CGCTCCTGCG  GGCAGGCCCA  GGGCCCGGAG
 601  GGGGCTCCAA  AGACCTGCTG  TTCTGGGTCG  CACTGGAGCG  CAGGCGTTCC  CACTGCACCC
 661  TGGAGAACGA  GCCTTTGCGG  GGTTTCTCCT  GGCTGTCCTC  CGACCCCGGC  GGTCTCGAAA
 721  GCGACACGCT  GCAGTGGGTG  GAGGAGCCCC  AACGCTCCTG  CACCGCGCGG  AGATGCGCGG
 781  TACTCCAGGC  CACCGGTGGG  GTCGAGCCCG  CAGGCTGGAA  GGAGATGCGA  TGCCACCTGC
 841  GCGCCAACGG  CTACCTGTGC  AAGTACCAGT  TTGAGGTCTT  GTGTCCTGCG  CCGCGCCCCG
 901  GGGCCGCCTC  TAACTTGAGC  TATCGCGCGC  CCTTCCAGCT  GCACAGCGCC  GCTCTGGACT
 961  TCAGTCCACC  TGGGACCGAG  GTGAGTGCGC  TCTGCCGGGG  ACAGCTCCCG  ATCTCAGTTA
1021  CTTGCATCGC  GGACGAAATC  GGCGCTCGCT  GGGACAAACT  CTCGGGCGAT  GTGTTGTGTC
1081  CCTGCCCCGG  GAGGTACCTC  CGTGCTGGCA  AATGCGCAGA  GCTCCCTAAC  TGCCTAGACG
1141  ACTTGGGAGG  CTTTGCCTGC  GAATGTGCTA  CGGGCTTCGA  GCTGGGGAAG  GACGGCCGCT
1201  CTTGTGTGAC  CAGTGGGGAA  GGACAGCCGA  CCCTTGGGGG  GACCGGGGTG  CCCACCAGGC
1261  GCCCGCCGGC  CACTGCAACC  AGCCCCGTGC  CGCAGAGAAC  ATGGCCAATC  AGGGTCGACG
1321  AGAAGCTGGG  AGAGACACCA  CTTGTCCCTG  AACAAGACAA  TTCAGTAACA  TCTATTCCTG
```

FIGURE 1B (continued)

```
1381 AGATTCCTCG ATGGGGATCA CAGAGCACGA TGTCTACCCT TCAAATGTCC CTTCAAGCCG
1441 AGTCAAAGGC CACTATCACC CCATCAGGGA GCGTGATTTC AAGTTTAAT TCTACGACTT
1501 CCTCTGCCAC TCCTCAGGCT TTCGACTCCT CCTCTGCCGT GGTCTTCATA TTTGTGAGCA
1561 CAGCAGTAGT AGTGTTGGTG ATCTTGACCA TGACAGTACT GGGCTTGTC AAGCTCTGCT
1621 TTCACGAAAG CCCCTCTTCC CAGCCAAGGA AGGAGTCTAT GGGCCCGCCG GGCCTGGAGA
1681 GTGATCCTGA GCCCGCTGCT TTGGGCTCCA GTTCTGCACA TTGCACAAAC AATGGGGTGA
1741 AAGTCGGGGA CTGTGATCTG CGGGACAGAG CAGAGGGTGC CTTGCTGGCG GAGTCCCCTC
1801 TTGGCTCTAG TGATGCATAG GGAAACAGGG GACATGGGCA CTCCTGTGAA CAGTTTTTCA
1861 CTTTTGATGA AACGGGCAAC CAAGAGGAAC TTACTTGTGT AACTGACAAT TCTGCAGAA
1921 ATCCCCCTTC CTCTAAATTC CCTTTACTCC ACTGAGGAGC TAAATCAGAA CTGCACACTC
1981 CTTCCCTGAT GATAGAGGAA GTGGAAGTGC CTTTAGGATG GTGATACTGG GGGACCGGGT
2041 AGTGCTGGGG AGAGATATTT TCTTATGTTT ATTCGGAGAA TTTGGAGAAG TGATTGAACT
2101 TTTCAAGACA TTGGAAACAA ATAGAACACA ATATAATTTA CATTAAAAAA TAATTTCTAC
2161 CAAAATGGAA AGGAAATGTT CTATGTTGTT CAGGCTAGGA GTATATTGGT TCGAAATCCC
2221 AGGGAAAAAA ATAAAAATAA AAAATTAAAG GATTGT
```

FIGURE 1C
CLEC14A CODING SEQUENCE (SEQ ID NO: 3)

```
ATGAGGCCGG CGTTCGCCCT GTGCCTCCTC TGGCAGGCGC TCTGGCCCGG GCCGGGCGGC    60
GGCGAACACC CCACTGCCGA CCGTGCTGGC TGCTCGGCCT CGGGGGCCTG CTACAGCCTG   120
CACCACGCTA CCATGAAGCG GCAGGCGGCC GAGGAGGCCT GCATCCTGCG AGGTGGGGCG   180
CTCAGCACCG TGCGTGCGGG CGCCGAGCTG CGCGCTGTGC TCGCGTCCT GCGGGCAGGC   240
CCAGGGCCCG GAGCGGGCTC CAAAGACCTG CTGTTCTGGG TCGCACTGGA GCGCAGGCGT   300
TCCCACTGCA CCCTGGAGAA CGAGCCTTTC CGGGGTTTCT CCTGGCTGTC CTCCGACCCC   360
GGCGGTCTCG AAAGCGACAC GCTGCAGTGG GTGGAGGAGC CCAACGCTC CTGCACCGCG   420
CGGAGATGCG CGGTACTCCA GGCCACCGGT GGGGTCGAGC CCGCAGGCTG AAGGAGATG   480
CGATGCCACC TGCGTGCCAA CGGCTACCTG TGCAAGTACC AGTTTGAGGT CTTTGTGTCCT   540
GCGCCGCGCC CGGGGCCGC CTCTAACTTC AGCTATGCG CGCCCTTCCA GCTGCACAGC   600
GCCGCTCTGG ACTTCAGTCC ACCTGGGACC GAGGTGAGTG CGCTCTGCCG GGACAGCTC   660
CCGATCTCAG TTACTTGCAT CGCGGACGAA ATCGCGCTC GCTGGACAA ACTCTCGGGC   720
GATGTGTTGT GTCCCTGCCC CGGGAGGTAC CTCCGTGCTG GCAAATGCGC AGAGCTCCCT   780
AACTGCCTAG ACGACTTGGG AGGCTTTGCC TGCGAATGTG CTACGGGCTT CGAGCTGGGG   840
AAGGACGGCC GCTCTTGTGT GACCAGTGGG GAAGGACAGC CGACCCTTGG GGGGACCGGG   900
GTGCCCACCA GCGCCCGCC GGCCACTGCA ACCAGCCCCG TGCCGCAGAG AACATGGCCA   960
ATCAGGGTCG ACGAGAAGCT GGGAGAGACA CCACTTGTCC CTGAACAAGA CAATTCAGTA  1020
ACATCTATTC CTGAGATTCC TCGATGGGGA TCACAGAGCA CGATGTCTAC CCTTCAAATG  1080
TCCCTTCAAG CCGAGTCAAA GGCCACTATC ACCCCATCAG GGAGCGTGAT TTCAAGTTT  1140
AATTCTACGA CTTCCTCTGC CACTCCTCAG GCTTTCGACT CCTCCTCTGC CGTGGTCTTC  1200
ATATTTGTGA GCACAGCAGT AGTAGTGTTG GTGATCTTGA CCATGACAGT ACTGGGCTT  1260
```

FIGURE 1C (continued)

```
GTCAAGCTCT GCTTTCACGA AAGCCCCTCT TCCCAGCCAA GGAAGGAGTC TATGGGCCCG 1320
CCGGGCCTGG AGAGTGATCC TGAGCCCGCT GCTTTGGGCT CCAGTTCTGC ACATTGCACA 1380
AACAATGGGG TGAAAGTCGG GGACTGTGAT CTGCGGGACA GAGCAGAGGG TGCCTTGCTG 1440
GCGGAGTCCC CTCTTGGCTC TAGTGATGCA TAG
```

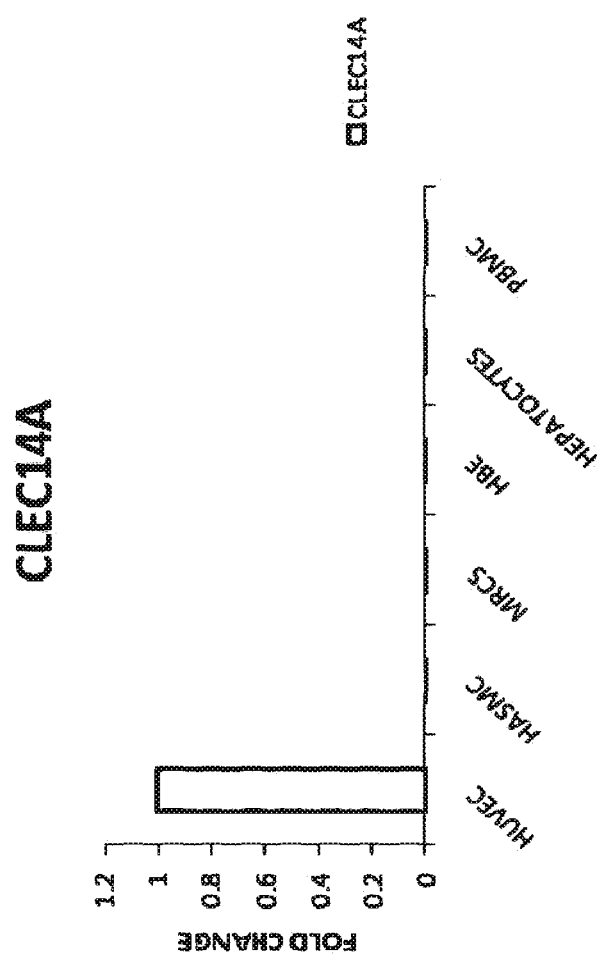

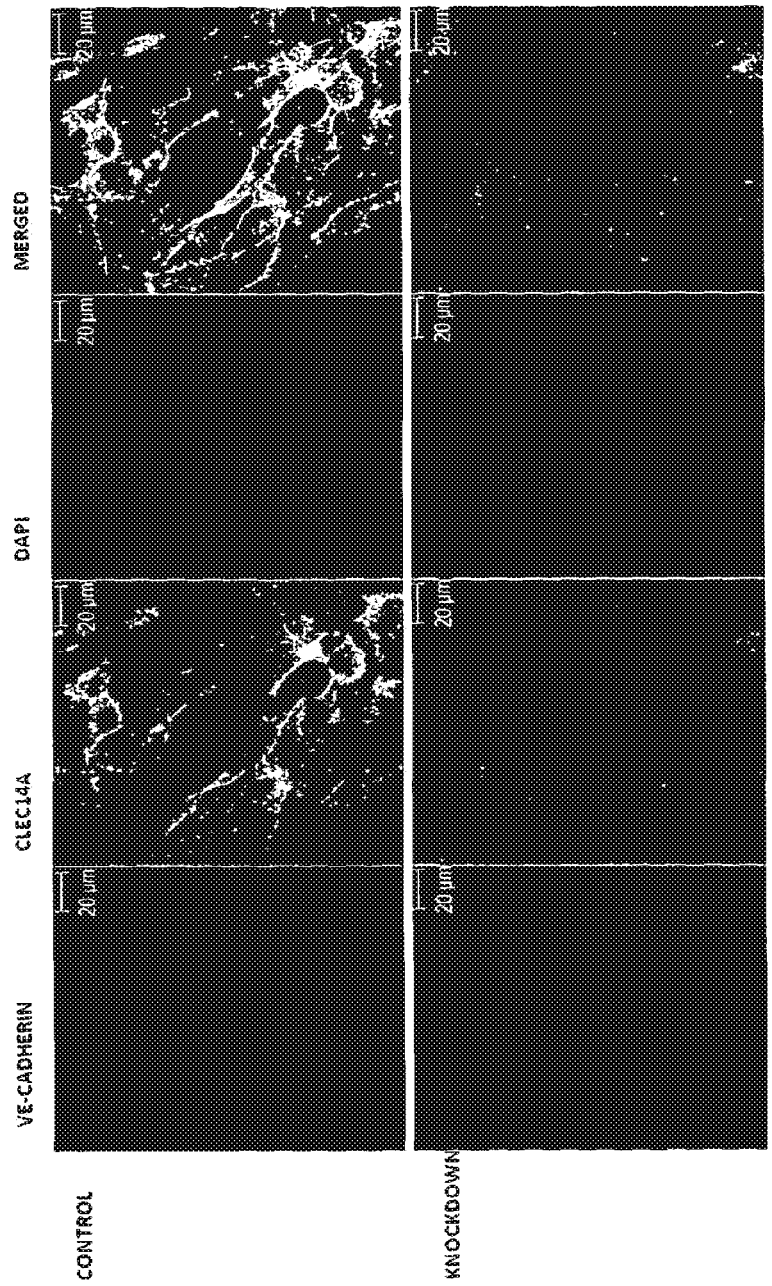

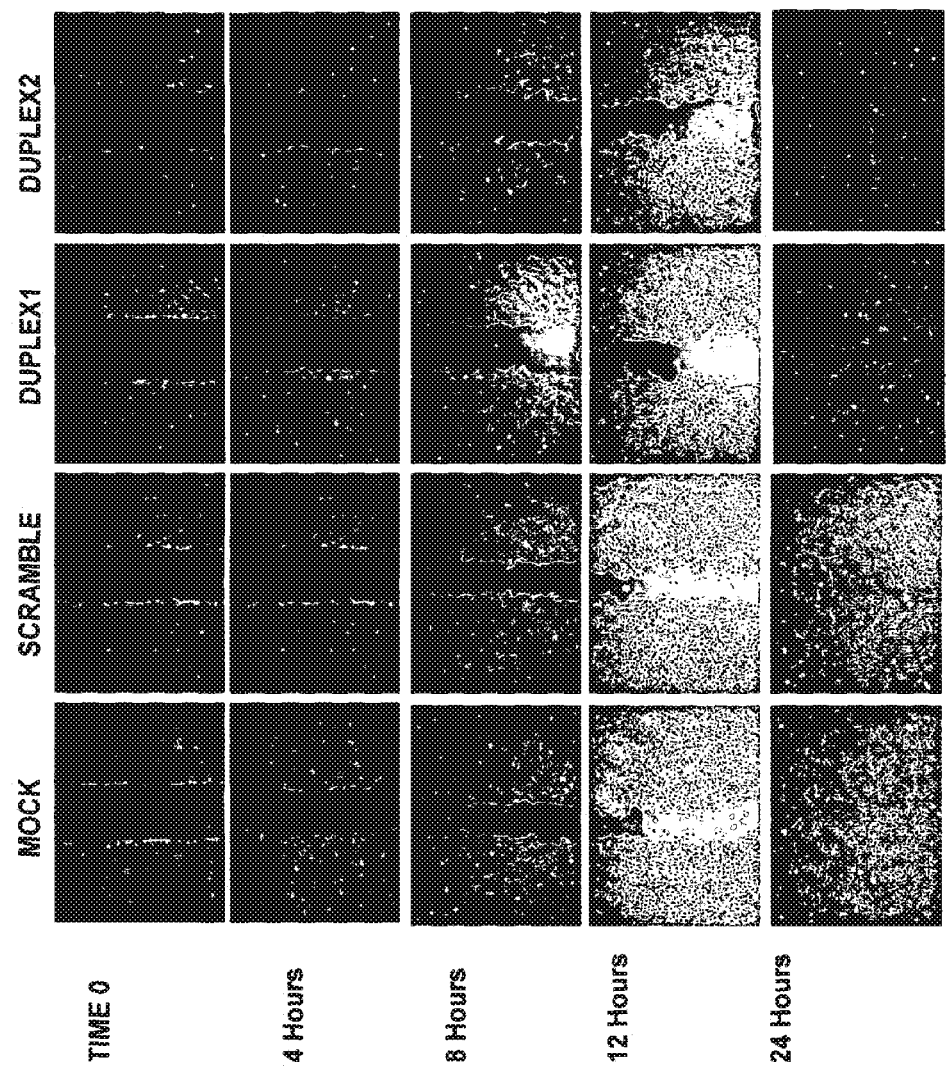

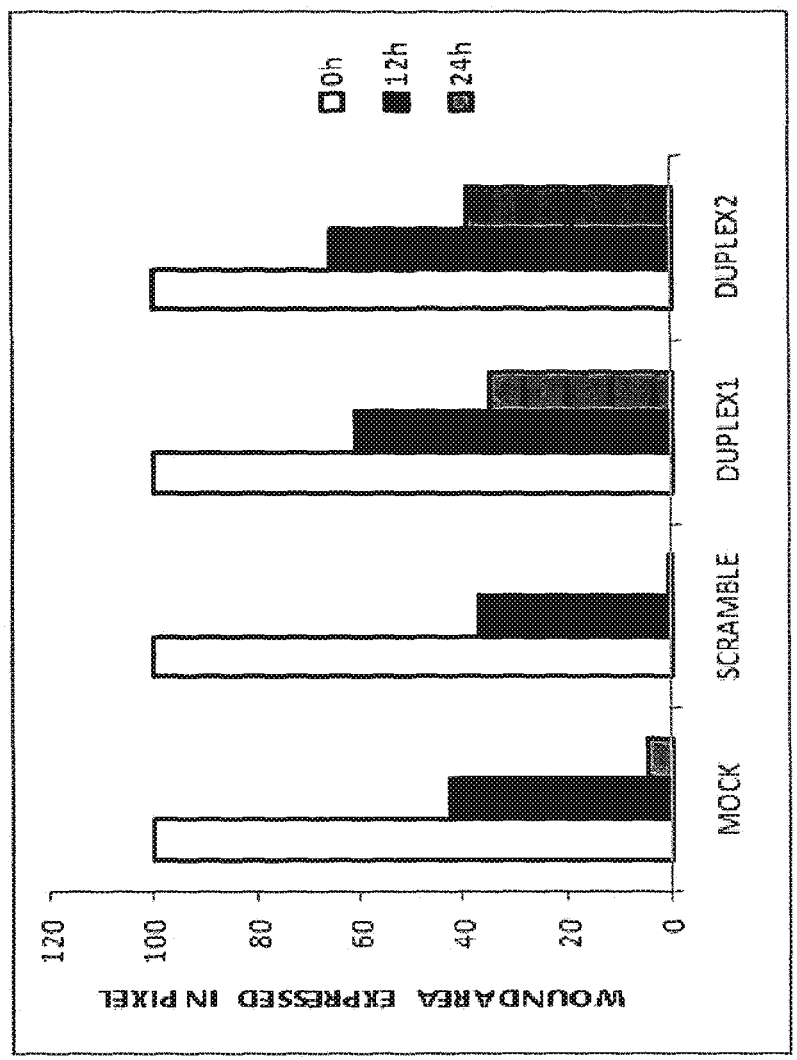

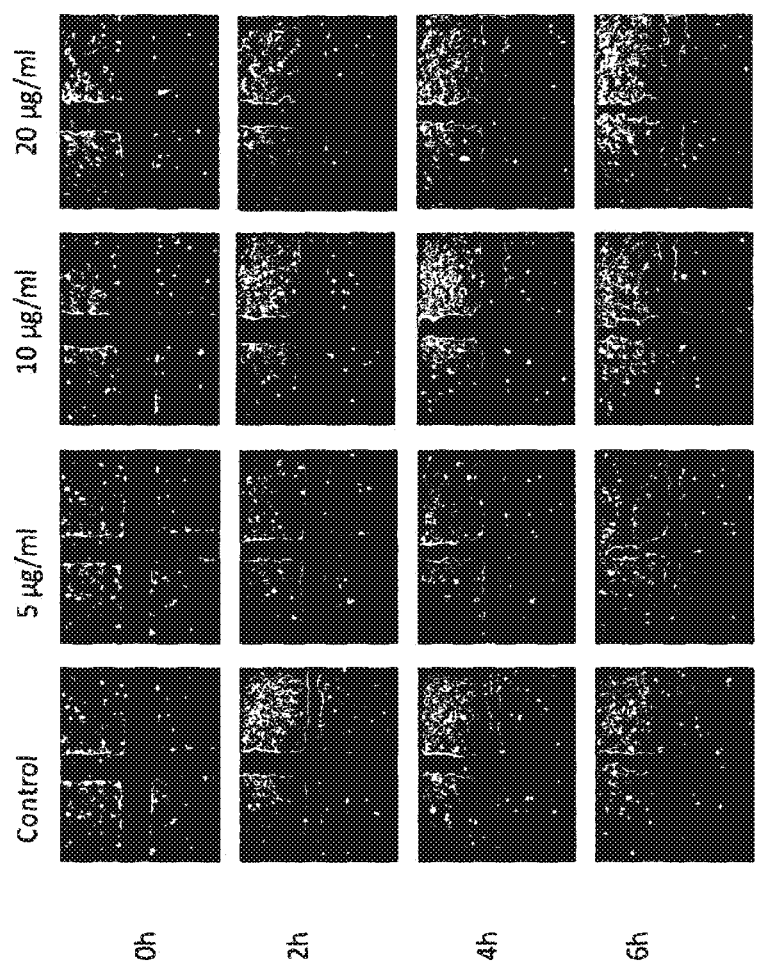

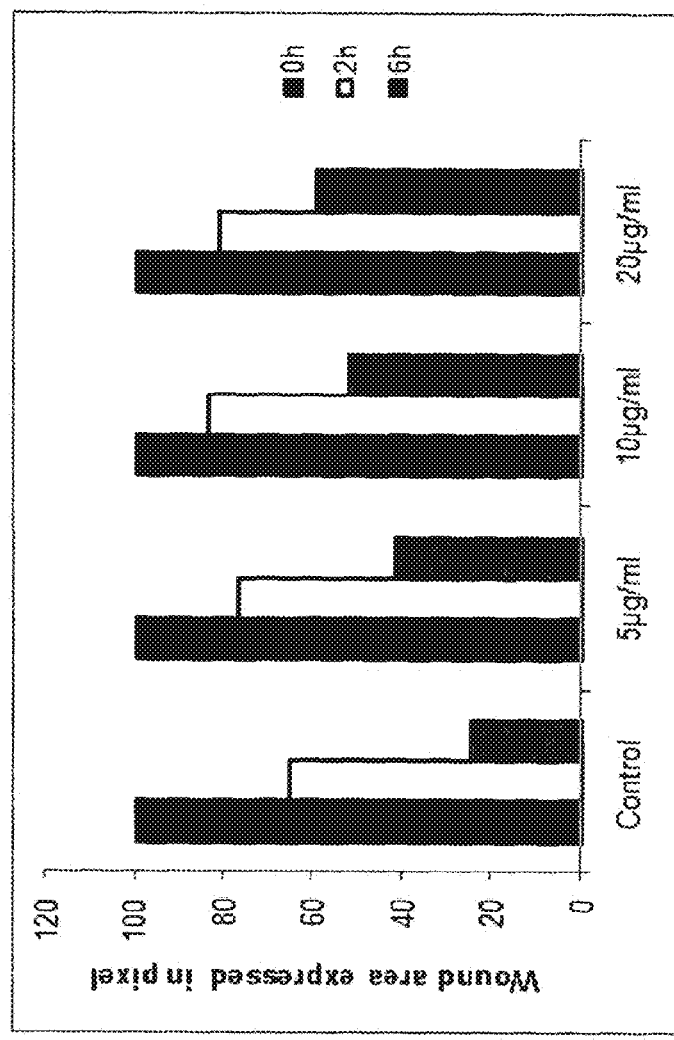

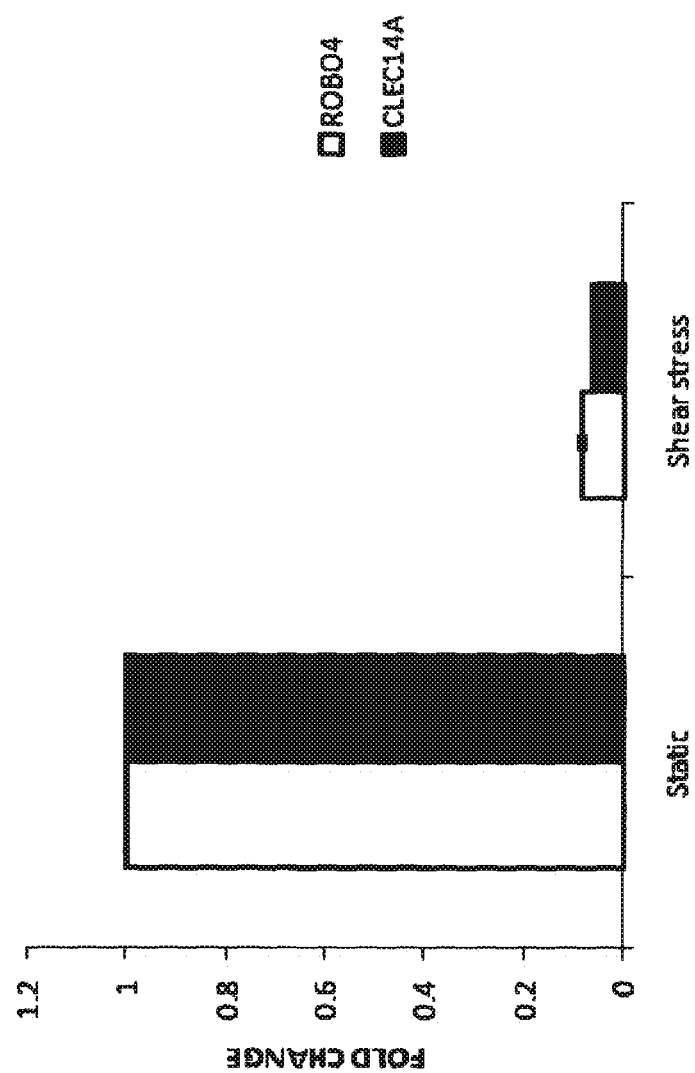

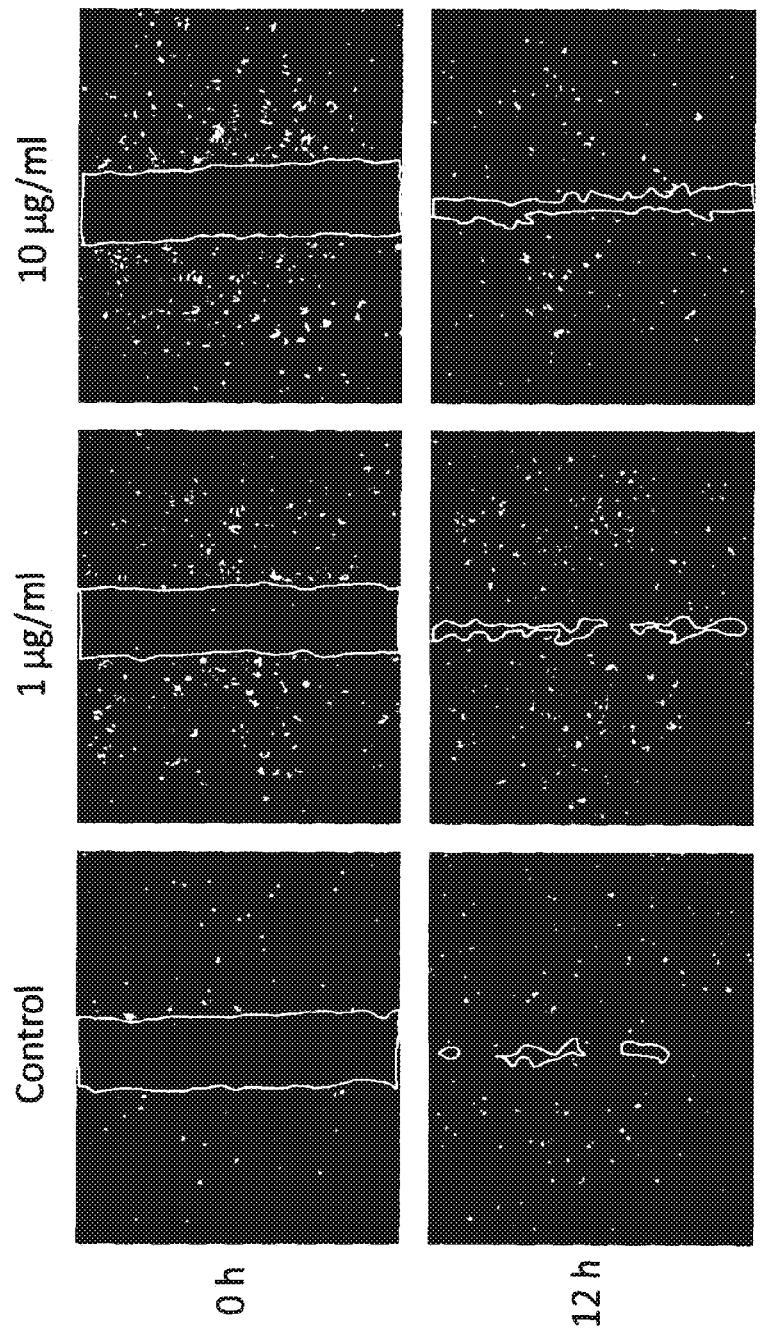

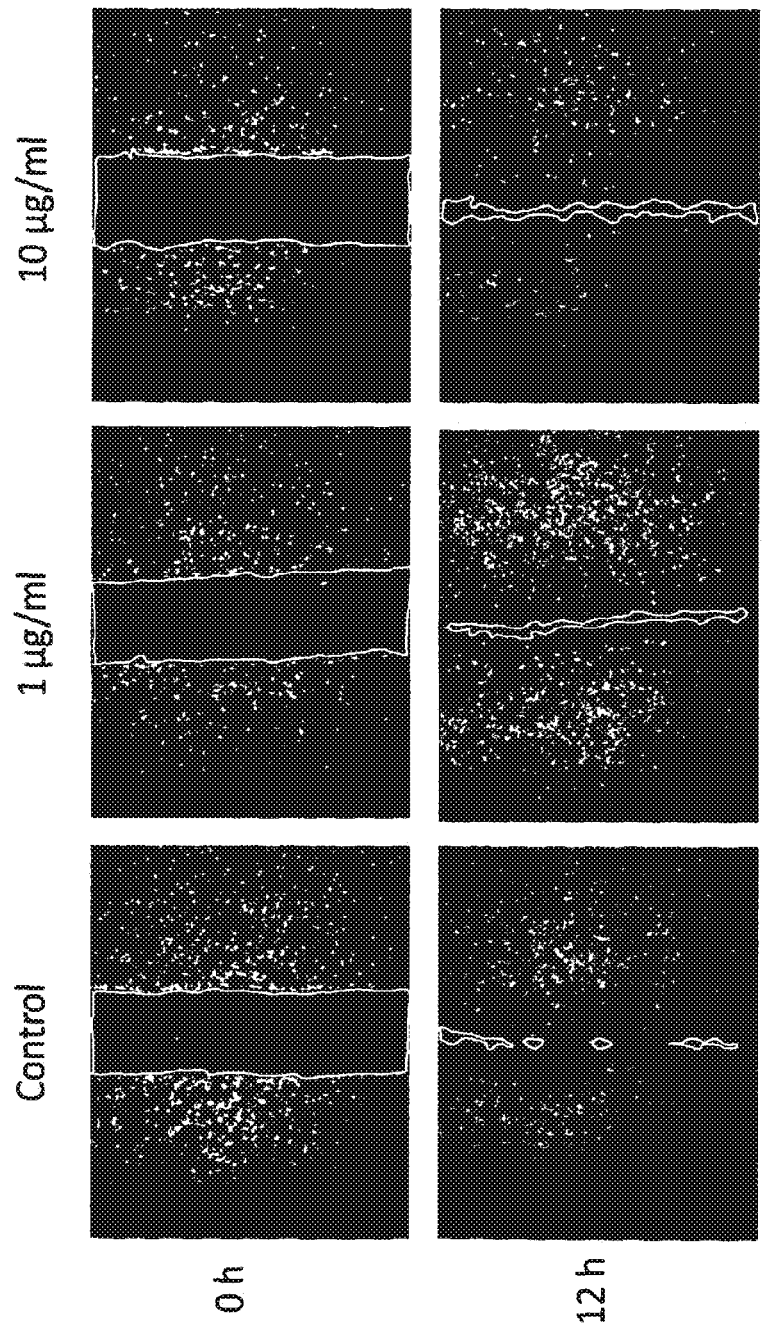

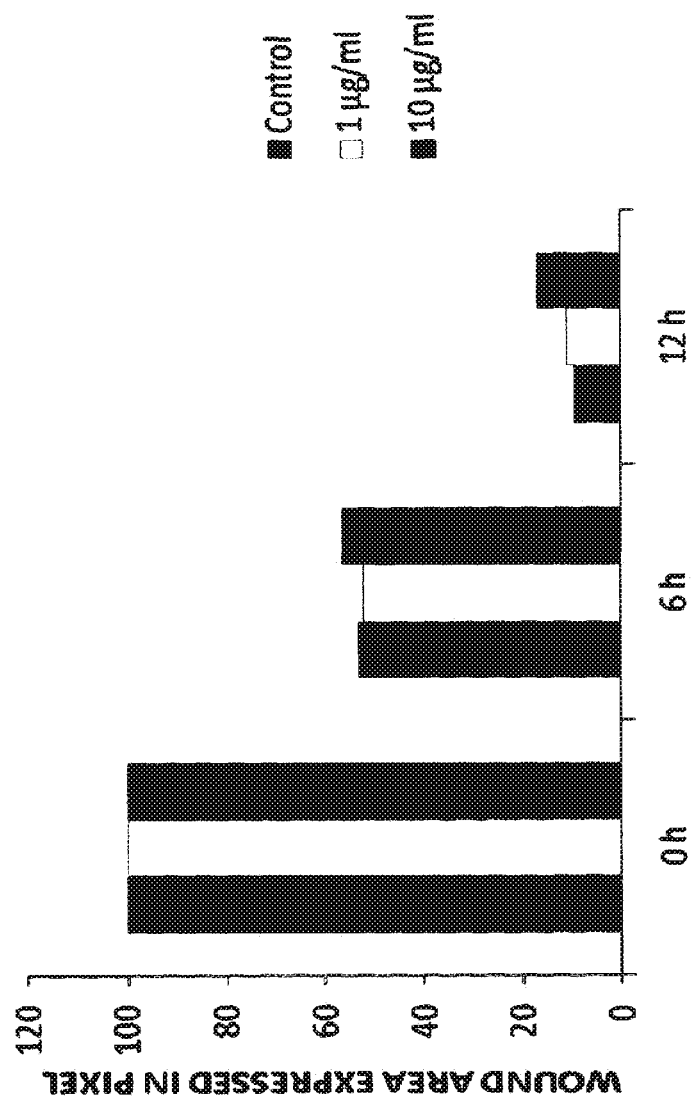

CLEC14A INHIBITORS

This application is a national stage filing under 35 U.S.C. §371 of international application PCT/GB2010/001689, filed Sep. 3, 2010, which was published under PCT Article 21(2) in English, and claims the benefit under 35 U.S.C. §119(e) of U.S. Provisional Application Ser. No. U.S. 61/239,584, entitled "INHIBITORS," filed on Sep. 3, 2009, the disclosure of each of which is herein incorporated by reference in its entirety.

The present invention relates generally to tumour endothelium specific genes and polypeptides, to the use of antibodies that bind these polypeptides for imaging and targeting tumour vasculature, and to the use of inhibitors of these tumour endothelium specific genes/polypeptides for inhibiting angiogenesis in solid tumours. In particular, the present invention relates to CLEC14A, to the use of antibodies that bind CLEC14A for imaging and targeting tumour neovasculature, and to the use of inhibitors of CLEC14A for inhibiting angiogenesis in solid tumours.

The endothelium plays a central role in many physiological and pathological processes and it is known to be an exceptionally active transcriptional site. Approximately 1,000 distinct genes are expressed in an endothelial cell, although many of them are not endothelial cell specific. In contrast red blood cells were found to express 8, platelets 22 and smooth muscle 127 separate genes (Adams et al (1995) *Nature* 377 (6547 Suppl): 3-174). Known endothelial specific genes attract much attention from both basic research and the clinical community. For example, the endothelial-specific tyrosine kinases Tie, TIE2/TEK, KDR, and flt1 are crucial players in the regulation of vascular integrity, endothelium-mediated inflammatory processes and angiogenesis.

We have previously used an in silico database screening approach to identify endothelial specific genes, and identified four new candidate endothelial specific genes, none of which were CLEC14A (Huminiecki & Bicknell (2000) "In silico cloning of novel endothelial-specific genes." *Genome Res.* 10: 1796-1806).

Ho et al used data mining and micro-array expression analysis to identify endothelial specific genes, and identified 64 genes that are either specific for endothelial cells or at least 3-fold preferentially expressed in endothelial cells, none of which were CLEC14A (Ho et al (2003) "Identification of endothelial cell genes by combined database mining and microarray analysis." *Physiol Genomics.* 13: 249-262).

Wallgard et al analysed publicly available micro-array expression data and identified a core set of 58 genes with broad, endothelial-specific expression in the microvasculature. This set includes most known and currently used endothelial markers, as well as genes that had not previously been linked to endothelial function, none of which were CLEC14A (Wallgard et al (2008) "Identification of a core set of 58 gene transcripts with broad and specific expression in the microvasculature." *Arterioscler. Thromb. Vasc. Biol.* 28: 1469-1476).

Endothelial cells form a single cell layer that lines all blood vessels and regulates exchanges between the blood stream and the surrounding tissues. New blood vessels develop from the walls of existing small vessels by the outgrowth of endothelial cells in the process called angiogenesis. Endothelial cells even have the capacity to form hollow capillary tubes when isolated in culture. Once the vascular system is fully developed, endothelial cells of blood vessels normally remain quiescent with no new vessel formation, with the exception of the formation of new blood vessels in natural wound healing.

However, some tumours attract a new blood supply by secreting factors that stimulate nearby endothelial cells to construct new capillary sprouts. Angiogenesis plays a major role in the progression of solid tumours and is widely recognised as a rate-limiting process in the growth of solid tumours. Tumours that fail to attract a blood supply are severely limited in their growth. Thus the ability to inhibit inappropriate or undesirable angiogenesis may be useful in the treatment of solid tumours.

The development of new blood vessels is essential for both local tumour progression and the development of distant metastases. Indeed, the growth and survival of tumours is dependent on their ability to obtain a blood supply and damage inflicted on the tumour endothelium has been shown to effectively eradicate tumours (Burrows et al (1993) "Eradication of large solid tumors in mice with an immunotoxin directed against tumor vasculature." *Proc Natl Acad Sci USA*, 90(19): 8996-9000). Tumour angiogenesis involves the degradation of the basement membrane by activated tissue or circulating endothelial precursors, proliferation and migration of endothelial cells, interaction with the extracellular matrix, morphological differentiation, cell adherence and vascular tube formation. Inhibition of tumour angiogenesis is thus a target for anti-tumour therapies, employing either angiogenesis inhibitors alone or in combination with standard cancer treatments. However, targeting anti-tumour agents to the site of angiogenesis depends upon the identification of specific markers of tumour angiogenesis. It is now accepted that the growth of solid tumours is dependent on their capacity to acquire a blood supply, and much effort has been directed towards the development of anti-angiogenic agents that disrupt this process. It has also become apparent that targeted destruction of the established tumour vasculature is another avenue for exciting therapeutic opportunities, and the discovery of widely expressed tumour endothelial markers promises much clinical benefit (Neri & Bicknell (2005) "Tumour vascular targeting." *Nat Rev Cancer* 5(6): 436-446).

These therapeutic approaches depend upon the identification of specific tumour endothelial markers (TEMs). In a screen for tumour-specific endothelial markers that might be candidates for anti-angiogenic tumour therapy, St Croix et al (2000) identified 79 genes that were differentially expressed between endothelial cells derived from tumour endothelium and normal colonic mucosa, none of which were CLEC14A (St Croix et al (2000) "Genes expressed in human tumor endothelium." *Science* 289: 1197-202). The expression of 33 of these genes was elevated at least 10-fold in tumour endothelial cells, including 11 known and 14 as-then uncharacterised genes. In situ hybridization on tissue samples confirmed that the expression of eight of the nine uncharacterised genes that were studied in depth were specific for tumour endothelial cells. Moreover, these genes were also expressed on endothelial cells of other tumours including lung and brain tumours. Except for one gene, these genes were also expressed at elevated levels in other angiogenic states such as healing wounds.

Khodarev et al (2003) modelled tumour/endothelial-cell interactions by co-culturing U87 human glioma cells with human umbilical vein endothelial cells (HUVECs). U87 cells induced an 'activated' phenotype in HUVECs, including an increase in proliferation, migration and net-like formation. Activation was observed in co-cultures where cells were either in direct contact or physically separated, suggesting an important role for soluble factor(s) in the phenotypic and genotypic changes observed. Expressional profiling of tumour-activated endothelial cells was evaluated using cDNA arrays and confirmed by quantitative PCR. Matching pairs of receptors/ligands were found to be coordinately expressed, including TGFβRII with TGFβ3, FGFRII and cysteine-rich fibroblast growth factor receptor (CRF-1) with FGF7 and FGF12, CCR1, CCR3, CCR5 with RANTES and calcitonin receptor-like gene (CALCRL) with adrenomedullin. CLEC14A was not identified. (Khodarev et al (2003) "Tumour-endothelium interactions in co-culture: coordinated changes of gene expression profiles and phenotypic properties of endothelial cells", *Journal of Cell Science* 116: 1013-1022.)

Seaman et al (2007) compared gene expression patterns of endothelial cells derived from the blood vessels of eight normal resting tissues, five tumours, and regenerating liver. Seaman et al identified organ-specific endothelial genes as well as 25 transcripts over-expressed in tumour versus normal endothelium, 13 of which were not found in the angiogenic endothelium of regenerating liver. CLEC14A was not identified. Most of the shared angiogenesis genes were expected to have roles in cell-cycle control, but those specific for tumour endothelium were primarily cell surface molecules of uncertain function (Seaman et al (2007) "Genes that distinguish physiological and pathological angiogenesis", *Cancer Cell.* 11(6): 539-54).

By data-mining public cDNA and SAGE libraries, we previously identified 459 predicted endothelial genes, one of which is CLEC14A. From these 459, we identified 27 genes/polypeptides (not including CLEC14A) whose expression is highly specific to the tumour endothelium (Herbert et al (2008) "A novel method of differential gene expression analysis using multiple cDNA libraries applied to the identification of tumour endothelial genes" *BMC Genomics* 9: 153 (doi:10.1186/1471-2164-9-153)). These genes/polypeptides were thus identified as novel tumour endothelial markers, which are particularly good anticancer drug targets as they can be targeted directly via the blood supply.

Nevertheless, there is a need in the art for additional Tumour Endothelial Markers (TEMs).

We have now identified a further gene/polypeptide, CLEC14A, which has a high degree of tumour endothelial specificity. We have shown that CLEC14A is expressed specifically in human endothelial cells, and in angiogenic tissues during development in a zebrafish model. We have also shown that the down-regulation of CLEC14A using siRNA technology and the inhibition of CLEC14A using anti-CLEC14A antibodies reduced endothelial cell migration, which is an essential component of angiogenesis. In addition, we have shown that CLEC14A expression is down-regulated in response to shear stress, which is often associated with down-regulation of pro-angiogenesis genes. By immunofluorescence we have also shown that CLEC14A is not expressed in normal adult tissues, but is expressed in neo-angiogenic vessels of cancers including colon, rectal, ovarian, liver, bladder, prostate, breast, kidney, pancreas, stomach, oesophagus, lung and thyroid cancer.

Accordingly, we conclude that CLEC14A genuinely encodes a TEM. Therefore, we now consider that the CLEC14A gene/polypeptide will be valuable as a marker of the tumour endothelium; that antibodies that selectively bind the CLEC14A polypeptide can be used to image and target the tumour neovasculature; and that inhibitors of the CLEC14A gene/polypeptide would be therapeutically useful in the inhibition of tumour neoangiogenesis in solid tumours.

To the best of our knowledge, an inhibitor of CLEC14A has never previously been suggested to be an inhibitor of angiogenesis.

WO 02/079492 (Eos Biotechnology, Inc) lists many hundreds of ESTs whose expression was said to vary over time in angiogenic tissue. One of these ESTs was an EST encoding a 166 residue fragment of CLEC14A (referred to therein as Pkey 105729, Accession No. Hs46612, Unigene No. Hs293815, Unigene Title HSPC285). However, WO 02/079492 provides no data on the expression of this EST during angiogenesis; it does not even state whether expression was supposed to have increased or decreased or whether it was restricted to tumour endothelial cells.

In Herbert et al (2008), we described a comprehensive set of 459 in silico predicted endothelial genes obtained by combining cDNA and SAGE library data. Although we identified CLEC14A as being preferentially expressed in endothelial cells (Additional File 13), it was not in the top 104 most endothelial specific genes. In this earlier report we did not identify CLEC14A as being specific for the tumour endothelium or being involved in angiogenesis. Indeed, no function for CLEC14A was known or proposed, and no further corroborative experiments were undertaken.

Genentech, Inc. has a number of published patents and patent applications relating to 'PRO' genes and polypeptides, of which PRO269 (Clone DNA38260-1180) is equivalent to CLEC14A. In these patents and applications, multiple potential roles have been ascribed to PRO269. For example, in both US 2003/0186358 and U.S. Pat. No. 6,894,148, PRO269 was said to have use as an antithrombotic agent due to its homology with thrombomodulin, and was said to have the ability to stimulate lymphocyte proliferation, to induce c-fos in cortical neurons, and to affect glucose uptake. Of greater relevance, PRO269 was found to be between 2-4-fold amplified in the genomic DNA of 8 lung tumour samples and cell lines (n=20), but not amplified in the genomic DNA from colon (n=19), testis (n=2) or kidney (n=1) tumour samples or cell lines. Similarly, in US 2003/0175900, PRO269 was found to be between 2-4-fold amplified in the genomic DNA of the same 8 lung tumour samples and cell lines (n=50), but not amplified in the genomic DNA from colon (n=45), breast (n=18), lymph node (n=3), kidney (n=2), parathyroid (n=2), rectum (n=2) or testis (n=2) tumour samples and cell lines.

In US 2003/0194775 (Genentech, Inc.) PRO269 was said to be over-expressed in lung and rectal tumours, but not in breast, colon, cervical, prostate or liver tumours, in comparison to a 'universal' epithelial control sample which was prepared by pooling non-cancerous human tissues of epithelial origin, including liver, kidney, and lung tissues.

By contrast, WO 03/101283 (Incyte Genomics, Inc) describes 170 transcripts whose expression was found to be differentially regulated in lung tumours. Of these, a transcript equivalent to CLEC14A (referred to therein as Incyte ID 2264002CB1, Genbank Accession No. g15209752) was found to be between 4-16-fold down-regulated in 21 of 39 distinct lung tumour samples. This appears to contradict the findings in US 2003/0194775 regarding CLEC14A expression in lung tumours.

Incyte Genomics, Inc has also suggested that CLEC14A was one of 34 human atherosclerosis-associated genes due to its co-expression with other known atherosclerotic genes (WO 01/04264).

Thus, despite the number of suggestions for possible functions and uses of CLEC14A, until the present invention, there has been no suggestion of its role as a tumour endothelial marker, or that an inhibitor of CLEC14A might be an inhibitor of tumour angiogenesis.

A first aspect of the invention thus provides a method of inhibiting tumour angiogenesis in an individual in need thereof, the method comprising administering to the individual an inhibitor of CLEC14A.

This aspect of the invention includes the use of an inhibitor of CLEC14A in the preparation of a medicament for inhibiting tumour angiogenesis in an individual. The invention further includes an inhibitor of CLEC14A for use in inhibiting tumour angiogenesis in an individual.

Typically, the individual has a solid tumour, which can be treated by inhibiting tumour angiogenesis, i.e. the solid tumour is associated with new blood vessel production. The term "tumour" is to be understood as referring to all forms of neoplastic cell growth, including, but not limited to, tumours of the breast, ovary, liver, bladder, prostate, kidney, pancreas, stomach, oesophagus, lung and thyroid.

Typically, the tumour is associated with undesirable neovasculature formation and the inhibitor of CLEC14A reduces this to a useful extent. The reduction of undesirable neovasculature formation may halt the progression of the tumour and can lead to a clinically useful reduction of tumour size and growth. Thus the inhibition of tumour angiogenesis can be used to treat the tumour, for example, to prevent the (further) growth of the tumour, to prevent the spread of the tumour (metastasis), or to reduce the size of the tumour.

We have shown that CLEC14A is specifically expressed in the vascular endothelium of a range of solid tumours including tumours of the colon, rectum, ovary, liver, bladder, prostate, breast, kidney, pancreas, stomach, oesophagus, lung and thyroid. Thus, in a preferred embodiment, the individual has a solid tumour selected from colon, rectal, ovarian, liver, bladder, prostate, breast, kidney, pancreas, stomach, oesophagus, lung and thyroid tumours.

In a specific embodiment, the individual has a solid tumour other than a lung cancer and/or a rectal cancer.

Preferably, the methods and medicaments of the invention are used to treat humans, in which case the inhibitor of CLEC14A is an inhibitor of human CLEC14A. It is appreciated, however, that when the methods and medicaments of the invention are for treatment of non-human mammals, it is preferred if the inhibitor is specific for the CLEC14A gene/polypeptide from the other species.

CLEC14A

The gene CLEC14A (C-type lectin domain family 14, member A), which is located at 14q21.1, was previously known as C14orf27, CEG1 and EGFR5. CLEC14A encodes a 490 amino acid residue polypeptide with a predicted MW of 51 kDa. By the CLEC14A polypeptide we include the meaning of a gene product of human CLEC14A, including naturally occurring variants thereof. Human CLEC14A polypeptide includes the amino acid sequence found in Genbank Accession No NP_778230 and naturally occurring variants thereof. The CLEC14A polypeptide sequence from NP_778230 is shown in FIG. 1 (SEQ ID NO: 1).

A cDNA sequence corresponding to a human CLEC14A mRNA is found in Genbank Accession No NM_175060 and shown in FIG. 1 (SEQ ID NO: 2). The coding region of this cDNA from NM_175060 is from nucleotide 348 to nucleotide 1820, and this is also shown in FIG. 1 (SEQ ID NO: 3).

CLEC14A is a type I transmembrane protein with a signal peptide at residues 1-21. The mature human polypeptide is 469 amino acids in length (amino acid residues 22-490), and contains a 375 residue extracellular region (residues 22-396), a transmembrane region (residues 397-425), and a cytoplasmic region (residues 426-490). The extracellular region contains a C-type lectin like domain (residues 32-175) and an EGF-like region (residues 245-287).

Inhibitors of CLEC14A

By an inhibitor of CLEC14A we include both inhibitors of the CLEC14A polypeptide and of the CLEC14A gene/cDNA.

Suitable inhibitors of CLEC14A include antibodies that selectively bind to CLEC14A. Other suitable inhibitors of CLEC14A include siRNA, antisense polynucleotides and ribozyme molecules that are specific for polynucleotides encoding the CLEC14A polypeptide, and which prevent its expression.

It is appreciated that polynucleotide inhibitors of CLEC14A may be administered directly, or may be administered in the form of a polynucleotide that encodes the inhibitor. Thus, as used herein, unless the context demands otherwise, by administering to the individual an inhibitor of CLEC14A which is a polynucleotide, we include the meanings of administering the inhibitor directly, or administering a polynucleotide that encodes the inhibitor, typically in the form of a vector. Similarly, as used herein, unless the context demands otherwise, by a medicament or a composition comprising an inhibitor of CLEC14A which is a polynucleotide, we include the meanings that the medicament or composition comprises the inhibitor itself, or comprises a polynucleotide that encodes the inhibitor.

Antibodies

Suitable antibodies which bind to CLEC14A, or to specified portions thereof, can be made by the skilled person using technology long-established in the art. Methods of preparation of monoclonal antibodies and antibody fragments are well known in the art and include hybridoma technology (Kohler & Milstein (1975) "Continuous cultures of fused cells secreting antibody of predefined specificity. *Nature* 256: 495-497); antibody phage display (Winter et al (1994) "Making antibodies by phage display technology." *Annu. Rev. Immunol.* 12: 433-455); ribosome display (Schaffitzel et al (1999) "Ribosome display: an in vitro method for selection and evolution of antibodies from libraries." *J. Immunol. Methods* 231: 119-135); and iterative colony filter screening (Giovannoni at al (2001) "Isolation of anti-angiogenesis antibodies from a large combinatorial repertoire by colony filter screening." *Nucleic Acids Res.* 29: E27). Further, antibodies and antibody fragments suitable for use in the present invention are described, for example, in the following publications: "*Monoclonal Hybridoma Antibodies: Techniques and Application*", Hurrell (CRC Press, 1982); "*Monoclonal Antibodies: A Manual of Techniques*", H. Zola, CRC Press, 1987, ISBN: 0-84936-476-0; "*Antibodies: A Laboratory Manual*" 1$^{st}$ Edition, Harlow & Lane, Eds, Cold Spring Harbor Laboratory Press, New York, 1988. ISBN 0-87969-314-2; "*Using Antibodies: A Laboratory Manual*" 2$^{nd}$ Edition, Harlow & Lane, Eds, Cold Spring Harbor Laboratory Press, New York, 1999. ISBN 0-87969-543-9; and "*Handbook of Therapeutic Antibodies*" Stefan Dübel, Ed., 1$^{st}$ Edition,—Wiley-VCH, Weinheim, 2007. ISBN: 3-527-31453-9.

Antibodies that are especially active at inhibiting tumour angiogenesis are preferred for anti-cancer therapeutic agents, and they can be selected for this activity using methods well known in the art and described below.

By an antibody that selectively binds the CLEC14A polypeptide we mean that the antibody molecule binds CLEC14A with a greater affinity than for an irrelevant polypeptide, such as human serum albumin (HSA). Preferably, the antibody binds the CLEC14A with at least 5, or at least 10 or at least 50 times greater affinity than for the irrelevant polypeptide. More preferably, the antibody molecule binds the CLEC14A with at least 100, or at least 1,000, or at least 10,000 times greater affinity than for the irrelevant polypeptide. Such binding may be determined by methods well known in the art, such as one of the Biacore® systems.

It is preferred that the antibody that selectively binds the CLEC14A polypeptide does not bind a related polypeptide, such as thrombomodulin, or that the antibody molecule binds CLEC14A with a greater affinity than for the related polypeptide such as thrombomodulin. Preferably, the antibody binds the CLEC14A with at least 5, or at least 10 or at least 50 times greater affinity than for the related polypeptide. More preferably, the antibody molecule binds the CLEC14A with at least 100, or at least 1,000, or at least 10,000 times greater affinity than for the related polypeptide. Such binding may be determined by methods well known in the art, such as one of the Biacore® systems.

It is preferred if the antibodies have an affinity for CLEC14A of at least $10^{-7}$ M and more preferably $10^{-8}$ M, although antibodies with higher affinities, e.g. $10^{-9}$ M, or higher, may be even more preferred.

Typically, the antibody that selectively binds CLEC14A polypeptide binds to the mature peptide (residues 22-490) and not to the signal peptide (residues 1-21). In a preferred embodiment, the antibody that selectively binds CLEC14A binds to the extracellular region of CLEC14A (residues 22-396). The antibody may bind to the C-type lectin like domain (residues 32-175) or may bind to the EGF-like region (residues 245-287).

By an antibody that selectively binds a specific portion of CLEC14A we mean that not only does the antibody selectively bind to the target as described above, the antibody molecule also binds the specified portion of the CLEC14A with a greater affinity than for any other portion of it. Preferably, the antibody binds the specified portion with at least 2, or at least 5, or at least 10 or at least 50 times greater affinity than for any other epitope on CLEC14A. More preferably, the antibody molecule binds the specified portion with at least 100, or at least 1,000, or at least 10,000 times greater affinity than for than for any other epitope on the CLEC14A. Such binding may be determined by methods well known in the art, such as one of the Biacore® systems. It is preferred if the antibodies have an affinity for their target epitope on the CLEC14A of at least $10^{-7}$ M and more preferably $10^{-8}$ M, although antibodies with higher affinities, e.g. $10^{-9}$ M, or higher, may be even more preferred. Preferably, the antibody selectively binds the particular specified epitope within the CLEC14A and does not bind any other epitopes within it.

Preferably, when the antibody is administered to an individual, the antibody binds to the target CLEC14A or to the specified portion thereof with a greater affinity than for any other molecule in the individual. Preferably, the antibody binds to (a specified portion of) the CLEC14A with at least 2, or at least 5, or at least 10 or at least 50 times greater affinity than for any other molecule in the individual. More preferably, the agent binds the CLEC14A (at the specific domain) with at least 100, or at least 1,000, or at least 10,000 times greater affinity than any other molecule in the individual. Preferably, the antibody molecule selectively binds the CLEC14A without significantly binding other polypeptides in the body.

The term "antibody" or "antibody molecule" as used herein includes but is not limited to polyclonal, monoclonal, chimaeric, single chain, Fab fragments and fragments produced by a Fab expression library. Such fragments include fragments of whole antibodies which retain their binding activity for a target substance, Fv, F(ab') and F(ab')2 fragments, as well as single chain antibodies (scFv), fusion proteins and other synthetic proteins which comprise the antigen-binding site of the antibody. The term also includes antibody-like molecules which may be produced using phage-display techniques or other random selection techniques for molecules which bind to the specified polypeptide or to particular regions of it. Thus, the term antibody includes all molecules which contain a structure, preferably a peptide structure, which is part of the recognition site (i.e. the part of the antibody that binds or combines with the epitope or antigen) of a natural antibody. Furthermore, the antibodies and fragments thereof may be humanised antibodies, which are now well known in the art.

By "ScFv molecules" we mean molecules wherein the $V_H$ and $V_L$ partner domains are linked via a flexible oligopeptide. Engineered antibodies, such as ScFv antibodies, can be made using the techniques and approaches long known in the art. The advantages of using antibody fragments, rather than whole antibodies, are several-fold. The smaller size of the fragments may lead to improved pharmacological properties, such as better penetration to the target site. Effector functions of whole antibodies, such as complement binding, are removed. Fab, Fv, ScFv and dAb antibody fragments can all be expressed in and secreted from *E. coli*, thus allowing the facile production of large amounts of the fragments. Whole antibodies, and F(ab')$_2$ fragments are "bivalent". By "bivalent" we mean that the antibodies and F(ab')$_2$ fragments have two antigen combining sites. In contrast, Fab, Fv, ScFv and dAb fragments are monovalent, having only one antigen combining site.

It is appreciated that CLEC14A may be a glycoprotein. Thus, the antibody that binds to CLEC14A may bind to any combination of the protein or carbohydrate components of CLEC14A.

Antibodies may be produced by standard techniques, for example by immunisation with the appropriate (glyco) polypeptide or portion(s) thereof, or by using a phage display library.

If polyclonal antibodies are desired, a selected mammal (e.g., mouse, rabbit, goat, horse, etc) is immunised with an immunogenic polypeptide bearing a desired epitope(s), optionally haptenised to another polypeptide. Depending on the host species, various adjuvants may be used to increase immunological response. Such adjuvants include, but are not limited to, Freund's, mineral gels such as aluminium hydroxide, and surface active substances such as lysolecithin, pluronic polyols, polyanions, peptides, oil emulsions, keyhole limpet hemocyanin, and dinitrophenol. Serum from the immunised animal is collected and treated according to known procedures. If serum containing polyclonal antibodies to the desired epitope contains antibodies to other antigens, the polyclonal antibodies can be purified by immunoaffinity chromatography. Techniques for producing and processing polyclonal antisera are well known in the art.

Anti-CLEC14A polyclonal antibodies are commercially available, for example from Sigma-Aldrich (Catalogue No. SAB1400831), R&D Systems (Catalogue Nos. AF4968 and BAF 4968), Abcam (Product code ab73087) and Novus Biologicals (Catalogue No. H00161198-B01).

Monoclonal antibodies directed against entire polypeptides or particular epitopes thereof can also be readily produced by one skilled in the art. The general methodology for making monoclonal antibodies by hybridomas is well known. Immortal antibody-producing cell lines can be created by cell fusion, and also by other techniques such as direct transformation of B lymphocytes with oncogenic DNA, or transfection with Epstein-Barr virus. Panels of monoclonal antibodies produced against the polypeptides listed above can be screened for various properties; i.e., for isotype and epitope affinity. Monoclonal antibodies may be prepared using any of the well known techniques which provides for the production of antibody molecules by continuous cell lines in culture.

It is preferred if the antibody is a monoclonal antibody. In some circumstance, particularly if the antibody is to be administered repeatedly to a human patient, it is preferred if the monoclonal antibody is a human monoclonal antibody or a humanised monoclonal antibody, which are suitable for administration to humans without engendering an immune response by the human against the administered immunoglobulin. Suitably prepared non-human antibodies can be "humanised" in known ways, for example by inserting the CDR regions of mouse antibodies into the framework of human antibodies. Humanised antibodies can be made using the techniques and approaches described in Verhoeyen et al (1988) *Science*, 239, 1534-1536, and in Kettleborough et al, (1991) *Protein Engineering*, *I*4(7), 773-783. In some instances, Fv framework residues of the human immunoglobulin are replaced by corresponding non-human residues. In general, the humanised antibody will contain variable domains in which all or most of the CDR regions correspond to those of a non-human immunoglobulin, and framework regions which are substantially or completely those of a human immunoglobulin consensus sequence.

Completely human antibodies may be produced using recombinant technologies. Typically large libraries comprising billions of different antibodies are used. In contrast to the previous technologies employing chimerisation or humanisation of e.g. murine antibodies this technology does not rely on immunisation of animals to generate the specific antibody. Instead the recombinant libraries comprise a huge number of pre-made antibody variants wherein it is likely that the library will have at least one antibody specific for any antigen. Thus, using such libraries, an existing antibody having the desired binding characteristics can be identified. In order to find the good binder in a library in an efficient manner, various systems where phenotype i.e. the antibody or antibody fragment is linked to its genotype i.e. the encoding gene have been devised. The most commonly used such system is the so called phage display system where antibody fragments are expressed, displayed, as fusions with phage coat proteins on the surface of filamentous phage particles, while simultaneously carrying the genetic information encoding the displayed molecule (McCafferty et al, 1990, *Nature* 348: 552-554). Phage displaying antibody fragments specific for a particular antigen may be selected through binding to the antigen in question. Isolated phage may then be amplified and the gene encoding the selected antibody variable domains may optionally be transferred to other antibody formats, such as e.g. full-length immunoglobulin, and expressed in high amounts using appropriate vectors and host cells well known in the art. Alternatively, the "human" antibodies can be made by immunising transgenic mice which contain, in essence, human immunoglobulin genes (Vaughan et al (1998) *Nature Biotechnol*. 16, 535-539).

It is appreciated that when the antibody is for administration to a non-human individual, the antibody may have been specifically designed/produced for the intended recipient species.

The format of displayed antibody specificities on phage particles may differ. The most commonly used formats are Fab (Griffiths et al, 1994. *EMBO J*. 13: 3245-3260) and single chain (scFv) (Hoogenboom et al, 1992, *J Mol Biol*. 227: 381-388) both comprising the variable antigen binding domains of antibodies. The single chain format is composed of a variable heavy domain ($V_H$) linked to a variable light domain ($V_L$) via a flexible linker (U.S. Pat. No. 4,946,778). Before use as a therapeutic agent, the antibody may be transferred to a soluble format e.g. Fab or scFv and analysed as such. In later steps the antibody fragment identified to have desirable characteristics may be transferred into yet other formats such as full-length antibodies.

WO 98/32845 and Soderlind et al (2000) *Nature BioTechnol*. 18: 852-856 describe technology for the generation of variability in antibody libraries. Antibody fragments derived from this library all have the same framework regions and only differ in their CDRs. Since the framework regions are of germline sequence the immunogenicity of antibodies derived from the library, or similar libraries produced using the same technology, are expected to be particularly low (Soderlind et al, 2000). This property is of great value for therapeutic antibodies, reducing the risk that the patient forms antibodies to the administered antibody, thereby reducing risks for allergic reactions, the occurrence of blocking antibodies, and allowing a long plasma half-life of the antibody. Thus, when developing therapeutic antibodies to be used in humans, modern recombinant library technology (Soderlind et al, 2001, *Comb. Chem. & High Throughput Screen*. 4: 409-416) is now used in preference to the earlier hybridoma technology.

By antibodies we also include heavy-chain antibodies structurally derived from camelidae antibodies, such as Nanobodies® (Ablynx). These are antibody-derived therapeutic proteins that contain the structural and functional properties of naturally-occurring heavy-chain antibodies. The Nanobody® technology was developed following the discovery that camelidae (camels and llamas) possess fully functional antibodies that lack light chains. These heavy-chain antibodies contain a single variable domain (VHH) and two constant domains ($C_H2$ and $C_H3$). The cloned and isolated VHH domain is a perfectly stable polypeptide harbouring the full antigen-binding capacity of the original heavy-chain antibody. These VHH domains with their unique structural and functional properties form the basis of Nanobodies®. They combine the advantages of conventional antibodies (high target specificity, high target affinity and low inherent toxicity) with important features of small molecule drugs (the ability to inhibit enzymes and access receptor clefts). Furthermore, they are stable, have the potential to be administered by means other than injection, are easier to manufacture, and can be humanised. (See, for example U.S. Pat. No. 5,840,526; U.S. Pat. No. 5,874,541; U.S. Pat. No. 6,005,079, U.S. Pat. No. 6,765,087; EP 1 589 107; WO 97/34103; WO97/49805; U.S. Pat. No. 5,800,988; U.S. Pat. No. 5,874,541 and U.S. Pat. No. 6,015,695).

siRNA

Small interfering RNAs are described by Hannon et al. *Nature*, 418 (6894): 244-51 (2002); Brummelkamp et al., *Science* 21, 21 (2002); and Sui et al., *Proc. Natl. Acad. Sci. USA* 99, 5515-5520 (2002). RNA interference (RNAi) is the process of sequence-specific post-transcriptional gene silencing in animals initiated by double-stranded (dsRNA) that is homologous in sequence to the silenced gene. The mediators of sequence-specific mRNA degradation are typically 21- and 22-nucleotide small interfering RNAs (siRNAs) which, in vivo, may be generated by ribonuclease III cleavage from longer dsRNAs. 21-nucleotide siRNA duplexes have been shown to specifically suppress expression of both endogenous and heterologous genes (Elbashir et al (2001) *Nature* 411: 494-498). In mammalian cells it is considered that the siRNA has to be comprised of two complementary 21mers as described below since longer double-stranded (ds) RNAs will activate PKR (dsRNA-dependent protein kinase) and inhibit overall protein synthesis.

Duplex siRNA molecules selective for a polynucleotide encoding the CLEC14A polypeptide can readily be designed by reference to its cDNA sequence. For example, they can be designed by reference to the CLEC14A cDNA sequences in the Genbank Accession No. NM_175060 and as listed in FIG. 1.

Typically, the first 21-mer sequence that begins with an AA dinucleotide which is at least 120 nucleotides downstream from the initiator methionine codon is selected. The RNA sequence perfectly complementary to this becomes the first RNA oligonucleotide. The second RNA sequence should be perfectly complementary to the first 19 residues of the first, with an additional UU dinucleotide at its 3' end. Once designed, the synthetic RNA molecules can be synthesised using methods well known in the art.

The sequence of suitable anti-CLEC14A siRNAs are given below. In addition, anti-CLEC14A siRNAs are commercially available, for example from Applied Biosystems (siRNA ID Nos. s46248, s46249, s46250, 129879, 129880, 129881) and from Invitrogen (Oligo ID Nos. HSS136238, HSS175925 and HSS175926).

siRNAs may be introduced into cells in the patient using any suitable method, such as those described herein. Typically, the RNA is protected from the extracellular environment, for example by being contained within a suitable carrier or vehicle. Liposome-mediated transfer, e.g. the oligofectamine method, may be used.

Antisense Polynucleotides

Antisense nucleic acid molecules selective for a polynucleotide encoding the CLEC14A polypeptide can readily be designed by reference to its cDNA or gene sequence, as is known in the art. Antisense nucleic acids, such as oligonucleotides, are single-stranded nucleic acids, which can specifically bind to a complementary nucleic acid sequence. By binding to the appropriate target sequence, an RNA-RNA, a DNA-DNA, or RNA-DNA duplex is formed. These nucleic acids are often termed "antisense" because they are complementary to the sense or coding strand of the gene. Recently, formation of a triple helix has proven possible where the oligonucleotide is bound to a DNA duplex. It was found that oligonucleotides could recognise sequences in the major groove of the DNA double helix. A triple helix was formed thereby. This suggests that it is possible to synthesise a sequence-specific molecules which specifically bind double-stranded DNA via recognition of major groove hydrogen binding sites. By binding to the target nucleic acid, the above oligonucleotides can inhibit the function of the target nucleic acid. This could, for example, be a result of blocking the transcription, processing, poly(A) addition, replication, translation, or promoting inhibitory mechanisms of the cells, such as promoting RNA degradations.

Antisense oligonucleotides are prepared in the laboratory and then introduced into cells, for example by microinjection or uptake from the cell culture medium into the cells, or they are expressed in cells after transfection with plasmids or retroviruses or other vectors carrying an antisense gene. Antisense oligonucleotides were first discovered to inhibit viral replication or expression in cell culture for Rous sarcoma virus, vesicular stomatitis virus, herpes simplex virus type 1, simian virus and influenza virus. Since then, inhibition of mRNA translation by antisense oligonucleotides has been studied extensively in cell-free systems including rabbit reticulocyte lysates and wheat germ extracts. Inhibition of viral function by antisense oligonucleotides has been demonstrated ex vivo using oligonucleotides which were complementary to the AIDS HIV retrovirus RNA (Goodchild, J. 1988 "Inhibition of Human Immunodeficiency Virus Replication by Antisense Oligodeoxynucleotides", *Proc. Natl. Acad. Sci. (USA)* 85(15): 5507-11). The Goodchild study showed that oligonucleotides that were most effective were complementary to the poly(A) signal; also effective were those targeted at the 5' end of the RNA, particularly the cap and 5N untranslated region, next to the primer binding site and at the primer binding site. The cap, 5' untranslated region, and poly(A) signal lie within the sequence repeated at the ends of retrovirus RNA (R region) and the oligonucleotides complementary to these may bind twice to the RNA.

Typically, antisense oligonucleotides are 15 to 35 bases in length. For example, 20-mer oligonucleotides have been shown to inhibit the expression of the epidermal growth factor receptor mRNA (Witters at al., *Breast Cancer Res Treat* 53:41-50 (1999)) and 25-mer oligonucleotides have been shown to decrease the expression of adrenocorticotropic hormone by greater than 90% (Frankel et al., *J Neurosurg* 91:261-7 (1999)). However, it is appreciated that it may be desirable to use oligonucleotides with lengths outside this range, for example 10, 11, 12, 13, or 14 bases, or 36, 37, 38, 39 or 40 bases.

Antisense polynucleotides may be administered systemically. Alternatively, and preferably, the inherent binding specificity of polynucleotides characteristic of base pairing is enhanced by limiting the availability of the polynucleotide to its intended locus in vivo, permitting lower dosages to be used and minimising systemic effects. Thus, polynucleotides may be applied locally to the solid tumour to achieve the desired effect. The concentration of the polynucleotides at the desired locus is much higher than if the polynucleotides were administered systemically, and the therapeutic effect can be achieved using a significantly lower total amount. The local high concentration of polynucleotides enhances penetration of the targeted cells and effectively blocks translation of the target nucleic acid sequences.

It will be appreciated that antisense agents may also include larger molecules which bind to polynucleotides (mRNA or genes) encoding the CLEC14A polypeptide and substantially prevent expression of the protein. Thus, antisense molecules which are substantially complementary to the respective mRNA are also envisaged.

The molecules may be expressed from any suitable genetic construct and delivered to the patient. Typically, the genetic construct which expresses the antisense molecule comprises at least a portion of the CLEC14A cDNA or gene operatively linked to a promoter which can express the antisense molecule in the cell. Preferably, the genetic construct is adapted for delivery to a human cell.

Ribozymes

Ribozymes are RNA or RNA-protein complexes that cleave nucleic acids in a site-specific fashion. Ribozymes have specific catalytic domains that possess endonuclease activity. For example, a large number of ribozymes accelerate phosphoester transfer reactions with a high degree of specificity, often cleaving only one of several phosphoesters in an oligonucleotide substrate. This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids. For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications, and ribozymes specific for a polynucleotide encoding the CLEC14A polypeptide may be designed by reference to the cDNA sequences listed in the Genbank Accession No. NM_175060 and as listed in FIG. 1.

Methods and routes of administering polynucleotide inhibitors, such as siRNA molecules, antisense molecules and ribozymes, to a patient, are described in more detail below.

Further agents that inhibit transcription of the genes encoding any of the above listed polypeptides can also be designed, for example using an engineered transcription repressor described in Isalan et al (*Nat Biotechnol*, 19(7): 656-60 (2001)) and in Urnov (*Biochem Pharmacol*, 64 (5-6): 919 (2002)). Additionally, they can be selected, for example using the screening methods described in later aspects of the invention.

Formulations and Routes of Administration

It is appreciated that the inhibitor of CLEC14A will typically be formulated for administration to an individual as a pharmaceutical composition, i.e. together with a pharmaceutically acceptable carrier, diluent or excipient.

By "pharmaceutically acceptable" is included that the formulation is sterile and pyrogen free. Suitable pharmaceutical carriers, diluents and excipients are well known in the art of pharmacy. The carrier(s) must be "acceptable" in the sense of being compatible with the inhibitor and not deleterious to the recipients thereof. Typically, the carriers will be water or saline which will be sterile and pyrogen free; however, other acceptable carriers may be used.

In an embodiment, the pharmaceutical compositions or formulations of the invention are for parenteral administration, more particularly for intravenous administration. In a preferred embodiment, the pharmaceutical composition is suitable for intravenous administration to a patient, for example by injection.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

In an alternative preferred embodiment, the pharmaceutical composition is suitable for topical administration to a patient.

Preferably, the formulation is a unit dosage containing a daily dose or unit, daily sub-dose or an appropriate fraction thereof, of the active ingredient.

The inhibitor may be administered orally or by any parenteral route, in the form of a pharmaceutical formulation comprising the active ingredient, optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses.

In human therapy, the inhibitor will generally be administered in admixture with a suitable pharmaceutical excipient, diluent or carrier selected with regard to the intended route of administration and standard pharmaceutical practice.

For example, the inhibitor may be administered orally, buccally or sublingually in the form of tablets, capsules, ovules, elixirs, solutions or suspensions, which may contain flavouring or colouring agents, for immediate-, delayed- or controlled-release applications. The inhibitor may also be administered via intracavernosal injection.

Suitable tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycolate, croscarmellose sodium and certain complex silicates, and granulation binders such as polyvinylpyrrolidone, hydroxypropylmethylcellulose (HPMC), hydroxy-propylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

The inhibitor can also be administered parenterally, for example, intravenously, intra-arterially, intraperitoneally, intrathecally, intraventricularly, intrasternally, intracranially, intra-muscularly or subcutaneously, or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

For oral and parenteral administration to human patients, the daily dosage level of an inhibitor will usually be from 1 to 1,000 mg per adult (i.e. from about 0.015 to 15 mg/kg), administered in single or divided doses.

Thus, for example, the tablets or capsules of the inhibitor may contain from 1 mg to 1,000 mg of active agent for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention.

The inhibitor can also be administered intranasally or by inhalation and are conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetrafluoro-ethane, a hydrofluoroalkane such as 1,1,1,2-tetrafluoroethane (HFA 134A3 or 1,1,1, 2,3,3,3-heptafluoropropane (HFA 227EA3), carbon dioxide or other suitable gas. In the case of a pressurised aerosol, the dosage unit may be determined by providing a valve to deliver a metered amount. The pressurised container, pump, spray or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a antibody and a suitable powder base such as lactose or starch. Such formulations may be particularly useful for treating solid tumours of the lung, such as, for example, small cell lung carcinoma, non-small cell lung carcinoma, pleuropulmonary blastoma or carcinoid tumour.

Aerosol or dry powder formulations are preferably arranged so that each metered dose or "puff" contains at least 1 mg of the inhibitor for delivery to the patient. It will be appreciated that the overall daily dose with an aerosol will vary from patient to patient, and may be administered in a single dose or, more usually, in divided doses throughout the day.

Alternatively, the inhibitor can be administered in the form of a suppository or pessary, particularly for treating or targeting colon, rectal or prostate tumours.

The inhibitor may also be administered by the ocular route. For ophthalmic use, the inhibitor can be formulated as, e.g., micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum. Such formulations may be particularly useful for treating solid tumours of the eye, such as retinoblastoma, medulloepithelioma, uveal melanoma, rhabdomyosarcoma, intraocular lymphoma, or orbital lymphoma.

The inhibitor may be applied topically in the form of a lotion, solution, cream, ointment or dusting powder, or may be transdermally administered, for example, by the use of a skin patch. For application topically to the skin, the inhibitor can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water. Such formulations may be particularly useful for treating solid tumours of the skin, such as, for example, basal cell cancer, squamous cell cancer or melanoma.

For skin cancers, the inhibitors can also be delivered by electroincorporation (EI). EI occurs when small particles of up to 30 microns in diameter on the surface of the skin experience electrical pulses identical or similar to those used in electroporation. In EI, these particles are driven through the stratum corneum and into deeper layers of the skin. The particles can be loaded or coated with inhibitor or can simply act as "bullets" that generate pores in the skin through which the inhibitor can enter.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouth-washes comprising the active ingredient in a suitable liquid carrier. Such formulations may be particularly useful for treating solid tumours of the mouth and throat.

In an embodiment, when the inhibitor is a polypeptide, such as an anti-CLEC14A antibody, it may be delivered using an injectable sustained-release drug delivery system. These are designed specifically to reduce the frequency of injections. An example of such a system is Nutropin Depot which encapsulates recombinant human growth hormone (rhGH) in biodegradable microspheres that, once injected, release rhGH slowly over a sustained period.

The antibody can be administered by a surgically implanted device that releases the drug directly to the required site, for example, into the eye to treat ocular tumours. Such direct application to the site of disease achieves effective therapy without significant systemic side-effects.

An alternative method for delivery of polypeptide inhibitors, such as antibodies, is the ReGel injectable system that is thermo-sensitive. Below body temperature, ReGel is an injectable liquid while at body temperature it immediately forms a gel reservoir that slowly erodes and dissolves into known, safe, biodegradable polymers. The active drug is delivered over time as the biopolymers dissolve.

Polypeptide pharmaceuticals such as antibodies can also be delivered orally. The process employs a natural process for oral uptake of vitamin $B_{12}$ in the body to co-deliver proteins and peptides. By riding the vitamin $B_{12}$ uptake system, the protein or peptide can move through the intestinal wall. Complexes are synthesised between vitamin $B_{12}$ analogues and the drug that retain both significant affinity for intrinsic factor (IF) in the vitamin $B_{12}$ portion of the complex and significant bioactivity of the drug portion of the complex.

Polynucleotides may be administered by any effective method, for example, parenterally (e.g. intravenously, subcutaneously, intramuscularly) or by oral, nasal or other means which permit the polynucleotides to access and circulate in the patient's bloodstream. Polynucleotides administered systemically preferably are given in addition to locally administered polynucleotides, but also have utility in the absence of local administration. A dosage in the range of from about 0.1 to about 10 grams per administration to an adult human generally will be effective for this purpose.

The polynucleotide may be administered as a suitable genetic construct as is described below and delivered to the patient where it is expressed. Typically, the polynucleotide in the genetic construct is operatively linked to a promoter which can express the compound in the cell. The genetic constructs of the invention can be prepared using methods well known in the art, for example in Sambrook et al (2001).

Although genetic constructs for delivery of polynucleotides can be DNA or RNA, it is preferred if they are DNA.

Preferably, the genetic construct is adapted for delivery to a human cell.

Means and methods of introducing a genetic construct into a cell in an animal body are known in the art. For example, the constructs of the invention may be introduced into cells by any convenient method, for example methods involving retroviruses, so that the construct is inserted into the genome of the cell. For example, in Kuriyama et al (1991, *Cell Struc. and Func.* 16, 503-510) purified retroviruses are administered. Retroviral DNA constructs comprising a polynucleotide as described above may be made using methods well known in the art. To produce active retrovirus from such a construct it is usual to use an ecotropic psi2 packaging cell line grown in Dulbecco's modified Eagle's medium (DMEM) containing 10% foetal calf serum (FCS). Transfection of the cell line is conveniently by calcium phosphate co-precipitation, and stable transformants are selected by addition of G418 to a final concentration of 1 mg/ml (assuming the retroviral construct contains a $neo^R$ gene). Independent colonies are isolated and expanded and the culture supernatant removed, filtered through a 0.45 μm pore-size filter and stored at −70° C. For the introduction of the retrovirus into tumour cells, for example, it is convenient to inject directly retroviral supernatant to which 10 μg/ml Polybrene has been added. For tumours exceeding 10 mm in diameter it is appropriate to inject between 0.1 ml and 1 ml of retroviral supernatant; preferably 0.5 ml.

Alternatively, as described in Culver et al (1992, *Science* 256, 1550-1552), cells which produce retroviruses may be injected. The retrovirus-producing cells so introduced are engineered to actively produce retroviral vector particles so that continuous productions of the vector occurred within the tumour mass in situ.

Targeted retroviruses are also available for use in the invention; for example, sequences conferring specific binding affinities may be engineered into pre-existing viral env genes (see Miller & Vile (1995) *Faseb J.* 9, 190-199, for a review of this and other targeted vectors for gene therapy).

Other methods involve simple delivery of the construct into the cell for expression therein either for a limited time or, following integration into the genome, for a longer time. An example of the latter approach includes liposomes (Nässander et al (1992) *Cancer Res.* 52, 646-653).

Other methods of delivery include adenoviruses carrying external DNA via an antibody-polylysine bridge (see Curiel (1993) *Prog. Med. Virol.* 40, 1-18) and transferrin-polycation conjugates as carriers (Wagner et al (1990) *Proc. Natl. Acad. Sci. USA* 87, 3410-3414). In the first of these methods a polycation-antibody complex is formed with the DNA construct or other genetic construct of the invention, wherein the antibody is specific for either wild-type adenovirus or a variant adenovirus in which a new epitope has been introduced which binds the antibody. The polycation moiety binds the DNA via electrostatic interactions with the phosphate backbone. The adenovirus, because it contains unaltered fibre and penton proteins, is internalised into the cell and carries into the cell with it the DNA construct of the invention. It is preferred if the polycation is polylysine.

In an alternative method, a high-efficiency nucleic acid delivery system that uses receptor-mediated endocytosis to carry DNA macromolecules into cells is employed. This is accomplished by conjugating the iron-transport protein transferrin to polycations that bind nucleic acids. Human transferrin, or the chicken homologue conalbumin, or combinations thereof is covalently linked to the small DNA-binding protein protamine or to polylysines of various sizes through a disulphide linkage. These modified transferrin molecules maintain their ability to bind their cognate receptor and to mediate efficient iron transport into the cell. The transferrin-polycation molecules form electrophoretically stable complexes with DNA constructs or other genetic constructs of the invention independent of nucleic acid size (from short oligonucleotides to DNA of 21 kilobase pairs). When complexes of transferrin-polycation and the DNA constructs or other genetic constructs of the invention are supplied to the tumour cells, a high level of expression from the construct in the cells is expected.

High-efficiency receptor-mediated delivery of the DNA constructs or other genetic constructs of the invention using the endosome-disruption activity of defective or chemically inactivated adenovirus particles produced by the methods of Cotten et al (1992) *Proc. Natl. Acad. Sci. USA* 89, 6094-6098 may also be used. This approach appears to rely on the fact that adenoviruses are adapted to allow release of their DNA from an endosome without passage through the lysosome, and in the presence of, for example transferrin linked to the DNA construct or other genetic construct of the invention, the construct is taken up by the cell by the same route as the adenovirus particle. This approach has the advantages that there is no need to use complex retroviral constructs; there is no permanent modification of the genome as occurs with retroviral infection; and the targeted expression system is coupled with a targeted delivery system, thus reducing toxicity to other cell types.

It will be appreciated that "naked DNA" and DNA complexed with cationic and neutral lipids may also be useful in introducing the DNA of the invention into cells of the individual to be treated. Non-viral approaches to gene therapy are described in Ledley (1995, *Human Gene Therapy* 6, 1129-1144).

Although for solid tumours of specific tissues it may be useful to use tissue-specific promoters in the vectors encoding a polynucleotide inhibitor, this is not essential. This is because the targeted genes are only expressed, or selectively expressed, in the tumour endothelium. Accordingly, expression of CLEC14A-specific inhibitors such as siRNA, antisense molecules and ribozymes in the body at locations other than the solid tumour would be expected to have no effect since CLEC14A is not expressed or is expressed at a comparatively low level. Moreover, the risk of inappropriate expression of these inhibitors, in a cell that may express the target polypeptide at a low level, is miniscule compared to the therapeutic benefit to a patient suffering from a solid tumour.

Targeted delivery systems are also known, such as the modified adenovirus system described in WO 94/10323, wherein, typically, the DNA is carried within the adenovirus, or adenovirus-like, particle. Michael et al (1995) *Gene Therapy* 2: 660-668, describes modification of adenovirus to add a cell-selective moiety into a fibre protein. Mutant adenoviruses which replicate selectively in p53-deficient human tumour cells, such as those described in Bischoff et al (1996) *Science* 274: 373-376 are also useful for delivering genetic constructs to a cell. Other suitable viruses, viral vectors or virus-like particles include lentivirus and lentiviral vectors, HSV, adeno-assisted virus (AAV) and AAV-based vectors, vaccinia and parvovirus.

Methods of delivering polynucleotides to a patient are well known to a person of skill in the art and include the use of immunoliposomes, viral vectors (including vaccinia, modified vaccinia, adenovirus and adeno-associated viral (AAV) vectors), and by direct delivery of DNA, e.g. using a gene-gun and electroporation. Furthermore, methods of delivering polynucleotides to a target tissue of a patient for treatment are also well known in the art.

Methods of targeting and delivering therapeutic agents directly to specific regions of the body are well known to a person of skill in the art.

For example, U.S. Pat. No. 6,503,242 describes an implanted catheter apparatus for delivering therapeutic agents directly to the hippocampus. Methods of targeting and delivering agents to the brain can be used for the treatment of solid tumours of the brain. In one embodiment, therapeutic agents including vectors can be distributed throughout a wide region of the CNS by injection into the cerebrospinal fluid, e.g., by lumbar puncture (See e.g., Kapadia et al (1996) *Neurosurg* 10: 585-587). Alternatively, precise delivery of the therapeutic agent into specific sites of the brain can be conducted using stereotactic microinjection techniques. For example, the subject being treated can be placed within a stereotactic frame base (MRI-compatible) and then imaged using high resolution MRI to determine the three-dimensional positioning of the particular region to be treated. The MRI images can then be transferred to a computer having the appropriate stereotactic software, and a number of images are used to determine a target site and trajectory for microinjection of the therapeutic agent. The software translates the trajectory into three-dimensional coordinates that are precisely registered for the stereotactic frame. In the case of intracranial delivery, the skull will be exposed, burr holes will be drilled above the entry site, and the stereotactic apparatus used to position the needle and ensure implantation at a predetermined depth. The therapeutic agent can be delivered to regions of the CNS such as the hippocampus, cells of the spinal cord, brainstem, (medulla, pons, and midbrain), cerebellum, diencephalon (thalamus, hypothalamus), telencephalon (corpus stratium, cerebral cortex, or within the cortex, the occipital, temporal, parietal or frontal lobes), or combinations, thereof. In another embodiment, the therapeutic agent is delivered using other delivery methods suitable for localised delivery, such as localised permeation of the blood-brain barrier. US 2005/0025746 describes delivery systems for localised delivery of an adeno-associated virus vector (AAV) vector encoding a therapeutic agent to a specific region of the brain.

When a therapeutic agent for the treatment of a solid tumour of, for example, the brain, is encoded by a polynucleotide, it may be preferable for its expression to be under the control of a suitable tissue-specific promoter. Central nervous system (CNS) specific promoters such as, neuron-specific promoters (e.g., the neurofilament promoter (Byrne and Ruddle (1989) *Proc. Natl. Acad. Sci. USA* 86: 5473-5477) and glial specific promoters (Morii et al (1991) *Biochem. Biophys Res. Commun.* 175: 185-191) are preferably used for directing expression of a polynucleotide preferentially in cells of the CNS. Preferably, the promoter is tissue specific and is essentially not active outside the central nervous system, or the activity of the promoter is higher in the central nervous system than in other cells or tissues. For example, the promoter may be specific for the spinal cord, brainstem, (medulla, pons, and midbrain), cerebellum, diencephalon (thalamus, hypothalamus), telencephalon (corpus stratium, cerebral cortex, or within the cortex, the occipital, temporal, parietal or frontal lobes), or combinations, thereof. The promoter may be specific for particular cell types, such as neurons or glial cells in the CNS. If it is active in glial cells, it may be specific for astrocytes, oligodendrocytes, ependymal cells, Schwann cells, or microglia. If it is active in neurons, it may be specific for particular types of neurons, e.g., motor neurons, sensory neurons, or interneurons. The promoter may be specific for cells in particular regions of the brain, for example, the cortex, stratium, nigra and hippocampus.

Suitable neuronal specific promoters include, but are not limited to, neuron specific enolase (NSE; Olivia et al (1991) *Genomics* 10: 157-165); GenBank Accession No: X51956), and human neurofilament light chain promoter (NEFL; Rogaev et al (1992) *Hum. Mol. Genet.* 1: 781); GenBank Accession No: L04147). Glial specific promoters include, but are not limited to, glial fibrillary acidic protein (GFAP) promoter (Morii et al (1991); GenBank Accession No: M65210), S100 promoter (Morii et al (1991); GenBank Accession No: M65210) and glutamine synthase promoter (Van den et al (1991) *Biochem. Biophys. Acta.* 2: 249-251); GenBank Accession No: X59834). In a preferred embodiment, the gene is flanked upstream (i.e., 5') by the neuron specific enolase (NSE) promoter. In another preferred embodiment, the gene of interest is flanked upstream (i.e., 5') by the elongation factor 1 alpha (EF) promoter. A hippocampus specific promoter that might be used is the hippocampus specific glucocorticoid receptor (GR) gene promoter.

Alternatively, for treatment of solid tumours of the heart, Svensson et al (1999) describes the delivery of recombinant genes to cardiomyocytes by intramyocardial injection or intracoronary infusion of cardiotropic vectors, such as recombinant adeno-associated virus vectors, resulting in transgene expression in murine cardiomyocytes in vivo (Svensson et al (1999) "Efficient and stable transduction of cardiomyocytes after intramyocardial injection or intracoronary perfusion with recombinant adeno-associated virus vectors." *Circulation.* 99: 201-5). Melo et al review gene and cell-based therapies for heart disease Melo et al (2004) "Gene and cell-based therapies for heart disease." *FASEB J.* 18(6): 648-63). An alternative preferred route of administration is via a catheter or stent. Stents represent an attractive alternative for localized gene delivery, as they provide a platform for prolonged gene elution and efficient transduction of opposed arterial walls. This gene delivery strategy has the potential to decrease the systemic spread of the viral vectors and hence a reduced host immune response. Both synthetic and naturally occurring stent coatings have shown potential to allow prolonged gene elution with no significant adverse reaction (Sharif et al (2004) "Current status of catheter- and stent-based gene therapy." *Cardiovasc Res.* 64(2): 208-16).

It may be desirable to be able to temporally regulate expression of the polynucleotide inhibitor in the cell, although this is not essential for the reasons given above. Thus, it may be desirable that expression of the polynucleotide is directly or indirectly (see below) under the control of a promoter that may be regulated, for example by the concentration of a small molecule that may be administered to the patient when it is desired to activate or, more likely, repress (depending upon whether the small molecule effects activation or repression of the said promoter) expression of the antibody from the polynucleotide. This may be of particular benefit if the expression construct is stable, i.e., capable of expressing the inhibitor (in the presence of any necessary regulatory molecules), in the cell for a period of at least one week, one, two, three, four, five, six, eight months or one or more years. Thus the polynucleotide may be operatively linked to a regulatable promoter. Examples of regulatable promoters include those referred to in the following papers: Rivera et al (1999) *Proc Natl Acad Sci USA* 96(15), 8657-62 (control by rapamycin, an orally bioavailable drug, using two separate adenovirus or adeno-associated virus (AAV) vectors, one encoding an inducible human growth hormone (hGH) target gene, and the other a bipartite rapamycin-regulated transcription factor); Magari et al (1997) *J Clin Invest* 100(11), 2865-72 (control by rapamycin); Bueler (1999) *Biol Chem* 380(6), 613-22 (review of adeno-associated viral vectors); Bohl et al (1998) *Blood* 92(5), 1512-7 (control by doxycycline in adeno-associated vector); Abruzzese at al (1996) *J Mol Med* 74(7), 379-92 (review of induction factors, e.g. hormones, growth factors, cytokines, cytostatics, irradiation, heat shock and associated responsive elements).

For veterinary use, the inhibitor is typically administered as a suitably acceptable formulation in accordance with normal veterinary practice and the veterinary surgeon will determine the dosing regimen and route of administration which will be most appropriate for a particular animal.

Combination Therapy

According to a National Cancer Institute Press Release dated 14 Apr. 2005, updated 16 Jun. 2005, ("Bevacizumab Combined With Chemotherapy Improves Progression-Free Survival for Patients With Advanced Breast Cancer"), the angiogenesis inhibitor anti-VEGF monoclonal antibody bevacizumab improves the clinical outcome for a number of solid tumours when administered in combination with standard chemotherapy. Combinations that have been used include bevacizumab in combination with irinotecan, fluorouracil, and leucovorin; bevacizumab in combination with FOLFOX4 (a regimen of oxaliplatin, 5-fluorouracil and leucovorin); bevacizumab in combination with paclitaxel; and bevacizumab in combination with paclitaxel and carboplatin.

It is therefore appreciated that although the inhibitors of CLEC14A described above may be clinically effective in the absence of any other anti-cancer compound, it may be advantageous to administer these inhibitors in conjunction with a further anticancer agent.

Accordingly, in an embodiment, the method may also comprising administering to the individual at least one further anticancer agent. The method may comprise administering to the individual a pharmaceutical composition containing the inhibitor of CLEC14A and the further anticancer agent. However, it is appreciated that the inhibitor of CLEC14A and the further anticancer agent may be administered separately, for instance by separate routes of administration. Thus it is appreciated that the inhibitor of CLEC14A and the at least one further anticancer agent can be administered sequentially or (substantially) simultaneously. They may be administered within the same pharmaceutical formulation or medicament or they may be formulated and administered separately.

In an embodiment of the medical uses, the medicament containing the inhibitor of CLEC14A may also comprise at least one further anticancer agent.

In another embodiment of the medical uses, the individual to be treated may be one who is administered at least one further anticancer agent. It is appreciated that the individual may be administered the further anticancer agent at the same time as the medicament containing the inhibitor of CLEC14A, although the individual may have been (or will be) administered the further anticancer agent before (or after) receiving the medicament containing the inhibitor of CLEC14A.

The further anticancer agent may be selected from alkylating agents including nitrogen mustards such as mechlorethamine ($HN_2$), cyclophosphamide, ifosfamide, melphalan (L-sarcolysin) and chlorambucil; ethylenimines and methylmelamines such as hexamethylmelamine, thiotepa; alkyl sulphonates such as busulphan; nitrosoureas such as carmustine (BCNU), lomustine (CCNU), semustine (methyl-CCNU) and streptozocin (streptozotocin); and triazenes such as decarbazine (DTIC; dimethyltriazenoimidazole-carboxamide); antimetabolites including folic acid analogues such as methotrexate (amethopterin); pyrimidine analogues such as fluorouracil (5-fluorouracil; 5-FU), floxuridine (fluorodeoxyuridine; FUdR) and cytarabine (cytosine arabinoside); and purine analogues and related inhibitors such as mercaptopurine (6-mercaptopurine; 6-MP), thioguanine (6-thioguanine; TG) and pentostatin (2'-deoxycoformycin); natural products including vinca alkaloids such as vinblastine (VLB) and vincristine; epipodophyllotoxins such as etoposide and teniposide; antibiotics such as dactinomycin (actinomycin D), daunorubicin (daunomycin; rubidomycin), doxorubicin, bleomycin, plicamycin (mithramycin) and mitomycin (mitomycin C); enzymes such as L-asparaginase; and biological response modifiers such as interferon alphenomes; miscellaneous agents including platinum coordination complexes such as cisplatin (cis-DDP) and carboplatin; anthracenedione such as mitoxantrone and anthracycline; substituted urea such as hydroxyurea; methyl hydrazine derivative such as procarbazine (N-methylhydrazine, MIH); and adrenocortical suppressant such as mitotane (o,p'-DDD) and aminoglutethimide; taxol and analogues/derivatives; cell cycle inhibitors; proteosome inhibitors such as Bortezomib (Velcade®); signal transductase (e.g. tyrosine kinase) inhibitors such as Imatinib (Glivec®), COX-2 inhibitors, and hormone agonists/antagonists such as flutamide and tamoxifen.

The clinically used anticancer agents are typically grouped by mechanism of action: Alkylating agents, Topoisomerase I inhibitors, Topoisomerase II inhibitors, RNA/DNA antimetabolites, DNA antimetabolites and Antimitotic agents. The US NIH/National Cancer Institute website lists 122 compounds (http://dtp.nci.nih.gov/docs/cancer/searches/standard_mechanism.html), all of which may be used in conjunction with an inhibitor of CLEC14A. They include Alkylating agents including Asaley, AZQ, BCNU, Busulfan, carboxyphthalatoplatinum, CBDCA, CCNU, CHIP, chlorambucil, chlorozotocin, cis-platinum, clomesone, cyanomorpholino-doxorubicin, cyclodisone, dianhydrogalactitol, fluorodopan, hepsulfam, hycanthone, melphalan, methyl CCNU, mitomycin C, mitozolamide, nitrogen mustard, PCNU, piperazine, piperazinedione, pipobroman, porfiromycin, spirohydantoin mustard, teroxirone, tetraplatin, picoplatin (SP-4-3) (cis-aminedichloro(2-methylpyridine)Pt(II)), thio-tepa, triethylenemelamine, uracil nitrogen mustard, Yoshi-864; anitmitotic agents including allocolchicine, Halichondrin B, colchicine, colchicine derivative, dolastatin 10, maytansine, rhizoxin, taxol, taxol derivative, thiocolchicine, trityl cysteine, vinblastine sulphate, vincristine sulphate; Topoisomerase I Inhibitors including camptothecin, camptothecin, Na salt, aminocamptothecin, 20 camptothecin derivatives, morpholinodoxorubicin; Topoisomerase II Inhibitors including doxorubicin, amonafide, m-AMSA, anthrapyrazole derivative, pyrazoloacridine, bisantrene HCL, daunorubicin, deoxydoxorubicin, mitoxantrone, menogaril, N,N-dibenzyl daunomycin, oxanthrazole, rubidazone, VM-26, VP-16; RNA/DNA antimetabolites including L-alanosine, 5-azacytidine, 5-fluorouracil, acivicin, 3 aminopterin derivatives, an antifol, Baker's soluble antifol, dichlorallyl lawsone, brequinar, ftorafur (pro-drug), 5,6-dihydro-5-azacytidine, methotrexate, methotrexate derivative, N-(phosphonoacetyl)-L-aspartate (PALA), pyrazofurin, trimetrexate; DNA antimetabolites including, 3-HP, 2'-deoxy-5-fluorouridine, 5-HP, alpha-TGDR, aphidicolin glycinate, ara-C, 5-aza-2'-deoxycytidine, beta-TGDR, cyclocytidine, guanazole, hydroxyurea, inosine glycodialdehyde, macbecin II, pyrazoloimidazole, thioguanine and thiopurine.

It is, however, preferred that the at least one further anticancer agent is selected from cisplatin; carboplatin; picoplatin; 5-fluorouracil; paclitaxel; mitomycin C; doxorubicin; gemcitabine; tomudex; pemetrexed; methotrexate; irinotecan, fluorouracil and leucovorin; oxaliplatin, 5-fluorouracil and leucovorin; and paclitaxel and carboplatin.

When the further anticancer agent has been shown to be particularly effective for a specific tumour type, it may be preferred that the inhibitor of CLEC14A is used in combination with that further anticancer agent to treat that specific tumour type.

Targeted Delivery of Cytotoxic Agents

One avenue towards the development of more selective, and thus better, anticancer drugs is the targeted delivery of bioactive molecules to the tumour environment by means of binding molecules (for example, human antibodies) that are specific for tumour endothelial markers. Due to their accessibility and to the therapeutic options that they allow (for example, intraluminal blood coagulation or recruitment of immune cells), vascular markers selectively expressed on tumour blood vessels are ideally suited for ligand-based tumour-targeting strategies, allowing for the imaging of tumour neovasculature and for targeting cytotoxic agents to the tumour neovasculature.

Accordingly, a second aspect of the invention provides a method of targeting a cytotoxic agent to tumour neovasculature in the body of an individual, the method comprising administering to the individual a compound comprising (i) an antibody that selectively binds the CLEC14A polypeptide and (ii) a cytotoxic moiety.

This aspect of the invention also provides the use of a compound comprising (i) an antibody that selectively binds the CLEC14A polypeptide and (ii) a cytotoxic moiety in the preparation of a medicament for targeting a cytotoxic agent to tumour neovasculature in the body of an individual. This aspect further provides such a compound for use in targeting a cytotoxic agent to tumour neovasculature in the body of an individual.

Typically the cytotoxic moiety is selected from a directly cytotoxic chemotherapeutic agent, a directly cytotoxic polypeptide, a moiety which is able to convert a prodrug into a cytotoxic drug, a radiosensitizer, a directly cytotoxic nucleic acid, a nucleic acid molecule that encodes a directly or indirectly cytotoxic polypeptide or a radioactive atom. Examples of such cytotoxic moieties, as well as methods of making the conjugates comprising the antibody and the cytotoxic moiety, are provided in our earlier publications WO 02/36771 and WO 2004/046191, incorporated herein by reference.

The cytotoxic moiety may be directly or indirectly toxic to cells in neovasculature or cells which are in close proximity to and associated with neovasculature. By "directly cytotoxic" we include the meaning that the moiety is one which on its own is cytotoxic. By "indirectly cytotoxic" we include the meaning that the moiety is one which, although is not itself cytotoxic, can induce cytotoxicity, for example by its action on a further molecule or by further action on it.

In one embodiment the cytotoxic moiety is a cytotoxic chemotherapeutic agent. Cytotoxic chemotherapeutic agents are well known in the art. Cytotoxic chemotherapeutic agents, such as anticancer agents, include those listed herein.

Various of these cytotoxic moieties, such as cytotoxic chemotherapeutic agents, have previously been attached to antibodies and other targeting agents, and so compounds of the invention comprising these agents may readily be made by the person skilled in the art. For example, carbodiimide conjugation (Bauminger & Wilchek (1980) *Methods Enzymol.* 70, 151-159) may be used to conjugate a variety of agents, including doxorubicin, to antibodies. Other methods for conjugating a cytotoxic moiety to an antibody can also be used. For example, sodium periodate oxidation followed by reductive alkylation of appropriate reactants can be used, as can glutaraldehyde cross-linking. Methods of cross-linking polypeptides are known in the art and described in WO 2004/046191. However, it is recognised that, regardless of which method of producing a compound of the invention is selected, a determination must be made that the antibody maintains its targeting ability and that the attached moiety maintains its relevant function.

In a further embodiment of the invention, the cytotoxic moiety may be a cytotoxic peptide or polypeptide moiety by which we include any moiety which leads to cell death. Cytotoxic peptide and polypeptide moieties are well known in the art and include, for example, ricin, abrin, *Pseudomonas* exotoxin, tissue factor and the like. Methods for linking them to targeting moieties such as antibodies are also known in the art. The use of ricin as a cytotoxic agent is described in Burrows & Thorpe (1993) *Proc. Natl. Acad. Sci. USA* 90, 8996-9000, and the use of tissue factor, which leads to localised blood clotting and infarction of a tumour, has been described by Ran et al (1998) *Cancer Res.* 58, 4646-4653 and Huang et al (1997) *Science* 275, 547-550. Tsai et al (1995) *Dis. Colon Rectum* 38, 1067-1074 describes the abrin A chain conjugated to a monoclonal antibody. Other ribosome inactivating proteins are described as cytotoxic agents in WO 96/06641. *Pseudomonas* exotoxin may also be used as the cytotoxic polypeptide moiety (Aiello et al (1995) *Proc. Natl. Acad. Sci. USA* 92, 10457-10461).

Certain cytokines, such as TNFα, INFγ and IL-2, may also be useful as cytotoxic agents.

Certain radioactive atoms may also be cytotoxic if delivered in sufficient doses. Thus, the cytotoxic moiety may comprise a radioactive atom which, in use, delivers a sufficient quantity of radioactivity to the target site so as to be cytotoxic. Suitable radioactive atoms include phosphorus-32, iodine-125, iodine-131, indium-111, rhenium-186, rhenium-188 or yttrium-90, or any other isotope which emits enough energy to destroy neighbouring cells, organelles or nucleic acid. Preferably, the isotopes and density of radioactive atoms in the compound of the invention are such that a dose of more than 4000 cGy (preferably at least 6000, 8000 or 10000 cGy) is delivered to the target site and, preferably, to the cells at the target site and their organelles, particularly the nucleus.

The radioactive atom may be attached to the antibody in known ways. For example EDTA or another chelating agent may be attached to the antibody and used to attach $^{111}$In or $^{90}$Y. Tyrosine residues may be labelled with $^{125}$I or $^{131}$I.

The cytotoxic moiety may be a radiosensitizer. Radiosensitizers include fluoropyrimidines, thymidine analogues, hydroxyurea, gemcitabine, fludarabine, nicotinamide, halogenated pyrimidines, 3-aminobenzamide, 3-aminobenzodiamide, etanixadole, pimonidazole and misonidazole (see, for example, McGinn et al (1996) *J. Natl. Cancer Inst.* 88, 1193-11203; Shewach & Lawrence (1996) *Invest. New Drugs* 14, 257-263; Horsman (1995) *Acta Oncol.* 34, 571-587; Shenoy & Singh (1992) *Clin. Invest.* 10, 533-551; Mitchell at al (1989) *Int. J. Radiat. Biol.* 56, 827-836; Iliakis & Kurtzman (1989) *Int. J. Radiat. Oncol. Biol. Phys.* 16, 1235-1241; Brown (1989) *Int. J. Radiat. Oncol. Biol. Phys.* 16, 987-993; Brown (1985) *Cancer* 55, 2222-2228).

The cytotoxic moiety may be a procoagulant factor, such as the extracellular domain of tissue factor (Rippmann et al (2000) "Fusion of the tissue factor extracellular domain to a tumour stroma specific single-chain fragment variable antibody results in an antigen-specific coagulation-promoting molecule." *Biochem J.* 349: 805-12; Huang et al (1997) "Tumor infarction in mice by antibody-directed targeting of tissue factor to tumor vasculature." *Science.* 275(5299): 547-550.

The cytotoxic moiety may be an indirectly cytotoxic polypeptide. In a particularly preferred embodiment, the indirectly cytotoxic polypeptide is a polypeptide which has enzymatic activity and can convert a relatively non-toxic prodrug into a cytotoxic drug. When the targeting moiety is an antibody this type of system is often referred to as ADEPT (Antibody-Directed Enzyme Prodrug Therapy). The system requires that the targeting moiety locates the enzymatic portion to the desired site in the body of the patient (e.g. the site of new vascular tissue associated with a tumour) and after allowing time for the enzyme to localise at the site, administering a prodrug which is a substrate for the enzyme, the end product of the catalysis being a cytotoxic compound. The object of the approach is to maximise the concentration of drug at the desired site and to minimise the concentration of drug in normal tissues (Senter et al (1988) "Anti-tumor effects of antibody-alkaline phosphatase conjugates in combination with etoposide phosphate" *Proc. Natl. Acad. Sci. USA* 85, 4842-4846; Bagshawe (1987) *Br. J. Cancer* 56, 531-2; and Bagshawe, et al (1988) "A cytotoxic agent can be generated selectively at cancer sites" *Br. J. Cancer.* 58, 700-703); Bagshawe (1995) *Drug Dev. Res.* 34, 220-230 and WO 2004/046191, describe various enzyme/prodrug combinations which may be suitable in the context of this invention.

Typically, the prodrug is relatively non-toxic compared to the cytotoxic drug. Typically, it has less than 10% of the toxicity, preferably less than 1% of the toxicity as measured in a suitable in vitro cytotoxicity test.

It is likely that the moiety which is able to convert a prodrug to a cytotoxic drug will be active in isolation from the rest of the compound but it is necessary only for it to be active when (a) it is in combination with the rest of the compound and (b) the compound is attached to, adjacent to or internalised in target cells.

The further moiety may be one which becomes cytotoxic, or releases a cytotoxic moiety, upon irradiation. For example, the boron-10 isotope, when appropriately irradiated, releases a particles which are cytotoxic (U.S. Pat. No. 4,348,376; Primus at al (1996) *Bioconjug. Chem.* 7: 532-535).

Similarly, the cytotoxic moiety may be one which is useful in photodynamic therapy such as photofrin (see, for example, Dougherty et al (1998) *J. Natl. Cancer Inst.* 90, 889-905).

Preferences for the individual to be treated, the types of solid tumour, the routes of administration, the antibody, and so on, are as defined above with respect to the first aspect of the invention.

It is appreciated that targeting a cytotoxic agent to tumour neovasculature will act to inhibit tumour neoangiogenesis. Accordingly, a third aspect of the invention provides a method of inhibiting tumour angiogenesis in an individual, the method comprising administering to the individual a compound comprising (i) an antibody that selectively binds the CLEC14A polypeptide and (ii) a cytotoxic moiety, as defined above with respect to the second aspect of the invention. This third aspect also provides the use of a compound comprising (i) an antibody that selectively binds the CLEC14A polypeptide and (ii) a cytotoxic moiety in the preparation of a medicament for inhibiting tumour angiogenesis in an individual. This aspect further provides such a compound for use in inhibiting tumour angiogenesis in an individual. Preferences for the individual to be treated, the types of solid tumour, the routes of administration, the antibody, and so on, are as defined above with respect to the first aspect of the invention.

It is also appreciated that targeting a cytotoxic moiety to tumour neovasculature to inhibit tumour neoangiogenesis as described in the second and third aspects of the invention may be clinically effective in the absence of any other anti-cancer compound, it may be nevertheless be advantageous to administer the compounds in conjunction with a further anticancer agent. Accordingly, in an embodiment of the second and third aspects of the invention, the method may comprise administering to the individual a further anticancer agent. Preferences for the further anticancer agent to be administered are as described above. The compound comprising (i) an antibody that selectively binds the CLEC14A polypeptide and (ii) a cytotoxic moiety and the further anticancer agent may be administered in the form of a pharmaceutical composition containing both of these components. However, it is appreciated that the compound and the further anticancer agent, may be administered separately, for instance by separate routes of administration. Thus it is appreciated that the compound and the at least one further anticancer agent can be administered sequentially or (substantially) simultaneously. They may be administered within the same pharmaceutical formulation or medicament or they may be formulated and administered separately.

Tumour Imaging, Detection and Diagnosis

Antibodies that selectively bind to the CLEC14A polypeptide, when attached to a detectable moiety, may be useful in imaging, for example vascular imaging of tumours. Methods and compounds useful in vascular imaging of tumours are described in our earlier publication WO 02/36771, incorporated herein by reference.

A compound comprising an anti-CLEC14A antibody as defined above and a detectable moiety can be used, in combination with an appropriate detection method, to detect the location of the compound in the individual, and hence to identify the sites and extent of tumour angiogenesis in the individual.

Accordingly, a fourth aspect of the invention provides a method of imaging tumour neovasculature in the body of an individual the method comprising administering to the individual a compound comprising (i) an antibody that selectively binds the CLEC14A polypeptide and (ii) a detectable moiety, and imaging the detectable moiety in the body.

In an embodiment, the method may further comprise the step of detecting the location of the compound in the individual.

By a "detectable moiety" we include the meaning that the moiety is one which, when located at the target site following administration of the compound of the invention into a patient, may be detected, typically non-invasively from outside the body, and the site of the target located. Thus, the compounds of this aspect of the invention are useful in imaging and diagnosis, especially in the imaging and diagnosis of neovasculature of solid tumours.

Typically, the detectable moiety is or comprises a magnetic nano-particle, a radionuclide or a fluorophore.

Thus, in an embodiment, the detectable moiety may be a radioactive atom which is useful in imaging. Suitable radioactive atoms include technetium-99m or iodine-123 for scintigraphic studies. Other readily detectable moieties include, for example, spin labels for magnetic resonance imaging (MRI) such as iodine-123 again, iodine-131, indium-111, fluorine-19, carbon-13, nitrogen-15, oxygen-17, gadolinium, manganese or iron. Clearly, the compound of the invention must have sufficient of the appropriate atomic isotopes in order for the molecule to be detectable.

The radio- or other label may be incorporated in the compound in known ways. For example, if the antibody may be biosynthesised or synthesised by chemical amino acid synthesis using suitable amino acid precursors involving, for example, fluorine-19 in place of hydrogen. Labels such as $^{99m}$Tc, $^{123}$I, $^{186}$Rh, $^{188}$Rh and $^{111}$In can, for example, be attached via cysteine residues in the antibody. Yttrium-90 can be attached via a lysine residue. The IODOGEN method (Fraker at al (1978) *Biochem. Biophys. Res. Comm.* 80, 49-57) can be used to incorporate iodine-123. The reference ("Monoclonal Antibodies in Immunoscintigraphy", J. F. Chatal, CRC Press, 1989) describes other methods in detail.

Many suitable fluorophores and detection methods are well known in the art and are described, for example by Stefan Andersson-Engels et al (1997) "In vivo fluorescence imaging for tissue diagnostics. *Phys. Med. Biol.* 42: 815-824; Altinoglu et al (2008) "Near-Infrared Emitting Fluorophore-Doped Calcium Phosphate Nanoparticles for In Vivo Imaging of Human Breast Cancer" ACS Nano 2(10): 2075-84; and Chin at al (2009) "In-vivo optical detection of cancer using chlorin e6-polyvinylpyrrolidone induced fluorescence imaging and spectroscopy" *BMC Medical Imaging* 9:1 (doi:10.1186/1471-2342-9-1).

Typically, the individual has a solid tumour, preferably such as those described above with respect to the first aspect of the invention, and the neovasculature of the solid tumour is imaged. Thus, the localisation of the antibody at a particular organ in the body indicates that the individual may have or may be developing a solid tumour at that organ. This method may be useful, for example, in determining the size of a previously diagnosed solid tumour, determining the effectiveness of a therapy against the solid tumour, or determining the extent of metastasis of the tumour. Methods for imaging a detectable moiety in the body are well known in the art, and include PET (positron emission tomography).

Accordingly, this aspect of the invention provides a method of detecting, diagnosing or prognosing a solid tumour in an individual, the method comprising:

administering to the individual a compound comprising (i) an antibody that selectively binds the polypeptide CLEC14A and (ii) a detectable moiety, and detecting the presence and/or location of the detectable moiety in the body.

Preferences for the antibody, the compound and the detectable moiety are as described above.

Other Angiogenic Conditions

To the best of our knowledge, an inhibitor of CLEC14A has never previously been suggested to be an inhibitor of angiogenesis. It is also appreciated that inhibition of angiogenesis may be useful in treating angiogenic diseases or conditions other than tumours. There is thus provided in accordance with a fifth aspect of the invention a method of inhibiting angiogenesis in an individual in need thereof comprising administering an inhibitor of CLEC14A to the individual.

Other than tumours, inhibition of angiogenesis may also be useful in combating any disease or condition involving unwanted, undesirable or inappropriate angiogenesis. Such conditions include psoriasis, menorrhagia, endometriosis, arthritis (both inflammatory and rheumatoid), macular degeneration, Paget's disease, retinopathy and its vascular complications (including proliferative and of prematurity, and diabetic retinopathy), benign vascular proliferations, fibroses, obesity and inflammation. Accordingly, this aspect of the invention includes a method of treating these diseases or conditions by administering an inhibitor of CLEC14A to an individual in need thereof. The invention also provides the use of an inhibitor of CLEC14A in the preparation of a medicament for treating these diseases or conditions. These disease and conditions are associated with undesirable neovasculature formation and typically the inhibitor of CLEC14A reduces this to a useful extent.

By "inhibiting angiogenesis" we include the meaning of reducing the rate or level of angiogenesis. The reduction can be a low level reduction of about 10%, or about 20%, or about 30%, or about 40% of the rate or level of angiogenesis. Preferably, the reduction is a medium level reduction of about 50%, or about 60%, or about 70%, or about 80% reduction of the rate or level of angiogenesis. More preferably, the reduction is a high level reduction of about 90%, or about 95%, or about 99%, or about 99.9%, or about 99.99% of the rate or level of angiogenesis. Most preferably, inhibition can also include the elimination of angiogenesis or its reduction to an undetectable level. Methods and assays for determining the rate or level of angiogenesis, and hence for determining whether and to what extent an inhibitor of CLEC14A inhibits angiogenesis, are known in the art, and described herein.

The therapy (treatment) may be on humans or animals. Preferably, the methods of the inventions are used to treat humans.

Preferences for the inhibitor of CLEC14A, formulations and routes of administration etc are as defined above.

Ex Vivo Methods

A sixth aspect of the invention provides an ex vivo method of inhibiting angiogenesis, the method comprising administering an inhibitor of CLEC14A to tissue or cells ex vivo. Typically, this ex vivo method of inhibiting angiogenesis is carried out in the context of an angiogenesis assay or in a model of tumour angiogenesis, such as those described below. Thus the cells may be established tumour cell lines or tumour cells that have been removed from an individual. The tissue or cells are preferably mammalian tissue or cells, and most preferably are human tissue or cells. Preferably, the tissue or cells comprise tumour endothelium, or are a model of tumour endothelium. Preferences for the inhibitor of CLEC14A are as described above with respect to the first aspect of the invention.

Suitable angiogenesis assays include assays for endothelial cell proliferation, migration and invasion, and include the BD BioCoat™ Angiogenesis System for Endothelial Cell Invasion which is available as Catalogue Nos. 354141 and 354142 from BD Biosciences, Bedford, Mass., USA. Suitable models of tumour angiogenesis include assays for migration of tumour endothelial cells, including bFGF- and VEGF-induced migration, proliferation of tumour endothelial cells, and invasion of tumour endothelial cells and aortic ring assays.

Screening

A seventh aspect of the invention provides a method of identifying an agent that may be useful in the treatment of a solid tumour, or a lead compound for the identification of an agent that may be useful in the treatment of a solid tumour, the method comprising:

providing a candidate compound that binds the polypeptide CLEC14A, or a fragment thereof; and testing the candidate compound in an angiogenesis assay, wherein a candidate compound that inhibits angiogenesis in the assay may be an agent that is useful in the treatment of a solid tumour, or may be a lead compound for the identification of an agent that is useful in the treatment of a solid tumour.

In an embodiment, the method further comprises the preceding step of determining whether the candidate compound selectively binds to the CLEC14A polypeptide, or a fragment thereof.

It is appreciated that these methods can be used to identify an anti-angiogenic factor, which may be an anti-cancer agent.

By a CLEC14A polypeptide we include a polypeptide having the sequence listed in FIG. 1 (SEQ ID NO: 1), and naturally-occurring variants thereof. It is appreciated that for the binding assay, it is not necessary to use a polypeptide having 100% sequence identity to the CLEC14A polypeptide sequence listed in FIG. 1 (whether over the full-length polypeptide or the fragment thereof). Accordingly, in this aspect of the invention it is possible to use a polypeptide having at least 80%, more preferably at least 85%, still more preferably at least 90%, yet more preferably at least 95%, or at least 96%, or at least 97%, or at least 98%, or at least 99% sequence identity with the CLEC14A sequence listed in FIG. 1 (whether over the full-length polypeptide or the fragment thereof). It is preferred if the variant polypeptide has a consecutive region of at least 20 amino acid residues, more preferably at least 50 residues, of the sequence of the CLEC14A polypeptide listed in FIG. 1. Such variants may be made, for example, using the methods of recombinant DNA technology, protein engineering and site-directed mutagenesis which are well known in the art.

The percent sequence identity between two polypeptides may be determined using suitable computer programs, for example the GAP program of the University of Wisconsin Genetic Computing Group and it will be appreciated that percent identity is calculated in relation to polypeptides whose sequence has been aligned optimally. The alignment may alternatively be carried out using the Clustal W program (Thompson et al., (1994) *Nucleic Acids Res* 22, 4673-80). The parameters used may be as follows: Fast pairwise alignment parameters: K-tuple(word) size; 1, window size; 5, gap penalty; 3, number of top diagonals; 5. Scoring method: x percent. Multiple alignment parameters: gap open penalty; 10, gap extension penalty; 0.05. Scoring matrix: BLOSUM.

It is also appreciated that in order to determine whether a candidate compound binds to a specified polypeptide, it is not necessary to use the entire full-length polypeptide in the binding assay, and fragments of the polypeptide may be usefully employed. Preferably, the fragment is at least 20 amino acid residues in length, and may be between 20 and 50 residues or between 50 and 100 residues or between 100 and 150 residues or between 150 and 200 residues in length, or more. It is preferred that the fragment is a fragment of, or that the fragment contains, the extracellular domain of the mature CLEC14A polypeptide.

In an embodiment, the candidate compound may be an antibody that selectively binds the CLEC14A polypeptide, or a fragment thereof. Suitable antibodies are described above.

In another embodiment, the candidate compound may be a peptide. Suitable peptides that bind to the CLEC14A polypeptide, or a fragment thereof, may be identified by methods such as phage display of peptide libraries (Scott & Smith (1990) "Searching for peptide ligands with an epitope library." *Science* 249: 386-390; Felici et al (1995) "Peptide and protein display on the surface of filamentous bacteriophage." *Biotechnol. Annu. Rev.* 1: 149-183); and Collins et al (2001) "Cosmix-plexing: a novel recombinatorial approach for evolutionary selection from combinatorial libraries." *J. Biotechnol.* 74: 317-338); including in vivo panning (Pasqualini et al (1997) "αv integrins as receptors for tumor targeting by circulating ligands. *Nature Biotechnol.* 15: 542-546), and solid-phase parallel synthesis (Frank (2002) "The SPOT-synthesis technique. Synthetic peptide arrays on membrane supports—principles and applications." *J. Immunol. Methods* 267: 13-26; and Pinilla et al (2003) "Advances in the use of synthetic combinatorial chemistry: mixture-based libraries." *Nature Med.* 9: 118-122). The dissociation constants of peptides are typically in the micromolar range, although avidity can be improved by multimerization (Terskikh et al (1997) "Peptabody": a new type of high avidity binding protein. *Proc. Natl. Acad. Sci. USA* 94, 1663-1668; and Wrighton at al (1997) "Increased potency of an erythropoietin peptide mimetic through covalent dimerization. *Nature Biotechnol.* 15, 1261-1265).

The primary ligands of C-type lectins are carbohydrates, even though binding of other proteins, lipids or inorganic compounds has been shown. Thus, in another embodiment, the candidate compound may be a carbohydrate, or a molecule containing carbohydrate moieties such as a glycoprotein or gycolipid. It is appreciated that carbohydrate recognition and binding by C-type lectins is calcium dependant. Thus, in this embodiment, the method is carried out in the presence of calcium ions.

In still another embodiment, the candidate compound may be an aptamer, i.e. a single-stranded DNA molecule that folds into a specific ligand-binding structure. Suitable aptamers that bind to the CLEC14A polypeptide, or a fragment thereof, may be identified by methods such as in vitro selection and amplification (Ellington & Szostak (1992) "Selection in vitro of single stranded DNA molecules that fold into specific ligand binding structures." *Nature* 355: 850-852; and Daniels et al (2003) "A tenascin-C aptamer identified by tumor cell SELEX: systematic evolution of ligands by exponential enrichment." *Proc. Natl Acad. Sci. USA* 100, 15416-15421). The aptamer may be a nuclease-stable 'Spiegelmer' (Helmling et al (2004) "Inhibition of ghrelin action in vitro and in vivo by an RNA-Spiegelmer." *Proc. Natl Acad. Sci. USA* 101: 13174-13179). Aptamers typically have dissociation constants in the micromolar to the subnanomolar range.

In yet another embodiment, the candidate compound may be a small organic molecule. Suitable small molecule that bind to the CLEC14A polypeptide, or a fragment thereof, may be identified by methods such as screening large libraries of compounds (Beck-Sickinger & Weber (2001) *Combinational Strategies in Biology and Chemistry* (John Wiley & Sons, Chichester, Sussex); by structure-activity relationship by nuclear magnetic resonance (Shuker et al (1996) "Discovering high-affinity ligands for proteins: SAR by NMR. *Science* 274: 1531-1534); encoded self-assembling chemical libraries Melkko et al (2004) "Encoded self-assembling chemical libraries." *Nature Biotechnol.* 22: 568-574); DNA-templated chemistry (Gartner et al (2004) "DNA-templated organic synthesis and selection of a library of macrocycles. *Science* 305: 1601-1605); dynamic combinatorial chemistry (Ramstrom & Lehn (2002) "Drug discovery by dynamic combinatorial libraries." *Nature Rev. Drug Discov.* 1: 26-36); tethering (Arkin & Wells (2004) "Small-molecule inhibitors of protein-protein interactions: progressing towards the dream. *Nature Rev. Drug Discov.* 3: 301-317); and speed screen (Muckenschnabel et al (2004) "SpeedScreen: label-free liquid chromatography-mass spectrometry-based high-throughput screening for the discovery of orphan protein ligands." *Anal. Biochem.* 324: 241-249). Typically, small organic molecules will have a dissociation constant for the polypeptide in the nanomolar range, particularly for antigens with cavities. The benefits of most small organic molecule binders include their ease of manufacture, lack of immunogenicity, tissue distribution properties, chemical modification strategies and oral bioavailability.

The capability of a candidate compound to bind to or interact with the CLEC14A polypeptide or fragment thereof may be measured by any method of detecting/measuring a protein/protein interaction or other compound/protein interaction, as discussed further below. Suitable methods include methods such as, for example, yeast two-hybrid interactions, co-purification, ELISA, co-immunoprecipitation and surface plasmon resonance methods. Thus, the candidate compound may be considered capable of binding to the polypeptide or fragment thereof if an interaction may be detected between the candidate compound and the polypeptide or fragment thereof by ELISA, co-immunoprecipitation or surface plasmon resonance methods or by a yeast two-hybrid interaction or copurification method. It is preferred that the interaction can be detected using a surface plasmon resonance method. Surface plasmon resonance methods are well known to those skilled in the art. Techniques are described in, for example, O'Shannessy D J (1994) "Determination of kinetic rate and equilibrium binding constants for macromolecular interactions: a critique of the surface plasmon resonance literature" *Curr Opin Biotechnol.* 5(1):65-71; Fivash et al (1998) "BIAcore for macromolecular interaction." *Curr Opin Biotechnol.* 9(1):97-101; Malmqvist (1999) "BIACORE: an affinity biosensor system for characterization of biomolecular interactions." *Biochem Soc Trans.* 27(2):335-40.

It is appreciated that screening assays which are capable of high throughput operation are particularly preferred. Examples may include cell based assays and protein-protein binding assays. An SPA-based (Scintillation Proximity Assay; Amersham International) system may be used. For example, an assay for identifying a compound capable of modulating the activity of a protein kinase may be performed as follows. Beads comprising scintillant and a substrate polypeptide that may be phosphorylated may be prepared. The beads may be mixed with a sample comprising the protein kinase and $^{32}$P-ATP or $^{33}$P-ATP and with the test compound. Conveniently this is done in a multi-well (e.g., 96 or 384) format. The plate is then counted using a suitable scintillation counter, using known parameters for $^{32}$P or $^{33}$P SPA assays. Only $^{32}$P or $^{33}$P that is in proximity to the scintillant, i.e., only that bound to the polypeptide, is detected. Variants of such an assay, for example in which the polypeptide is immobilised on the scintillant beads via binding to an antibody or antibody fragment, may also be used.

Other methods of detecting polypeptide/polypeptide interactions include ultrafiltration with ion spray mass spectroscopy/HPLC methods or other physical and analytical methods. Fluorescence Energy Resonance Transfer (FRET) methods, for example, well known to those skilled in the art, may be used, in which binding of two fluorescent labelled entities may be measured by measuring the interaction of the fluorescent labels when in close proximity to each other.

A further method of identifying a compound that is capable of binding to the CLEC14A polypeptide or fragment thereof is one where the polypeptide is exposed to the compound and any binding of the compound to the said polypeptide is detected and/or measured. The binding constant for the binding of the compound to the CLEC14A polypeptide may be determined. Suitable methods for detecting and/or measuring (quantifying) the binding of a compound to a polypeptide are well known to those skilled in the art and may be performed, for example, using a method capable of high throughput operation, for example a chip-based method. Technology, called VLSIPS™, has enabled the production of extremely small chips that contain hundreds of thousands or more of different molecular probes. These biological chips or arrays have probes arranged in arrays, each probe assigned a specific location. Biological chips have been produced in which each location has a scale of, for example, ten microns. The chips can be used to determine whether target molecules interact with any of the probes on the chip. After exposing the array to target molecules under selected test conditions, scanning devices can examine each location in the array and determine whether a target molecule has interacted with the probe at that location.

It is appreciated that the identification of a candidate compound that binds to the CLEC14A polypeptide or fragment thereof may be an initial step in the drug screening pathway, and the identified compounds may be further selected e.g. for the ability to inhibit angiogenesis.

By "inhibiting angiogenesis" we include the meaning of reducing the rate or level of angiogenesis. The reduction can be a low level reduction of about 10%, or about 20%, or about 30%, or about 40% of the rate or level of angiogenesis. Preferably, the reduction is a medium level reduction of about 50%, or about 60%, or about 70%, or about 80% reduction of the rate or level of angiogenesis. More preferably, the reduction is a high level reduction of about 90%, or about 95%, or about 99%, or about 99.9%, or about 99.99% of the rate or level of angiogenesis. Most preferably, inhibition can also include the elimination of angiogenesis or its reduction to an undetectable level.

Methods and assays for determining the rate or level of angiogenesis, and hence for determining whether and to what extent a test compound inhibits angiogenesis, are known in the art. For example, U.S. Pat. No. 6,225,118, incorporated herein by reference, describes a multicellular ex vivo assay for modelling the combined stages of angiogenesis namely the proliferation, migration and differentiation stages of cell development. The AngioKit, Catalogue No. ZHA-1000, by TCS CellWorks Ltd, Buckingham MK18 2LR, UK, is a suitable model of human angiogenesis for analysing the anti-angiogenic properties of compounds. The rate or level of angiogenesis can also be determined using the aortic ring assay and the sponge angiogenesis assay that are well known in the art.

Assays for endothelial cell proliferation, migration and invasion are also useful as angiogenesis assays. Suitable assays for endothelial cell proliferation and migration are known to a person of skill in the art and are described herein. Suitable assays for endothelial cell invasion are also known to a person of skill in the art and include the BD BioCoat™ Angiogenesis System for Endothelial Cell Invasion which is available as Catalogue Nos. 354141 and 354142 from BD Biosciences, Bedford, Mass., USA.

We also consider that a candidate compound that selectively binds to the CLEC14A polypeptide may inhibit migration of tumour endothelial cells, including bFGF- and VEGF-induced migration, inhibit proliferation of tumour endothelial cells, or invasion of tumour endothelial cells. Accordingly, candidate compounds that show inhibitory activity in the HUVEC migration assay, or that show anti-proliferative activity, or that show anti-invasive activity in an assay such as the BD BioCoat™ Angiogenesis System for Endothelial Cell Invasion (BD Biosciences, Bedford, Mass., USA), may be therapeutically useful in combating solid tumours in which tumour endothelial cell migration, proliferation or invasion contributes to the angiogenesis of neovasculature and hence the pathology of solid tumours.

It is appreciated that these methods may be a drug screening methods, a term well known to those skilled in the art, and the candidate compound may be a drug-like compound or lead compound for the development of a drug-like compound.

The term "drug-like compound" is well known to those skilled in the art, and may include the meaning of a compound that has characteristics that may make it suitable for use in medicine, for example as the active ingredient in a medicament. Thus, for example, a drug-like compound may be a molecule that may be synthesised by the techniques of organic chemistry, less preferably by techniques of molecular biology or biochemistry, and is preferably a small molecule, which may be of less than 5000 Daltons and which may be water-soluble. A drug-like compound may additionally exhibit features of selective interaction with a particular protein or proteins and be bioavailable and/or able to penetrate target cellular membranes or the blood:brain barrier, but it will be appreciated that these features are not essential.

The term "lead compound" is similarly well known to those skilled in the art, and may include the meaning that the compound, whilst not itself suitable for use as a drug (for example because it is only weakly potent against its intended target, non-selective in its action, unstable, poorly soluble, difficult to synthesise or has poor bioavailability) may provide a starting-point for the design of other compounds that may have more desirable characteristics.

In an embodiment, the identified compound is modified, and the modified compound is tested for the ability to inhibit angiogenesis. Suitable assays for the inhibition of angiogenesis are described above.

It is appreciated that the screening methods can be used to identify agents that may be useful in combating solid tumours. Thus, the screening methods preferably also comprise the further step of testing the identified compound or the modified compound for efficacy in an animal model of cancer, particularly a solid tumour. Suitable models are known in the art and include Lewis lung carcinoma subcutaneous implants in mice (homograft in Black 57 mice) or HT29 xenografts subcutaneous implants in nude mice.

The invention may comprise the further step of synthesising an/or purifying the identified compound or the modified compound. The invention may further comprise the step of formulating the compound into a pharmaceutically acceptable composition.

Compounds may also be subjected to other tests, for example toxicology or metabolism tests, as is well known to those skilled in the art.

Thus the invention includes a method for preparing an anticancer compound that may be useful in the treatment of a solid tumour, the method comprising identifying a compound using the screening methods described above and synthesising, purifying and/or formulating the identified compound.

The invention also includes a method of making a pharmaceutical composition comprising the step of mixing the compound identified using the methods described above with a pharmaceutically acceptable carrier.

All of the documents referred to herein are incorporated herein, in their entirety, by reference.

The listing or discussion of an apparently prior-published document in this specification should not necessarily be taken as an acknowledgement that the document is part of the state of the art or is common general knowledge The invention will now be described in more detail by reference to the following Examples and Figures.

FIG. 1: FIG. 1A: Polypeptide sequence of human CLEC14A from Genbank Accession No. NP_778230 (SEQ ID NO: 1). FIG. 1B: cDNA of human CLEC14A from Genbank Accession No. NM_175060 (SEQ ID NO: 2). FIG. 1C: Coding region of human CLEC14A cDNA from positions 348-1820 of NM_175060 (SEQ ID NO: 3).

FIG. 2: A graph showing the relative expression of CLEC14A in HUVECs and other primary cells. CLEC14A was expressed specifically in endothelial cells (HUVEC), and not in human aortic smooth muscle cells (HASMC), human lung fibroblasts (MRC5), human bronchial epithelial cells (HBE), hepatocytes, or peripheral blood mononuclear cells (PBMC).

FIG. 3: In situ hybridisation of CLEC14A orthologue in 24 hour post-fertilisation zebrafish embryo. The zebrafish CLEC14A orthologue is expressed in the dorsal aorta, cardinal vein, and in inter-somitic vessels.

Figure 4:
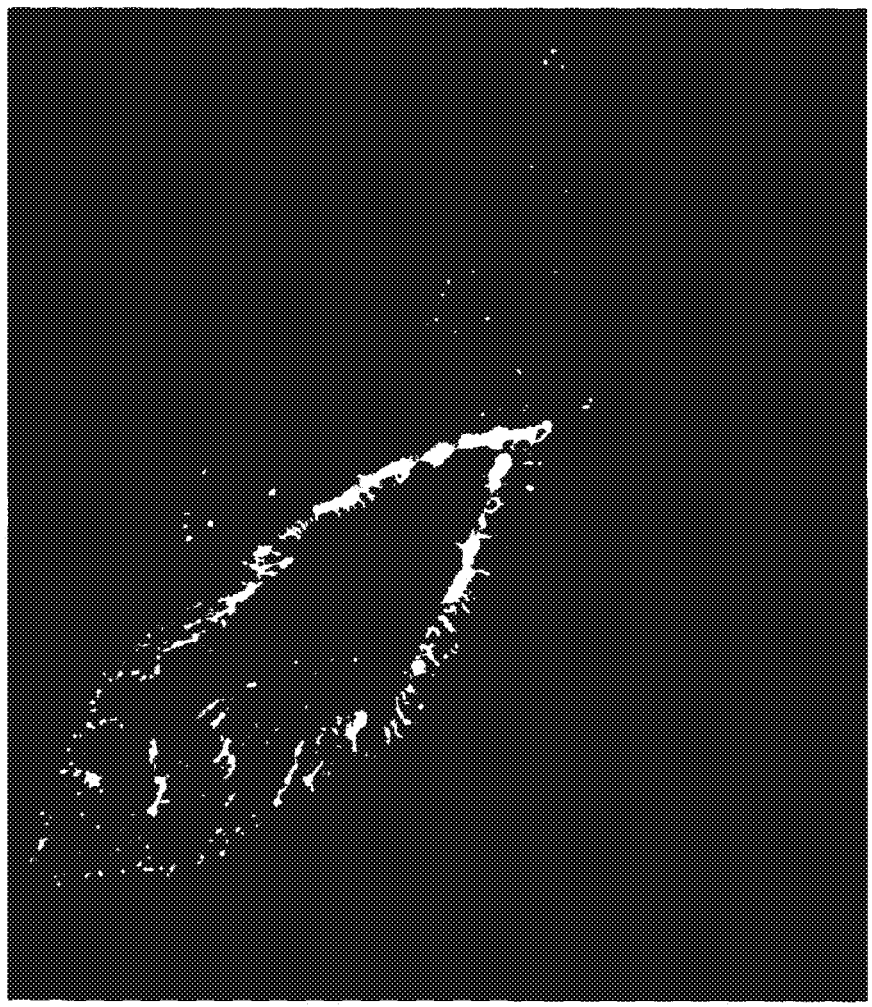

FIG. 4: Live fluorescent imaging of full length CLEC14A-GFP fusion in CHO cells. The CLEC14A-GFP fusion localises at the cellular membrane and is concentrated in filopodia and microspikes, with the same pattern observed in HUVECs.

Figure 5:
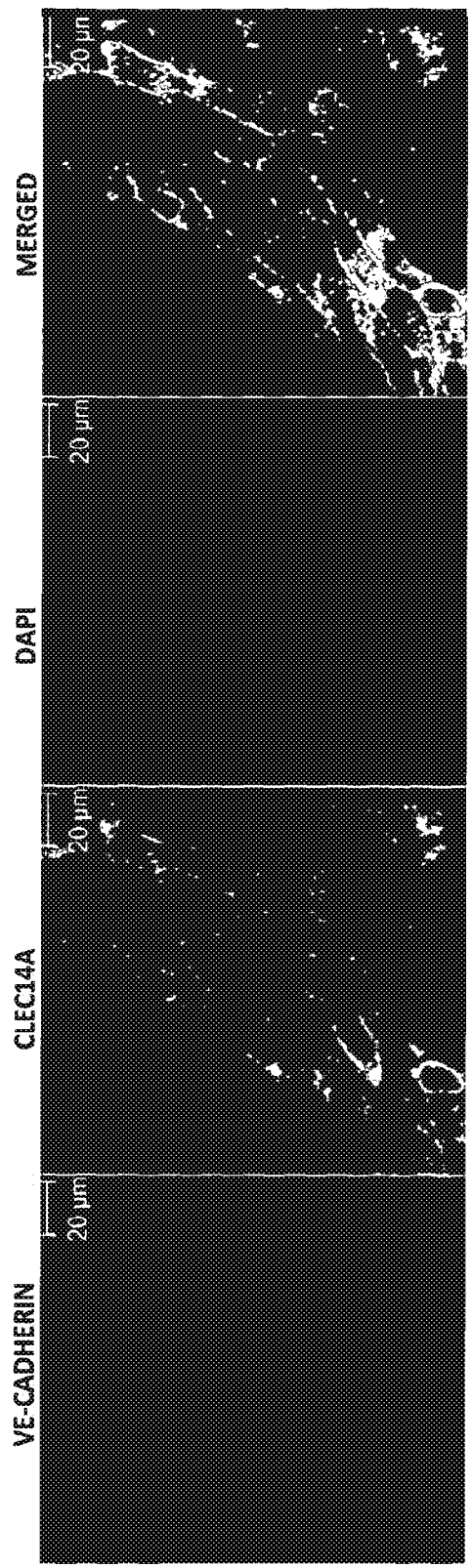

FIG. 5: Confocal imaging of CLEC14A expression and co-localisation with VE-Cadherin in confluent HUVECs. CLEC14A is expressed at the cell junctions and co-localises with VE-Cadherin.

Figure 6:
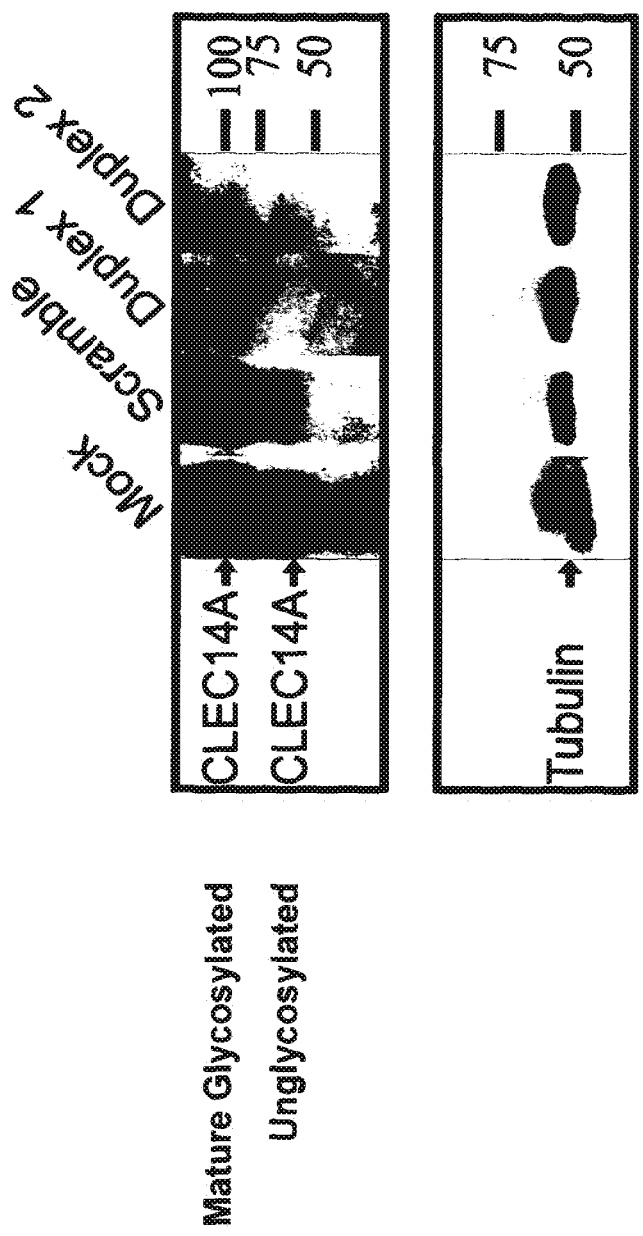

FIG. 6: Western blot of CLEC14A siRNA knockdown in HUVECs. Duplex1 has the sequence GAACAAGACAAT-TCAGTAA (SEQ ID NO: 4) and Duplex2 has the sequence CAATCAGGGTCGACGAGAA (SEQ ID NO: 5). The 'scrambled' oligonucleotide is from Eurogentech, and consists of non-targeting siRNA whose sequence is not displayed. The unglycosylated polypeptide is seen at around 60 kDa and the mature glycosylated protein at around 100 kDa FIG. 7: Confocal imaging of CLEC14A siRNA knockdown in HUVECs, without any effect on the expression of VE-cadherin.

FIG. 8: (A) Light microscopy image of the results of HUVEC scratch wound healing assay with siRNA knockdown, showing a retardation of wound closure following knockdown of CLEC14A by two SiRNA duplexes. (B) Graphical representation of the results from (A).

FIG. 9: (A) Light microscopy image of the results of HUVEC scratch wound healing assay with anti-CLEC14A polyclonal antibodies, again showing a retardation of wound closure. (B) Graphical representation of the results from (A).

FIG. 10: Real time PCR of HUVECs under shear stress and static conditions. Both ROBO4 and CLEC14A mRNAs are down-regulated under laminar shear stress (2 Pa).

Figure 11:
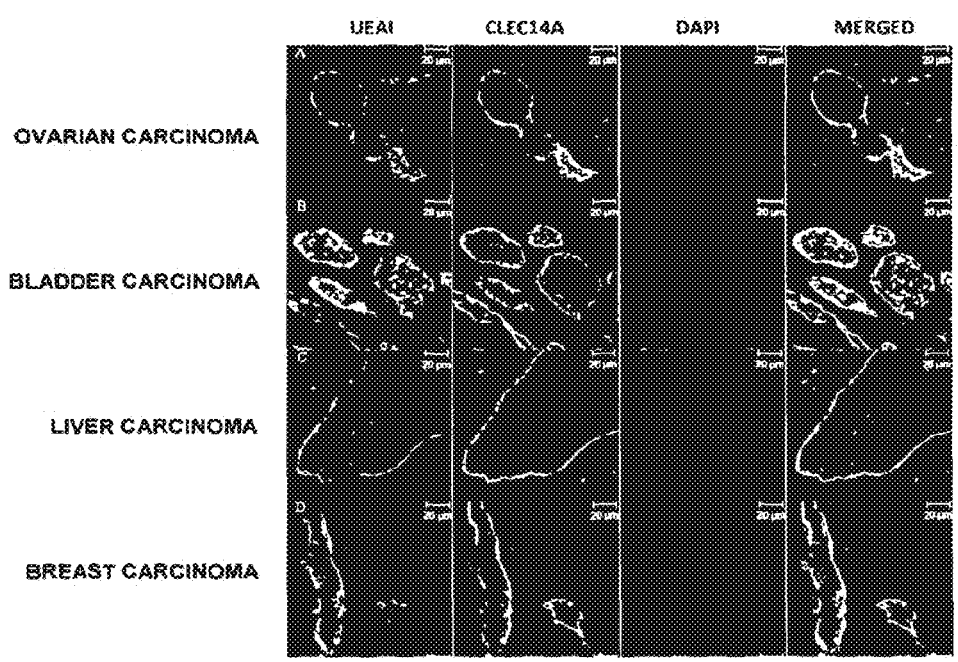

FIG. 11: Immunofluorescence analysis of CLEC14A expression in human ovarian, bladder, liver and breast tumour tissues. CLEC14A expression was restricted to the endothelium in all tumour tissues analysed.

Figure 12:
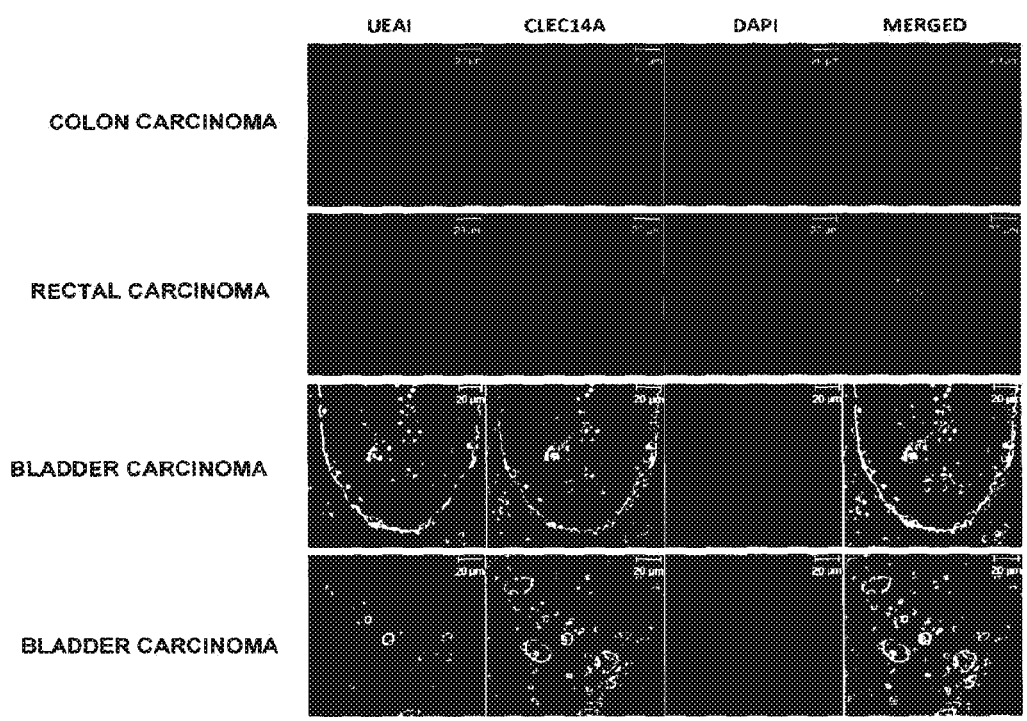

FIG. 12: Immunofluorescence analysis of CLEC14A expression in human colon, rectal and bladder (×2) tumour tissues. CLEC14A expression was restricted to the endothelium in all tumour tissues analysed.

Figure 13:
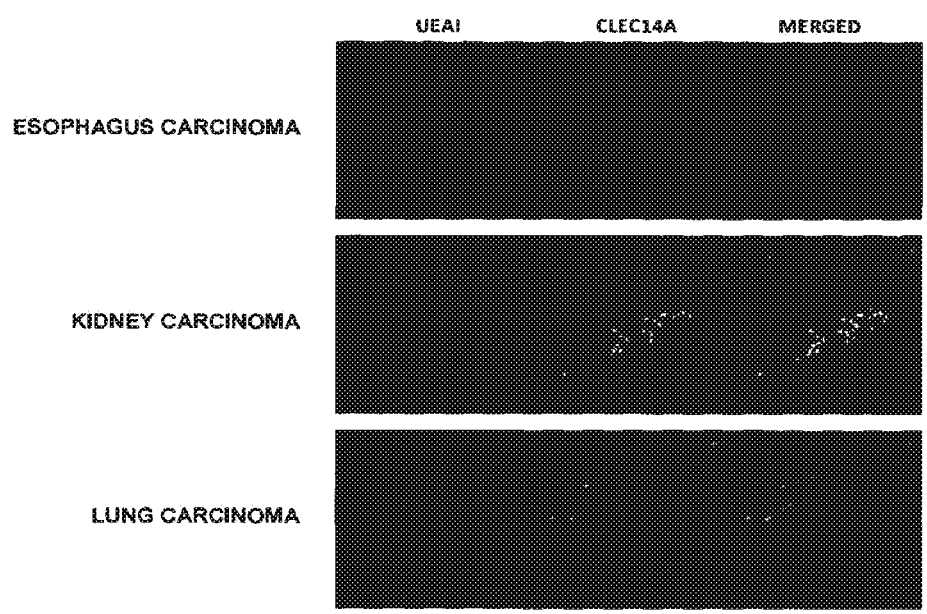

FIG. 13: Immunofluorescence analysis of CLEC14A expression in human oesophagus, kidney and lung tumour tissues. CLEC14A expression was restricted to the endothelium in all tumour tissues analysed.

Figure 14:
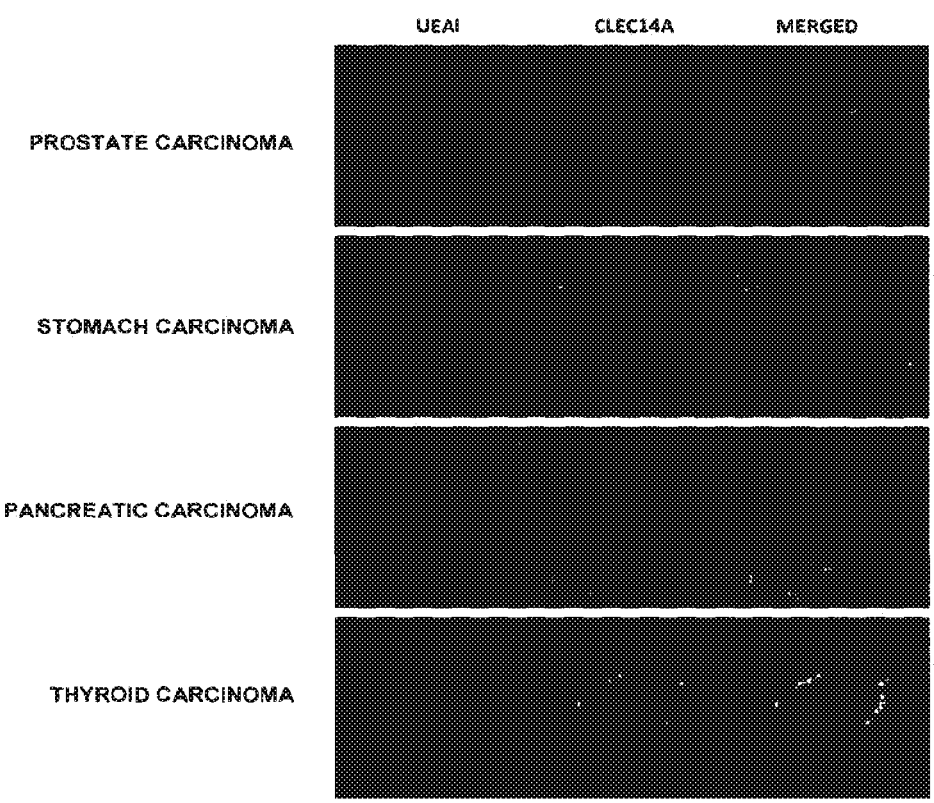

FIG. 14: Immunofluorescence analysis of CLEC14A expression in human prostate, stomach, pancreatic and thyroid tumour tissues. CLEC14A expression was restricted to the endothelium in all tumour tissues analysed.

Figure 15:
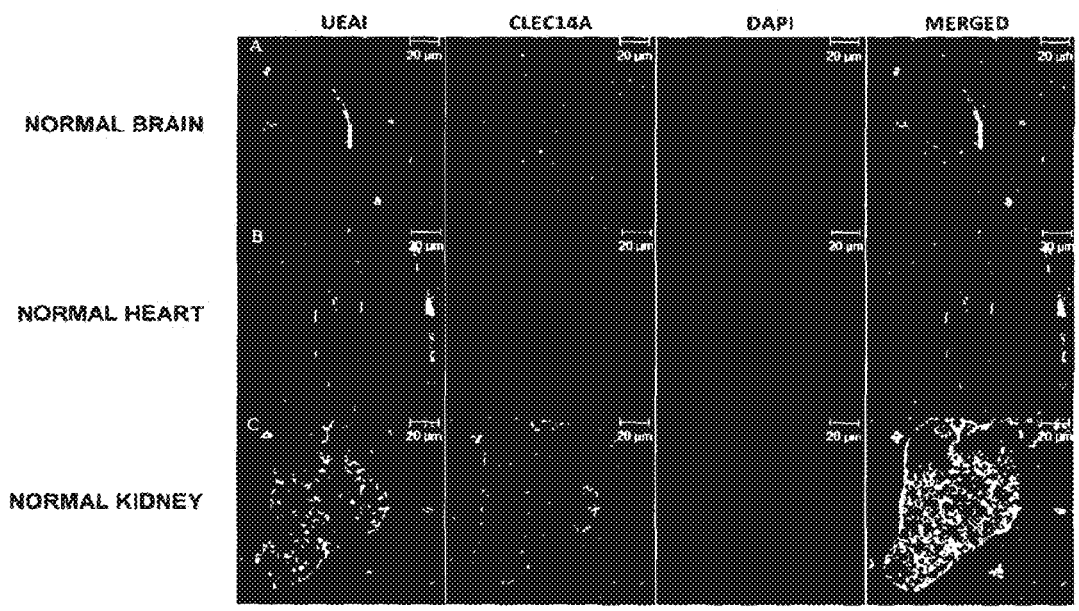

FIG. 15: Immunofluorescence analysis of CLEC14A expression in normal human brain heart and kidney tissues. CLEC14A expression was not detected in any of the normal tissues analysed.

Figure 16B:
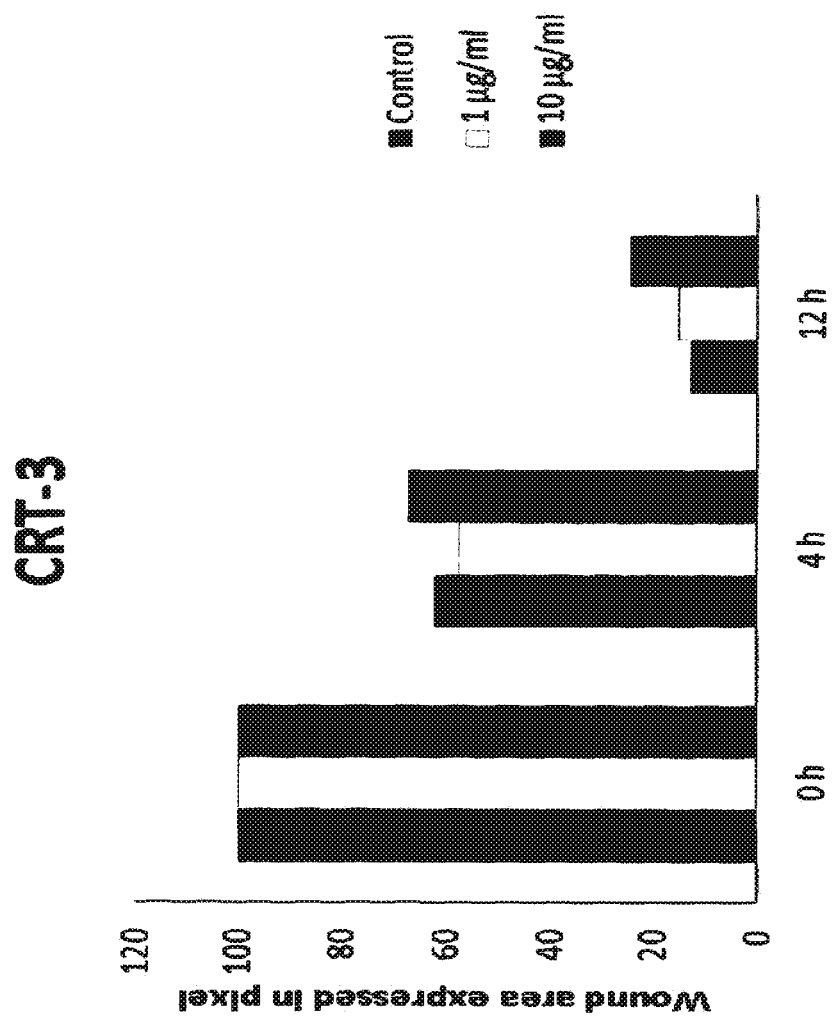

FIG. 16: (A) Light microscopy image of the results of a HUVEC scratch wound healing assay with anti-CLEC14A monoclonal antibody CRT-3 showing a retardation of wound closure. (B) Graphical representation of the results from (A).

FIG. 17: (A) Light microscopy image of the results of a SEND scratch wound healing assay with anti-CLEC14A monoclonal antibody CRT-2 showing a retardation of wound closure. (B) Graphical representation of the results from (A).

EXAMPLE 1

Experimental Studies on CLEC14A

Aims

We carried out a number of experiments to characterise the expression and function of CLEC14A.

Materials and Methods

HUVEC Preparation and Culture

Human umbilical vein endothelial cells (HUVECs) were isolated from umbilical cords donated by the UK National Health Service after informed consent of the donors. Cords were dissected from placentas and the vein was washed in sterile PBS to remove blood. 1 mg/ml of collagenase diluted in M199 medium (Sigma) was injected into the vein and then incubated at 37° C. for 20 minutes to detach the endothelial cells. HUVECs were collected by washing in M199 complete medium containing 10% FCS, 10% large vessel endothelial cell growth supplement (TCS Cell Works), and 4 mM L-glutamine, and plated on 0.1% Type 1 gelatin from porcine skin (Sigma) coated dishes.

Primary Cells Source

Human aortic smooth muscle cells (HASMC) and human bronchial epithelial cells (HBE) were purchased from TCS Cell Works. Human lung fibroblasts (MRC5) were obtained from Cancer Research UK Central Services. Human peripheral blood mononuclear cells (PBMCs) were obtained from the Institute of Cancer Studies at the University of Birmingham. Hepatocytes were a gift from Professor David Adams, School of Immunity and Infection, University of Birmingham.

RNA Extraction and Real Time PCR

Total RNA was isolated from primary cells in culture using TRI reagent (Sigma) followed by cDNA synthesis using a High-Capacity cDNA Archive kit (Applied Biosystems) with supplied random primers. ProbeLibrary Real-time PCR Assay System (Exiqon) was employed in the primary cell screening of CLEC14A expression. Flotillin 2 was chosen as the housekeeping gene to which the expression of CLEC14A was normalized. Primer and probe sets for CLEC14A and Flotillin 2 were designed by ProbeFinder software (Roche). For CLEC14A, primer and probe set was:

5'-CTGGGACCGAGGTGAGTG-3' (SEQ ID NO: 6), and
5'-CGCGATGCAAGTAACTGAGA-3' (SEQ ID NO: 7), with probe number 24.

For Flotillin 2, primer and probe set was:
5'-TGTTGTGGTTCCGACTATAAACAG-3' (SEQ ID NO: 8), and
5'-GGGCTGCAACGTCATAATCT-3' (SEQ ID NO: 9), with probe number 28. Quantitative PCR reactions were performed on the Rotor-Gene RG3000 thermal cycler (Corbett Research). A reaction mix was prepared in triplicate for each primary cell type and 5 ng of cDNA was applied in each reaction. The fold change was calculated using the $\Delta\Delta Ct$ method.

Zebrafish In Situ Hybridisation and RT-PCR

The zebrafish orthologue of human CLEC14A (NM_199786.1, zgc: 66439) cDNA was amplified from a 24 hour post fertilisation (hpf) cDNA preparation using zClec14A primers:

```
                                         (SEQ ID NO: 10)
Forward:    5'-GGAGAAAAAGCAGACAATATCATTTTA-3',
and
                                         (SEQ ID NO: 11)
Reverse:    5'-AGTCTCTCTCACTTAGGTTTCCTCTTT-3'.
```

A 1172 bp PCR fragment generated by these primers was cloned into pCR-Blunt II-TOPO (Invitrogen) following the manufacturer's protocols. The zClec14A clone was sequenced to verify its identity. Digoxigenin labelled sense and antisense RNA probes for in situ hybridisation were generated by in vitro transcription using an RNA labelling kit (Roche). To generate sense probe the plasmid was linearised with KpnI and transcribed with 17. Linearising the plasmid with XhoI and transcribing with SP6 generated the antisense probe. In situ hybridisation was carried out following the method of Thisse & Thisse (2008) "High-resolution in situ hybridisation to whole-mount zebrafish embryos". Nat. Protoc. 3: 59-69.

To analyse the temporal pattern of zClec14A expression, RNA from various stages of zebrafish development were prepared using Trizol reagent (Invitrogen). cDNA was prepared using Superscript III reverse transcriptase (Invitrogen) and random hexamers (Fermentas). ZClec14A was amplified using the following conditions ($T_m$ 55° C., 26 cycles) and zClec14A primers:

```
                                         (SEQ ID NO: 12)
Forward:    5'-AAACCTAAGTGAGAGAGACTGTGC-3',
and
                                         (SEQ ID NO: 13)
Reverse:    5'-ACAGAGTACGCTATTTTCATCCATC-3'.
```

Elongation factor-1α (EF1α) was used as a loading control, and was amplified using the following EF1α primers (Thisse & Thisse (2008)):

```
                                         (SEQ ID NO: 14)
Forward:    5'-CACCCTGGGAGTGAAACA-3',
and
                                         (SEQ ID NO: 15)
Reverse:    5'-ACTTGCAGGCGATGTGAGC-3'.
```

HUVEC Immunofluorescence

HUVECs were grown in glass micro-well chambers (Nunc) fixed in ice-cold methanol, washed with PBST blocked in 10% FCS 3% BSA in PBST. Cells were then stained with CLEC14A antibody following the same protocol used for paraffin embedded sections or co-stained with 5 µg/ml mouse monoclonal IgG antibody against human VE-cadherin, kindly donated by Professor Maria Grazia Lampugnani, Firc Institute for Molecular Oncology, Milan. Sections staining were analyzed with a 510 laser scanning confocal microscope (Carl Zeiss).

CLEC14A-GFP Fusion and CHO Cells Transfection

Full length CLEC14A in PCMV-sport6 vector was purchased from MGC. The sequence was subcloned in a TOPO vector (Invitrogen) and then in pEGFP-N1 vector (Invitrogen). $10^5$ CHO cells were plated and cultured in DMEM (Invitrogen) containing 10% FCS and 4 mM glutamine. 48 hours after seeding, sub-confluent cells were transfected with pEGFP-N1 containing full length CLEC14A using Fugene6 (ROCHE) at the ratio of 6:1. The transfection mixture was added to the cell culture for 24 h and then replaced with serum free DMEM. Cells were analyzed 72 hours post transfection using an Axioscope 2 Plus live fluorescent microscope system (Zeiss) and images were acquired with an Axiocom colour camera (Zeiss).

CLEC14A siRNA Design and CLEC14A Silencing in HUVECs $2.5 \times 10^5$ HUVEC were seeded into 6 well plates the day before transfection. Two different siRNA duplexes for CLEC14A were used, GAACAAGACAATTCAGTAA (Duplex1, SEQ ID NO: 4) and CAATCAGGGTCGACGAGAA (Duplex2, SEQ ID NO: 5) (Eurogentech) and used alongside negative control duplexes. The transfection was performed using 0.3% lipofectamine RNAiMax (Invitrogen) and 10 nM duplexes in optiMEM (Invitrogen). The transfection mix was incubated with the cells for 4 hours before replacing with normal M199 complete medium. Cells were used after 48 hours transfection and knockdown of protein expression was assessed by Western blotting. Protein was isolated using NP40 lysis buffer and quantified using the BioRad Dc protein assay following the manufacturer's instructions (BioRad). Equal amounts of protein in each lane were loaded and separated via SDS PAGE. Proteins were transferred onto nitrocellulose membranes and probed using 0.2 ng/ml of sheep CLEC14A IgG anti-human polyclonal antibody (R&D System) and 0.2 µg/ml of HRP conjugated rabbit polyclonal anti-sheep secondary antibody (Abcam). The same blot was probed with 1 ng/ml of mouse monoclonal anti-tubulin primary antibody and 1 µg/ml of goat polyclonal anti-mouse HRP conjugated secondary antibody.

Scratch Wound Healing Assay with siRNA $2.5 \times 10^5$ HUVEC were seeded into 6 well plates the day before transfection. At 48 hours after transfection a scratch was made with 20 µl pipette tip. Chemokinetic migration of HUVECs was assessed by acquiring images of wound closure at time zero 4, 8, 12 and 24 hours with a Leica DM 1000 light microscope and a USB 2.0 2M Xli camera. The open area of the wound was highlighted and calculated with cell IQ analyzer software.

Scratch Wound Healing Assay with CLEC14A Antisera

A scratch with a 20 μl pipette tip was made in confluent HUVECs. New medium containing 5, 10 and 20 μg/ml of CLEC14A antisera was replaced. Chemokinetic migration of HUVECs was assessed by acquiring images of wound closure at time zero 4, 8, 12 and 24 hours with a Leica DM 1000 light microscope and USB 2.0 2M Xli camera. The open area of the wound was highlighted and calculated with cell IQ analyser software.

Scratch Wound Healing Assay with CLEC14A Monoclonal Antibodies

A scratch with a 10 μl pipette tip was made in confluent HUVECs or cells of the mouse endothelial cell line, SEND. New medium containing 1 μg/ml or 10 μg/ml of a monoclonal CLEC14A antibody raised in mice against the extracellular domain of CLEC14A was applied. Chemokinetic migration of HUVECs or SEND cells was assessed by acquiring images of wound closure at time zero, 4, 6, 12 hours with a Leica DM 1000 light microscope and USB 2.0 2M Xli camera. The open area of the wound was quantitated using Image J software.

Flow Assay

Primary cultures of HUVEC were dissociated with trypsin/EDTA (Sigma) and seeded into rectangular glass capillaries (microslides; internal width 3 mm, depth 0.3 mm) which had been coated with collagen/gelatin. Seeding was at a density that yielded confluent monolayers within 24 hours. After seeding, microslides were placed into specially constructed glass dishes, and attached to glass tubing which had been fused into the wall. Silicon rubber tubing (Tygon R1000; Fisher, Loughborough, UK) was connected to each external arm. The dish contained culture medium and was placed in a humidified $CO_2$ incubator (Nuaire D H; Triple Red, Thame, Oxfordshire, UK). The tubing was passed through a port in the incubator wall. The tubing from two adjacent arms (one attached to a microslide and one empty) was connected and placed into a multichannel, 8-roller pump (model 502S; Watson Marlow Ltd.) forming a continuous flow loop. The bore of the pump tubing and pump speed were chosen to deliver a flow rate (7.76 ml/min) that produced a wall shear stress of 2.0 Pa (=20 $dyn/cm^2$) in the microslide. The pump and external tubing were enclosed in a perspex box, thermostatically regulated at 37° C. The tubing from a separate microslide in each dish was connected to a separate pump. This pumped a small amount of medium through the microslide for 30 s once an hour, to enable prolonged growth under 'static' conditions. HUVEC were cultured under static conditions for 24 hours and then exposed to shear stress of 2.0 Pa for 24 hours. Paired static and flow microslides in each dish were exposed to identical recirculated medium for the same periods.

Immunofluorescence on Paraffin Embedded Tissues

Immunofluorescence was performed on paraffin embedded normal and cancer human tissue collection obtained from Cancer Research UK histology service and on cancer and normal tissue arrays (Superbiochips). Human common cancers 1 (MA2) including 10 cores of each of the following carcinoma: stomach, oesophagus, lung, colon/rectum, thyroid and kidney, and common cancers 2 (MB3) including 10 cores of each of the following carcinomas: breast, liver, bladder, ovarian, pancreas and prostate were used. Two additional control arrays of matching adjacent normal tissues were also analysed. After removal of paraffin, tissues were rehydrated and microwaved for 3 minutes on medium power in citrate buffer pH6 for antigen retrieval. Sections were blocked in PBST containing 10% FCS and 3% BSA. Sections were probed with 10 μg/ml of sheep IgG primary polyclonal antibody against the extracellular domain of human CLEC14A (R&D system) and 15 μg/ml of FITC conjugated rabbit IgG secondary anti-sheep polyclonal antibody (Zymax). Vessel endothelial cells were stained with 20 μg/ml of *Ulex europeaus* agglutinin I (UEAI) conjugated with rhodamine (Vector labs). Slides were permanently mounted with prolong gold anti-fade reagent with DAPI (Invitrogen) to counterstain cell nuclei. Section staining was analysed using a 510 laser scanning confocal microscope (Carl Zeiss).

Preparation of Monoclonal Antibodies

The antigens used for the preparation of monoclonal antibodies were murine CLEC14A-Fc (CM) and human CLEC14A-Fc (CH), optionally conjugated with adjuvant protein (AP). These four antigens (CM, CH, CM-AP, CH-AP) were used for mice immunisation using the following protocol:

| Day | Operation |
| --- | --- |
| 0 | Pre-immune sample taken |
|   | Immunisation of 100 ug of antigen in complete Freunds adjuvant (foot pads) |
| 14 | Immunisation of 100 ug of antigen in incomplete Freunds adjuvant (foot pads) |
| 17 | Test bleed |
| 18 | Popliteal lymph node harvest for fusion |

Sera were tested by ELISA against three antigens: CM, CH and Fc. A non-immune serum was taken as a negative control.

The fusion protocol was as follows:
(1) Popliteal lymph nodes were harvested from the immune mice and homogenised.
(2) Cells were washed with warm DMEM.
(3) Cells were mixed with sp2/0 myeloma cells.
(4) The mixture was centrifuged (1000 g)
(5) The pellet was suspended in 50% PEG 1500 and incubated for 1 min.
(6) The suspension was slowly diluted with warm DMEM.
(7) Suspension was centrifuged (1000 g).
(8) Cells were seeded into plates with peritoneal macrophages.
(9) Cells were cultivated at 37° C. and 5% $CO_2$ More then 500 HAT-resistant hybridoma clones from each mouse were obtained. All of the clone supernatants were tested twice with 4 days interval by ELISA against three absorbed antigens (CM, CH and Fc). Testing resulted in 5 clones (all subclass IgG1) that reacted with both CM and CH and did not react with Fc. All positives were cloned 2-4 times by the limiting dilution method, propagated in culture flasks and injected into mice for ascites. Three clones were derived as a result of immunisation with CLEC14a human (CH), one clone (CRT-3) was the result of immunisation with CLEC14a human-AP (CH-AP), and one clone (CRT-2) was the result of immunisation with CLEC14a mouse-AP (CM-AP).

Results

FIG. 2 is a graph showing the relative expression of CLEC14A in HUVECs and other primary cells. CLEC14A was expressed specifically in endothelial cells. This confirms our previous finding that CLEC14A was endothelial-specific (Herbert et al, 2008).

FIG. 3 illustrates the results of in situ hybridisation of CLEC14A orthologue in 24 hour post-fertilisation zebrafish embryo. The zebrafish CLEC14A orthologue, which is conserved between zebrafish and human, is expressed in the dorsal aorta and in inter-somitic vessels, showing that CLEC14A is expressed only at sites of vasculogenesis and angiogenesis in the zebrafish embryo model.

FIG. 4 shows live fluorescent imaging of a full length CLEC14A-GFP fusion in CHO cells (which do not normally express CLEC14A). The CLEC14A-GFP fusion localises at the membrane in filopodia and microspikes, with the same pattern observed in HUVECs. FIG. 5 shows confocal imaging of CLEC14A expression and co-localisation with VE-Cadherin in confluent HUVECs. CLEC14A is expressed at the cell junctions and co-localises with VE-Cadherin, at cell-cell contact, in protruding microspikes and filopodia. These results clearly show that CLEC14A is a cell-surface expressed protein, making it an ideal molecule for targeting.

Endogenous expression and localisation of CLEC14A in HUVECs was analysed by Western blotting and immunofluorescence. FIG. 6 is a Western blot of CLEC14A siRNA knockdown in HUVECs. CLEC14A was expressed at very high level in HUVECs, showing two bands—one at about 60 kDa (presumably the unglycosylated form of CLEC14A) and one at about 100 kDa (presumably the glycosylated form). Transfection of 10 nM siRNA duplexes specific for CLEC14A into HUVECs decreased the intensity of both bands by approximately 80%, demonstrating that both bands are specific for CLEC14A. FIG. 7 shows confocal imaging of CLEC14A siRNA knockdown in HUVECs. These results demonstrate that the CLEC14A inhibitor siRNA molecules do, in fact, knockdown CLEC14A expression.

The ability of CLEC14A inhibitors to inhibit angiogenesis was examined. FIG. 8A is a light microscopy image showing that siRNA knockdown of CLEC14A inhibits endothelial cell migration in a HUVEC scratch wound healing assay. FIG. 9A is a light microscopy image showing that anti-CLEC14A polyclonal antibodies inhibit endothelial cell migration in a HUVEC scratch wound healing assay. FIGS. 8B and 9B are a graphical representation of the results from 8A and 9A, respectively. Similar results were obtained in scratch wound healing assays using monoclonal antibodies. As shown in FIGS. 16A and B, when HUVECs were treated with 10 µg/ml of monoclonal antibody CRT-3, 25% of the wound area remained open at 12 h compared to 13% in the control. As shown in FIGS. 17 A and B, when SEND cells were treated with 10 µg/ml of monoclonal antibody CRT-2, 17% of the wound area remained open at 12 h compared to 9% in the control. These results show that CLEC14A inhibitors, such as siRNA and antibodies, have an inhibitory effect on endothelial cell migration. Endothelial cell migration is an essential feature of angiogenesis. Accordingly, these assays provide evidence that two distinct molecular inhibitors of CLEC14A, siRNA and antibodies, inhibit angiogenesis.

FIG. 10 illustrates the results from real-time PCR of HUVECs under shear stress and static conditions. ROBO4 is a known tumour endothelial marker, that is highly specific for endothelial cells, and the inhibition of which inhibits angiogenesis. Both ROBO4 and CLEC14A mRNAs are significantly down-regulated under shear stress (2 Pa), and down-regulation under shear stress is a phenomenon that is associated with pro-angiogenesis genes.

The expression of CLEC14A in sections of solid tumours and normal tissue was examined using CLEC14A-specific probes. FIG. 11-14 are immunofluorescence images of CLEC14A expression in human ovarian, bladder, liver, breast, colon, rectal, oesophagus, kidney, lung, prostate, stomach, pancreatic and thyroid tumour tissues. Endothelial specificity of CLEC14A expression was confirmed by co-localisation with *Ulex europeaus* agglutinin I (UEAI) which binds specific fucose residues on endothelial cells. CLEC14A expression was seen in the blood vessels in all tumour tissues analysed. Ovarian, bladder, liver, breast, kidney and prostate tumours were strongly positive for CLEC14A expression, whereas stomach, oesophagus, lung, colon, rectal, pancreatic and thyroid tumour tissues showed a lower level of specific CLEC14A expression. CLEC14A expression was not detected in any of the corresponding normal control (non-tumour) tissues. Representative examples of immunofluorescence images showing an absence of CLEC14A expression in normal human brain, heart and kidney tissues are shown in FIG. 15. Accordingly, we have demonstrated that CLEC14A is specifically expressed in tumour vasculature.

CONCLUSION

Taken together, the results of this study demonstrate that the transmembrane protein CLEC14A is a previously unrecognised tumour endothelial marker.

EXAMPLE 2

Treatment of a Solid Tumour in an Animal Model

A mouse model of a solid tumour (e.g. either a Lewis lung carcinoma subcutaneous homograft implant in Black 57 mice or an HT29 subcutaneous xenograft implant in nude mice) is treated with intravenous infusions of saline solutions of a pharmaceutical composition comprising antibodies that selectively bind to the CLEC14A polypeptide. The infusions are administered weekly for a time of 2 to 4 months. The tumour regresses in the animal model compared to the controls.

The invention claimed is:

1. A method of inhibiting tumour angiogenesis in an individual, the method comprising administering to the individual an inhibitor of CLEC14A, and assessing tumour angiogenesis following administration of the inhibitor of CLEC14A, wherein the inhibitor is an antibody that selectively binds the CLEC14A polypeptide.

2. A method of inhibiting tumour angiogenesis in an individual, the method comprising administering to the individual an inhibitor of CLEC14A, and assessing tumour angiogenesis following administration of the inhibitor of CLEC14A, wherein the inhibitor is an antibody that selectively binds the extracellular domain of mature CLEC14A polypeptide.

3. A method according to claim 2 wherein the antibody is a monoclonal antibody, a humanised antibody or a single-chain antibody.

4. A method of targeting a cytotoxic agent to tumour neovasculature in the body of an individual, the method comprising:

administering to the individual a compound comprising (i) an antibody that selectively binds the extracellular domain of mature CLEC14A polypeptide and (ii) a cytotoxic moiety; and assessing tumour angiogenesis following administration of the compound.

5. A method of inhibiting tumour angiogenesis in an individual the method comprising:

administering to the individual a compound comprising (i) an antibody that selectively binds the extracellular domain of mature CLEC14A polypeptide and (ii) a cytotoxic moiety; and assessing tumour angiogenesis following administration of the compound.

6. A method according to claim 4, wherein the cytotoxic moiety is selected from a directly cytotoxic chemotherapeutic agent, a directly cytotoxic polypeptide, a moiety which is able to convert a prodrug into a cytotoxic drug, a radiosensitizer, a directly cytotoxic nucleic acid, a nucleic acid molecule that encodes a directly or indirectly cytotoxic polypeptide or a radioactive atom.

7. A method according to claim 6 wherein the radioactive atom is phosphorus-32, iodine-125, iodine-131, indium-111, rhenium-186, rhenium-188 or yttrium-90.

8. A method according to claim 2, the method also comprising administering to the individual at least one further anticancer agent.

9. A method according to claim 8 wherein the at least one further anticancer agent is selected from cisplatin; carboplatin; 5-flurouracil; paclitaxel; mitomycin C; doxorubicin; gemcitabine; tomudex; pemetrexed; methotrexate; irinotecan, fluorouracil and leucovorin; oxaliplatin, 5-fluorouracil and leucovorin; and paclitaxel and carboplatin.

10. A method according to claim 2 wherein the individual is a human.

11. A method according to claim 2 wherein the individual has a solid tumour.

12. A method according to claim 11 wherein the solid tumour is a tumour of the colon, rectum, ovary, liver, bladder, prostate, breast, kidney, pancreas, stomach, oesophagus, lung or thyroid.

13. A method according to claim 11 wherein the solid tumour is not a lung tumour or a rectal tumour.

14. A method according to claim 5, wherein the cytotoxic moiety is selected from a directly cytotoxic chemotherapeutic agent, a directly cytotoxic polypeptide, a moiety which is able to convert a prodrug into a cytotoxic drug, a radiosensitizer, a directly cytotoxic nucleic acid, a nucleic acid molecule that encodes a directly or indirectly cytotoxic polypeptide or a radioactive atom.

15. A method according to claim 4, the method also comprising administering to the individual at least one further anticancer agent.

16. A method according to claim 5, the method also comprising administering to the individual at least one further anticancer agent.

17. A method according to claim 4 wherein the individual has a solid tumour.

18. A method according to claim 17 wherein the solid tumour is not a lung tumour or a rectal tumour.

19. A method according to claim 5 wherein the individual has a solid tumour.

20. A method according to claim 19 wherein the solid tumour is not a lung tumour or a rectal tumour.

21. The method according to claim 1, wherein the individual has a lung tumour.

* * * * *

SEQUENCE LISTING

```
<160> NUMBER OF SEQ ID NOS: 15

<210> SEQ ID NO 1
<211> LENGTH: 490
<212> TYPE: PRT
<213> ORGANISM: Homo sapiens

<400> SEQUENCE: 1

Met Arg Pro Ala Phe Ala Leu Cys Leu Leu Trp Gln Ala Leu Trp Pro
1               5                   10                  15

Gly Pro Gly Gly Gly Glu His Pro Thr Ala Asp Arg Ala Gly Cys Ser
            20                  25                  30

Ala Ser Gly Ala Cys Tyr Ser Leu His His Ala Thr Met Lys Arg Gln
        35                  40                  45
```

-continued

```
Ala Ala Glu Glu Ala Cys Ile Leu Arg Gly Gly Ala Leu Ser Thr Val
 50              55                  60

Arg Ala Gly Ala Glu Leu Arg Ala Val Leu Ala Leu Leu Arg Ala Gly
 65              70                  75                  80

Pro Gly Pro Gly Gly Ser Lys Asp Leu Leu Phe Trp Val Ala Leu
                 85                  90                  95

Glu Arg Arg Arg Ser His Cys Thr Leu Glu Asn Glu Pro Leu Arg Gly
                100                 105                 110

Phe Ser Trp Leu Ser Ser Asp Pro Gly Gly Leu Glu Ser Asp Thr Leu
                115                 120                 125

Gln Trp Val Glu Glu Pro Gln Arg Ser Cys Thr Ala Arg Arg Cys Ala
130                 135                 140

Val Leu Gln Ala Thr Gly Gly Val Glu Pro Ala Gly Trp Lys Glu Met
145                 150                 155                 160

Arg Cys His Leu Arg Ala Asn Gly Tyr Leu Cys Lys Tyr Gln Phe Glu
                165                 170                 175

Val Leu Cys Pro Ala Pro Arg Pro Gly Ala Ala Ser Asn Leu Ser Tyr
                180                 185                 190

Arg Ala Pro Phe Gln Leu His Ser Ala Ala Leu Asp Phe Ser Pro Pro
                195                 200                 205

Gly Thr Glu Val Ser Ala Leu Cys Arg Gly Gln Leu Pro Ile Ser Val
210                 215                 220

Thr Cys Ile Ala Asp Glu Ile Gly Ala Arg Trp Asp Lys Leu Ser Gly
225                 230                 235                 240

Asp Val Leu Cys Pro Cys Pro Gly Arg Tyr Leu Arg Ala Gly Lys Cys
                245                 250                 255

Ala Glu Leu Pro Asn Cys Leu Asp Asp Leu Gly Gly Phe Ala Cys Glu
                260                 265                 270

Cys Ala Thr Gly Phe Glu Leu Gly Lys Asp Gly Arg Ser Cys Val Thr
                275                 280                 285

Ser Gly Glu Gly Gln Pro Thr Leu Gly Gly Thr Gly Val Pro Thr Arg
290                 295                 300

Arg Pro Pro Ala Thr Ala Thr Ser Pro Val Pro Gln Arg Thr Trp Pro
305                 310                 315                 320

Ile Arg Val Asp Glu Lys Leu Gly Glu Thr Pro Leu Val Pro Glu Gln
                325                 330                 335

Asp Asn Ser Val Thr Ser Ile Pro Glu Ile Pro Arg Trp Gly Ser Gln
                340                 345                 350

Ser Thr Met Ser Thr Leu Gln Met Ser Leu Gln Ala Glu Ser Lys Ala
                355                 360                 365

Thr Ile Thr Pro Ser Gly Ser Val Ile Ser Lys Phe Asn Ser Thr Thr
                370                 375                 380

Ser Ser Ala Thr Pro Gln Ala Phe Asp Ser Ser Ala Val Val Phe
385                 390                 395                 400

Ile Phe Val Ser Thr Ala Val Val Leu Val Ile Leu Thr Met Thr
                405                 410                 415

Val Leu Gly Leu Val Lys Leu Cys Phe His Glu Ser Pro Ser Ser Gln
                420                 425                 430

Pro Arg Lys Glu Ser Met Gly Pro Pro Gly Leu Glu Ser Asp Pro Glu
                435                 440                 445

Pro Ala Ala Leu Gly Ser Ser Ala His Cys Thr Asn Asn Gly Val
450                 455                 460
```

Lys Val Gly Asp Cys Asp Leu Arg Asp Arg Ala Glu Gly Ala Leu Leu
465                 470                 475                 480

Ala Glu Ser Pro Leu Gly Ser Ser Asp Ala
                485                 490

<210> SEQ ID NO 2
<211> LENGTH: 2256
<212> TYPE: DNA
<213> ORGANISM: Homo sapiens

<400> SEQUENCE: 2

```
ctcctcttgc tctaagcagg gtgtttgacc ttctagtcga ctgcgtcccc tgtacccggc      60
gccagctgtg ttcctgaccc cagaataact cagggctgca ccgggcctgg cagcgctccg     120
cacacatttc ctgtcgcggc ctaagggaaa ctgttggccg ctgggcccgc gggggattc      180 ttggcagttg gggggtccgt cgggagcgag ggcggagggg aagggagggg gaaccgggtt     240
ggggaagcca gctgtagagg gcggtgaccg cgctccagac acagtctgc gtcctcgagc     300 gggacagatc caagttggga gcagctctgc gtgcggggcc tcagagaatg aggccggcgt     360
tcgccctgtg cctcctctgg caggcgctct ggcccgggcc gggcggcggc gaacacccca     420
ctgccgaccg tgctggctgc tcggcctcgg gggcctgcta cagcctgcac cacgctacca     480
tgaagcggca ggcggccgag gaggcctgca tcctgcgagg tgggcgctc agcaccgtgc     540 gtgcgggcgc cgagctgcgc gctgtgctcg cgctcctgcg ggcaggccca gggcccggag     600
ggggctccaa agacctgctg ttctgggtcg cactggagcg caggcgttcc cactgcaccc     660
tggagaacga gcctttgcgg ggtttctcct ggctgtcctc cgaccccggc ggtctcgaaa     720
gcgacacgct gcagtgggtg gaggagcccc aacgctcctg caccgcgcgg agatgcgcgg     780
tactccaggc caccggtggg gtcgagcccc aggctggaa ggagatgcga tgccacctgc     840
gcgccaacgg ctacctgtgc aagtaccagt ttgaggtctt gtgtcctgcg ccgcgccccg     900
gggccgcctc taacttgagc tatcgcgcgc cttccagct gcacagcgcc gctctggact     960
tcagtccacc tgggaccgag gtgagtgcgc tctgccgggg acagctcccg atctcagtta    1020
cttgcatcgc ggacgaaatc ggcgctcgct gggacaaact ctcgggcgat gtgttgtgtc    1080
cctgccccgg gaggtacctc cgtgctggca aatgcgcaga gctccctaac tgcctagacg    1140
acttgggagg ctttgcctgc gaatgtgcta cgggcttcga gctggggaag gacgccgct    1200 cttgtgtgac cagtggggaa ggacagccga cccttggggg gaccggggtg cccaccaggc    1260
gcccgccggc cactgcaacc agcccgtgc cgcagagaac atggccaatc agggtcgacg    1320
agaagctggg agagacacca cttgtccctg aacaagacaa ttcagtaaca tctattcctg    1380
agattcctcg atggggatca cagagcacga tgtctaccct tcaaatgtcc cttcaagccg    1440
agtcaaaggc cactatcacc ccatcaggga gcgtgatttc caagtttaat tctacgactt    1500
cctctgccac tcctcaggct ttcgactcct cctctgccgt ggtcttcata tttgtgagca    1560
cagcagtagt agtgttggtg atcttgacca tgacagtact ggggcttgtc aagctctgct    1620
ttcacgaaag cccctcttcc cagccaagga aggagtctat gggcccgccg ggcctggaga    1680
gtgatcctga gccgctgct ttgggctcca gttctgcaca ttgcacaaac aatgggtga    1740 aagtcgggga ctgtgatctg cgggacagag cagagggtgc cttgctggcg gagtcccctc    1800
ttggctctag tgatgcatag ggaaacaggg gacatggca ctcctgtgaa cagttttca    1860 cttttgatga aacggggaac caagaggaac ttacttgtgt aactgacaat ttctgcagaa    1920 atccccttc ctctaaattc cctttactcc actgaggagc taaatcagaa ctgcacactc    1980
```

```
cttccctgat gatagaggaa gtggaagtgc ctttaggatg gtgatactgg gggaccgggt    2040
agtgctgggg agagatattt tcttatgttt attcggagaa tttggagaag tgattgaact    2100
tttcaagaca ttggaaacaa atagaacaca atataattta cattaaaaaa taatttctac    2160
caaaatggaa aggaaatgtt ctatgttgtt caggctagga gtatattggt tcgaaatccc    2220
agggaaaaaa ataaaaataa aaaattaaag gattgt                              2256
```

<210> SEQ ID NO 3
<211> LENGTH: 1473
<212> TYPE: DNA
<213> ORGANISM: Homo sapiens

<400> SEQUENCE: 3

```
atgaggccgg cgttcgccct gtgcctcctc tggcaggcgc tctggcccgg gccgggcggc     60
ggcgaacacc ccactgccga ccgtgctggc tgctcggcct cggggggcctg ctacagcctg   120 caccacgcta ccatgaagcg gcaggcggcc gaggaggcct gcatcctgcg aggtggggcg   180
ctcagcaccg tgcgtgcggg cgccgagctg cgcgctgtgc tcgcgctcct gcgggcaggc   240
ccagggcccg agggggctc caaagacctg ctgttctggg tcgcactgga gcgcaggcgt    300
tcccactgca ccctggagaa cgagcctttg cggggtttct cctggctgtc ctccgacccc   360
ggcggtctcg aaagcgacac gctgcagtgg gtggaggagc ccaacgctc ctgcaccgcg    420 cggagatgcg cggtactcca ggccaccggt ggggtcgagc ccgcaggctg aaggagatg    480 cgatgccacc tgcgcgccaa cggctacctg tgcaagtacc agtttgaggt cttgtgtcct   540
gcgccgcgcc ccggggccgc tctaacttg agctatcgcg cgcccttcca gctgcacagc    600
gccgctctgg acttcagtcc acctgggacc gaggtgagtg cgctctgccg gggacagctc   660
ccgatctcag ttacttgcat cgcggacgaa atcggcgctc gctgggacaa actctcgggc   720
gatgtgttgt gtccctgccc cgggaggtac ctccgtgctg gcaaatgcgc agagctccct   780
aactgcctag acgacttggg aggctttgcc tgcgaatgtg ctacgggctt cgagctgggg   840
aaggacggcc gctcttgtgt gaccagtggg gaaggacagc cgaccttgg ggggaccggg    900 gtgcccacca ggcgcccgcc ggccactgca accagccccg tgccgcagag aacatggcca   960
atcagggtcg acgagaagct gggagagaca ccacttgtcc ctgaacaaga caattcagta  1020
acatctattc ctgagattcc tcgatgggga tcacagagca cgatgtctac ccttcaaatg  1080
tcccttcaag ccgagtcaaa ggccactatc accccatcag ggagcgtgat ttccaagttt  1140
aattctacga cttcctctgc cactcctcag gctttcgact cctcctctgc cgtggtcttc  1200
atatttgtga gcacagcagt agtagtgttg gtgatcttga ccatgacagt actggggctt  1260
gtcaagctct gctttcacga aagcccctct tcccagccaa ggaaggagtc tatgggcccg  1320
ccgggcctgg agagtgatcc tgagcccgct gctttgggct ccagttctgc acattgcaca  1380
aacaatgggg tgaaagtcgg ggactgtgat ctgcgggaca gagcagaggg tgccttgctg  1440
gcggagtccc ctcttggctc tagtgatgca tag                                1473
```

<210> SEQ ID NO 4
<211> LENGTH: 19
<212> TYPE: DNA
<213> ORGANISM: Artificial Sequence
<220> FEATURE:
<223> OTHER INFORMATION: CLEC14A siRNA duplex 1

<400> SEQUENCE: 4

```
gaacaagaca attcagtaa                                            19

<210> SEQ ID NO 5
<211> LENGTH: 19
<212> TYPE: DNA
<213> ORGANISM: Artificial Sequence
<220> FEATURE:
<223> OTHER INFORMATION: CLEC14A siRNA duplex 2

<400> SEQUENCE: 5
caatcagggt cgacgagaa                                            19

<210> SEQ ID NO 6
<211> LENGTH: 18
<212> TYPE: DNA
<213> ORGANISM: Artificial Sequence
<220> FEATURE:
<223> OTHER INFORMATION: CLEC14A primer

<400> SEQUENCE: 6
ctgggaccga ggtgagtg                                             18

<210> SEQ ID NO 7
<211> LENGTH: 20
<212> TYPE: DNA
<213> ORGANISM: Artificial Sequence
<220> FEATURE:
<223> OTHER INFORMATION: CLEC14A primer

<400> SEQUENCE: 7
cgcgatgcaa gtaactgaga                                           20

<210> SEQ ID NO 8
<211> LENGTH: 24
<212> TYPE: DNA
<213> ORGANISM: Artificial Sequence
<220> FEATURE:
<223> OTHER INFORMATION: Flotillin 2 primer

<400> SEQUENCE: 8
tgttgtggtt ccgactataa acag                                      24

<210> SEQ ID NO 9
<211> LENGTH: 20
<212> TYPE: DNA
<213> ORGANISM: Artificial Sequence
<220> FEATURE:
<223> OTHER INFORMATION: Flotillin 2 primer

<400> SEQUENCE: 9
gggctgcaac gtcataatct                                           20

<210> SEQ ID NO 10
<211> LENGTH: 27
<212> TYPE: DNA
<213> ORGANISM: Artificial Sequence
<220> FEATURE:
<223> OTHER INFORMATION: zClec14A forward primer

<400> SEQUENCE: 10
ggagaaaaag cagacaatat cattta                                    27

<210> SEQ ID NO 11
<211> LENGTH: 27
<212> TYPE: DNA
<213> ORGANISM: Artificial Sequence
```

```
<220> FEATURE:
<223> OTHER INFORMATION: zClec14A reverse primer

<400> SEQUENCE: 11
agtctctctc acttaggttt cctcttt                                            27

<210> SEQ ID NO 12
<211> LENGTH: 24
<212> TYPE: DNA
<213> ORGANISM: Artificial Sequence
<220> FEATURE:
<223> OTHER INFORMATION: zClec14A forward primer

<400> SEQUENCE: 12
aaacctaagt gagagagact gtgc                                               24

<210> SEQ ID NO 13
<211> LENGTH: 25
<212> TYPE: DNA
<213> ORGANISM: Artificial Sequence
<220> FEATURE:
<223> OTHER INFORMATION: zClec14A reverse primer

<400> SEQUENCE: 13
acagagtacg ctattttcat ccatc                                              25

<210> SEQ ID NO 14
<211> LENGTH: 18
<212> TYPE: DNA
<213> ORGANISM: Artificial Sequence
<220> FEATURE:
<223> OTHER INFORMATION: Elongation factor 1 alpha forward primer

<400> SEQUENCE: 14
caccctggga gtgaaaca                                                      18

<210> SEQ ID NO 15
<211> LENGTH: 19
<212> TYPE: DNA
<213> ORGANISM: Artificial Sequence
<220> FEATURE:
<223> OTHER INFORMATION: Elongation factor 1 alpha reverse primer

<400> SEQUENCE: 15
acttgcaggc gatgtgagc                                                     19
```